US006495661B1

(12) United States Patent
Glisson et al.

(10) Patent No.: US 6,495,661 B1
(45) Date of Patent: Dec. 17, 2002

(54) DNA ENCODING THE OUTER MEMBRANE PROTEIN OF *PASTEURELLA MULTOCIDA*

(75) Inventors: John Robert Glisson, Watkinsville, GA (US); Yugang Luo, Millsboro, DE (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/120,051

(22) Filed: Jul. 21, 1998

Related U.S. Application Data
(60) Provisional application No. 60/067,957, filed on Dec. 8, 1997.

(51) Int. Cl.⁷ .............................. C07K 4/00; C07K 5/00; C07K 7/00; C07K 16/00; A61K 38/12

(52) U.S. Cl. ........................ 530/300; 530/300; 530/317; 530/325; 530/326; 530/350; 930/200; 930/270

(58) Field of Search ........................... 424/134.1, 185.1, 424/190.1, 92.1, 255.1; 435/320; 536/23.1; 930/200, 270; 935/23, 34, 38, 47, 49; 530/300, 317, 325, 326, 380

(56) References Cited

U.S. PATENT DOCUMENTS 4,136,169 A * 1/1979 Rebers et al.
5,238,823 A * 8/1993 Potter et al.

OTHER PUBLICATIONS

Chevalier et al. 1993. J. of Bacteriology. 175(1):266–276.*
Manoha et al. 1994. Biochimie. 76:9–14.*
Marandi et al. 1996. Microbiology. 142: 199–206.*
Wood . 1987. Guide to Molecular Cloning Techniques. vol. 152 Section IX. Chapter 49, pp. 443–457, 1987.*
Lubke et al. 1994. Zbl. Bakt. 281:45–54, 1994.*
Zhang et al. 1994. Vet. Immunology and Immunopathology. 41:89–100, 1994.*
Choi et al. 1989. Am J. Vet. Res. 50(5); 676–683.*
Lu et al. 1991. Infection and Immunity. 59(12): 4517–4523.*
Adler, B., et al., "Immunity and Vaccine Development in *Pasteurella Multocida* Infections", *Journal of Biotechnology*, 44(1–3), 139–144, (Jan. 1996).
Arnon, R., "Synthetic Peptides as the Basis for Vaccine Design", *Molecular Immunology*, 28(3), 209–215, (Mar., 1991).
Carter, G.R., "Studies on *Pasteurella Multocida*. I. A Hemagglutination Test for the Identification of Serological Types", *American Journal of Veterinary Research*, 15(60), 481–484, (Jul., 1995).
Chen, R., et al., "Primary Structure of Major Outer–membrane Protein I (ompF Protein, Porin) of *Escherichia Coli* B/r", *The Biochemical Journal Molecular Aspects*, 203, 33–43, (1982).

Choi, K.H., et al., "Characterization of Outer Membrane Protein–enriched Extracts From *Pasteurella Multocida* Isolated From Turkeys", *American Journal of Veterinary Research*, 50(1), 676–683, (1989).
Glisson, J.R., et al., "Cross–Protection Studies With *Pasteurella Multocida* Bacterins Prepared From Bacteria Propagated in Iron–Depleted Medium", *Avian Diseases*, 37(4), 931–1200, (1993).
Glisson, J.R., et al., "In Vivo Antigen Expression by *Pasteurella Multocida*", *Avian Diseases*, 35, 392–396, (1991).
Hofacre, C.L., et al., "Evaluation of *Pasteurella Multocida* Mutants of Low Virulence. I. Development and Pathogenicity", *Avian Disease*, 33, 270–274, (1989).
Hofacre, C.L., et al., "Evaluation of *Pasteurella Multocida* Mutants of Low Virulence. II. Immunologic Response of Turkeys", *Avian Disease*, 33, 275–278, (1989).
Ikeda, J.S., et al., "Antigenically Related Iron–Regulated Outer Membrane Proteins Produced by Different Somatic Serotypes of *Pasteurella Multocida* ", *Infection and Immunity*, 56(9), 2499–2502, (1998).
Jeanteur, D., et al., "The Bacterial Porin Superfamily: Sequence Alignment and Structure Prediction", *Molecular Microbiology*, 5(9), 2153–2164, (1991).
Jeanteur, D., et al., "The Porin Superfamily: Diversity and Common Features", *New Comprehensive Biochemistry*, 27, 363–380, (1994).
Lu, Y.S., et al., "The Outer Membrane of *Pasteurella Multocida* 3:A Protects Rabbits Against Homologous Challenge", *Infection and Immunity*, 59(12), 4517–4523, (1991).
Lubke, A., et al., "Isolation and Partial Characterization of the Major Protein of the Outer Membrane of *Pasteurella haemolytica* and *Pasteurella Multocida*", *Zentralblatt fur Bakteriologie, 281(1)–An International Journal of Medicinal Microbiology, Virology, Parasitology and Infectious Diseases*, 45–54, (Jun., 1994).
Penn, C.W., et al., "Isolation of a Protective, Non–toxic Capsular Antigen From *Pasteurella Multocida*, Types B and E", *Research in Veterinary Science*, 20, 90–96, (1976).
Ruffolo, C.G., et al., "Cloning, Sequencing, Expression, and Protective Capacity of the oma87 Gene Encoding the *Pasteurella Multocida* 87–Kilodalton Outer Membrane Antigen", *Infection and Immunity*, 64(8), 3161–3167, (1996).

(List continued on next page.)

*Primary Examiner*—Mark Navarro
*Assistant Examiner*—Ja-Na A. Hines
(74) *Attorney, Agent, or Firm*—Schwegman, Lundberg, Woessner & Kluth, P.A.

(57) ABSTRACT

An isolated nucleic acid molecule encoding the outer membrane protein of *Pasteurella multocida* is provided. Also provided are methods to detect the presence of the nucleic acid molecule, and antibodies specific for the polypeptide encoded by the nucleic acid molecule, in a sample. Further provided are immunogenic compositions comprising the outer membrane polypeptide or protien of *Pasteurella multocida*, or portions thereof.

2 Claims, 22 Drawing Sheets

OTHER PUBLICATIONS

Figure 1A:
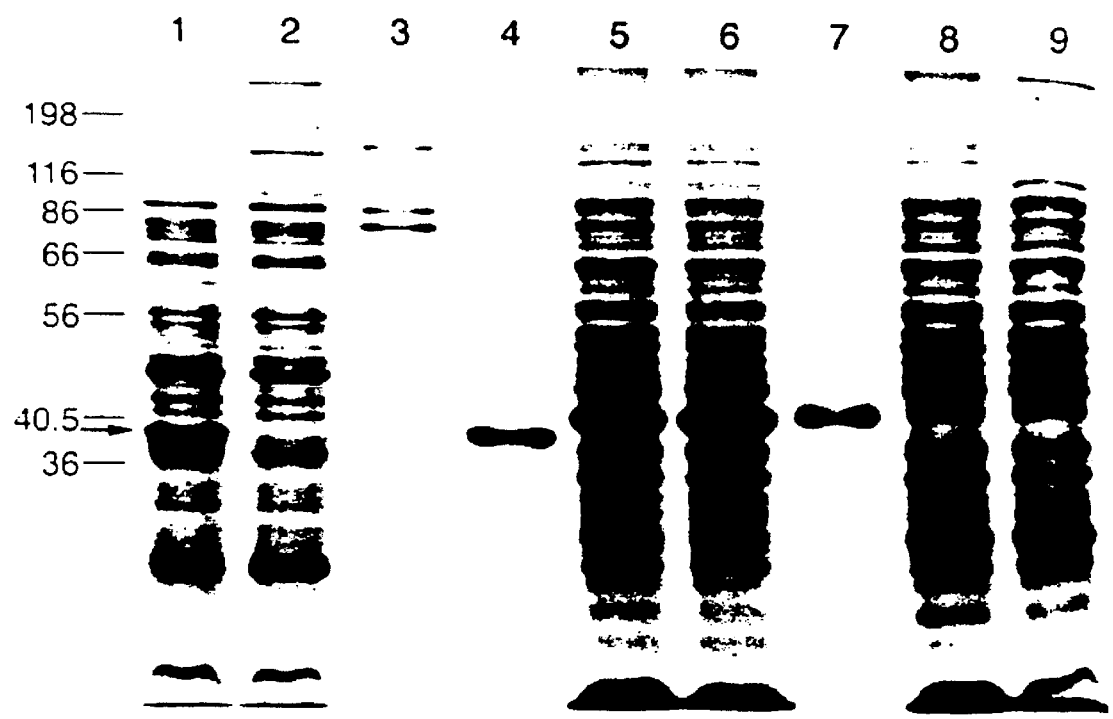

Tsuji, M., et al., "Evaluation of Relationship Among Three Purified Antigens From *Pasteurella Multocida* Strain P–1059 and of Their Protective Capacities in Turkeys.", *American Journal of Veterinary Research*, 49(9), 1516–1521, (Sep. 1988).

Zhang, H., et al., "Use of a 35.5 kDa Cell Membrane Composition of *Pasteurella Multocida* and an Anti–idiotype Antibody to Induce Protective Immunity in Leghorn Chickens", *Veterinary Immunology and Immunopathology*, 41, 89–100, (1994).

Chevalier, G., et al., "Purification, composition en aminoacides et séquence N–terminale de la protéine majoritaire (protéine H) de la membrane externe de *Pasteurella multocida*", *Comptes Rendus De L'Academic Des Sciences, 314* (1), SéIII, pp. 253–258, (Jan. 2, 1992).

Delmarche, C., et al., "Characterization of the *Pasteurella multocida* skp and fir A genes", *Gene, 161*(1), pp. 39–43, (1995).

Kasten, R.W., et al., "*Pasteurella multocida* produces a protein with homology to the P6 outer membrane protein of *Haemophilus influenzae*", *Infection and Immunity, 63* (3), pp. 989–993, (Mar. 1996).

Marandi, M.V., et al., "Role of Outer Membrane protein h (OmpH)– and OmpA–Specific Monoclonal Antibodies from Hybridoma Tumors in protection of Mice Against *Pasteurella multocida*", *Infection and Immunity, 65* (11), pp. 4502–4508, (Nov. 1997).

* cited by examiner

```
  1 MKKTIVALAVAAVAATSA-NAATVYNQDGTKVDVNGSLRL-ILKKEK---           50
    ||||  || | | || || ||| |||  ||||    |   |   |
  1 MKKTLAALIVGAFAA-SAANAAVVYNNEGTKVELGG--RVSIIA-EQSTS           50

51 NERGD-------LVDN-GSRVSF--KASHDLGEGLSALAYTELRFSKNVP          100
    | | |          |  | |||   |  |  ||   | ||  ||  |
 51 N-RKDQKHQHGSLR-NQGSR--FNIKVTHNLGDYYALGYYETRFI-N--          100

101 VQVKDQQGEVVREYEVEKL-GNNVHV---KRL-YAGFAY-EGLGTLTFGN          150
    ||  |     |   |  |       ||||    | ||   ||| |||
101 ---KDIDGN---E----KNIGSGFGSITTK-LAYAGLGNKE-LGEATFGL          150

151 QLTIGDDVGLS---DYTYFNSG-IN-NLLSSG--EK-AINF--KSAEFNG          200
    | ||  |      |  |   |  |  |      |  | ||   | |
151 QKTIADKI--STAEDKEY---GVIEKN--SYIPTEGNAIAYTYKGIE--G          200

201 FTFGGA-YVF-----SADA---D-KQ--ALRDGRGFV-VAGL-Y--NRKM          250
    | | |||       | |    |    |  |       | | | |
201 LTLG-ASYVFGGRNFS-DYEITDGKVSNA-------VQV-GAKYDANNI-          250

251 GDV-GFAFEAGYSQKYVK-QEVEQNPPAA-QKVFKDEKEKAFMVGAELSY          300
    | |||   |   | |   |    |  |       |  | |
251 --VAGFAY--GRTN-Y-KAQ---Q---AKTQQVNG-----AL---ATLGY          300

301 A----GLALGV-D--YAQSKVT-NV-DGK--KRALEV--GLNY----D--          350
       || |   |   |  ||   |   ||  ||    |  |        |
301 HFDDLGL-LISLDSGYA--K-TKNKAD-KHEKRYF-VSPGFQYELMEDTN          350

351 L--NDRAKVYTDFIWEKE-GPKGDVTRNRTVAVGFGY--KLHKQVETFVE          400
    |  |  ||  |  |     | |  |  || ||  |||||| | |
351 LYGNL--K-YER-INSVDQGEK--V-REH--AVLFGIDHKLHKQVLTYIE          400

401 -A-AWGREKDSDGVT--T-KNNVVGTGLRVHF.................          450
     |  |  |  ||  ||  |      || ||||| |
401 GAYARTRTNDK-GKTEKTEKEKSVGVGLRVYF..................          450
```

FIG. 5

```
                                    Signal Peptide
   1 ATG AAA AAG ACA ATC GTA GCA TTA GCA GTC GCA GCA GTA GCA GCA ACT TCA GCA AAC
   1▶Met Lys Lys Thr Ile Val Ala Leu Ala Val Ala Ala Val Ala Ala Thr Ser Ala Asn
  ─────────────────────────────────────────────────────────────────────────────
  58 GCC GCA ACA GTT TAC AAT CAA GAC GGT ACA AAA GTT GAT GTA AAC GGT TCT GTA CGT
  20▶Ala Ala Thr Val Tyr Asn Gln Asp Gly Thr Lys Val Asp Val Asn Gly Ser Val Arg
     ───
 115 TTA ATC CTT AAA AAA GAA AAA AAT GAG CGC GGT GAT TTA GTG GAT AAC GGT TCA CGC
  39▶Leu Ile Leu Lys Lys Glu Lys Asn Glu Arg Gly Asp Leu Val Asp Asn Gly Ser Arg
 172 GTT TCT TTC AAA GCA TCT CAT GAC TTA GGC GAA GGT TTA AGC GCA TTA GCT TAC GCG
  58▶Val Ser Phe Lys Ala Ser His Asp Leu Gly Glu Gly Leu Ser Ala Leu Ala Tyr Ala
 229 GAA CTT CGT TTC AGT AAA AAT GAG AAA GTA GAA GTG AAA GAT GCA CAA AAT CAA CAA
  77▶Glu Leu Arg Phe Ser Lys Asn Glu Lys Val Glu Val Lys Asp Ala Gln Asn Gln Gln
 286 GTA GTT CGT AAA TAT GAA GTT GAG CGT ATC GGT AAC GAT GTT CAT GTA AAA CGT CTT
  96▶Val Val Arg Lys Tyr Glu Val Glu Arg Ile Gly Asn Asp Val His Val Lys Arg Leu
 343 TAT GCG GGT TTC GCG TAT GAA GGT TTA GGA ACA TTA ACT TTC GGT AAC CAA TTA ACT
 115▶Tyr Ala Gly Phe Ala Tyr Glu Gly Leu Gly Thr Leu Thr Phe Gly Asn Gln Leu Thr
 400 ATC GGT GAT GAT GTT GGT GTG TCT GAC TAC ACT TAC TTC TTA GGT GGT ATC AAC AAC
 134▶Ile Gly Asp Asp Val Gly Val Ser Asp Tyr Thr Tyr Phe Leu Gly Gly Ile Asn Asn
 457 CTT CTT TCT AGC GGT GAA AAA GCA ATT AAC TTT AAA TCT GCA GAA TTC AAC GGT TTC
 153▶Leu Leu Ser Ser Gly Glu Lys Ala Ile Asn Phe Lys Ser Ala Glu Phe Asn Gly Phe
 514 ACA TTT GGT GGT GCG TAT GTG TTC TCA GCG GAT GCT GAC AAA CAA GCA CCA CGT GAT
 172▶Thr Phe Gly Gly Ala Tyr Val Phe Ser Ala Asp Ala Asp Lys Gln Ala Pro Arg Asp
 571 GGT CGC GGT TTC GTT GTA GCA GGT TTA TAC AAC AGA AAA ATG GGC GAT GTT GGT TTC
 191▶Gly Arg Gly Phe Val Val Ala Gly Leu Tyr Asn Arg Lys Met Gly Asp Val Gly Phe
 628 GCA CTT GAA GCA GGT TAT AGC CAA AAA TAT GTA ACA GCA GCA GCT AAA CAA GAA AAA
 210▶Ala Leu Glu Ala Gly Tyr Ser Gln Lys Tyr Val Thr Ala Ala Ala Lys Gln Glu Lys
 685 GAA AAA GCC TTT ATG GTT GGT ACT GAA TTA TCA TAT GCT GGT TTA GCA CTT GGT GTT
 229▶Glu Lys Ala Phe Met Val Gly Thr Glu Leu Ser Tyr Ala Gly Leu Ala Leu Gly Val
 742 GAC TAC GCA CAA TCT AAA GTG ACT AAC GTA GAA GGT AAA AAA CGC GCA CTT GAA GTA
 248▶Asp Tyr Ala Gln Ser Lys Val Thr Asn Val Glu Gly Lys Lys Arg Ala Leu Glu Val
 799 GGT TTA AAC TAT GAC ATT AAT GAC AAA GCA AAA GTT TAC ACT GAC TTG ATT TGG GCA
 267▶Gly Leu Asn Tyr Asp Ile Asn Asp Lys Ala Lys Val Tyr Thr Asp Leu Ile Trp Ala
 856 AAA GAA GGT CCA AAA GGT GCG ACT ACA AGA GAT CGT TCT ATC ATC TTA GGT GCG GGC
 286▶Lys Glu Gly Pro Lys Gly Ala Thr Thr Arg Asp Arg Ser Ile Ile Leu Gly Ala Gly
 913 TAC AAG CTT CAC AAA CAA GTT GAA ACC TTT GTT GAA GGT GGC TGG GGC AGA GAG AAA
 305▶Tyr Lys Leu His Lys Gln Val Glu Thr Phe Val Glu Gly Gly Trp Gly Arg Glu Lys
 970 GAT GCT AAT GGC GTA ACA ACA AAA GAT AAC AAA GTT GGT GTT GGT TTA CGC GTA CAC
 324▶Asp Ala Asn Gly Val Thr Thr Lys Asp Asn Lys Val Gly Val Gly Leu Arg Val His
1027 TTC TAA
 343▶Phe ···
```

FIG. 11

```
  1 ATVYNQDGTKVDVNGSVRLILKKEKNERGDLVDNGSRVSFKASHDLGEGL         50
    |||||||||||||||||| |||||||||||||||||||||||||||||||
 21 ATVYNQDGTKVDVNGSLRLILKKEKNERGDLVDNGSRVSFKASHDLGEGL         70

51 SALAYAELRFSKNEKVEVKDAQNQQ-VVRKYEVERIGNDVHVKRLYAGFA        100
    ||||| |||||||  | ||| |    ||| |||| |  ||||||||||||
 71 SALAYTELRFSKNVPVQVKD-Q-QGEVVREYEVEKLGNNVHVKRLYAGFA        120

101 YEGLGTLTFGNQLTIGDDVGVSDYTYFLGGINNLLSSGEKAINFKSAEFN        150
    ||||||||||||||||||||| ||||| |  |||||||||||||||||||
121 YEGLGTLTFGNQLTIGDDVGLSDYTYFNSGINNLLSSGEKAINFKSAEFN        170

151 GFTFGGAYVFSADADKQAPRDGRGFVVAGLYNRKMGDVGFALEAGYSQKY        200
    |||||||||||||||||| |||||||||||||||||||||| ||||||||
171 GFTFGGAYVFSADADKQALRDGRGFVVAGLYNRKMGDVGFAFEAGYSQKY        220

201 VTA-------AA-KQ---EKEKAFMVGTELSYAGLALGVDYAQSKVTNVE        250
     |        || |    ||||||||| |||||||||||||||||||||
221 VKQEVEQNPPAAQKVFKDEKEKAFMVGAELSYAGLALGVDYAQSKVTNVD        270

251 GKKRALEVGLNYDINDKAKVYTDLIWAKEGPKGATTRDRSIILGAGYKLH        300
    |||||||||||||| || |||||| || ||||| ||  |    | |||||
271 GKKRALEVGLNYDLNDRAKVYTDFIWEKEGPKGDVTRNRTVAVGFGYKLH        320

301 KQVETFVEGGWGREKDANGVTTKDNKVGVGLRVHF...............        350
    ||||||||  ||||||  ||||| | || ||||||
321 KQVETFVEAAWGREKDSDGVTTKNNVVGTGLRVHF...............        370
```

FIG. 12

FIG. 15

```
              1                                  50                                        100
Serotype 8    ATVYNQDGTT VDVNGSVRLL LKKEKDMRGD LIDNG...... SRVSEKASHD LEEGLSALGY AELRESDDVK DKDGNVVNQP .......... IGNKVHAKRL
Serotype 9    ATVYNQDGTK VDVNGSVRLL LKKEKNERGD LVDNG...... SRVSEKASHD LEEGLSALAY AELRESTKEK VEVKDIQNQQ QVVRTYEVEK IGNDVHVKRL
ECOOMPF       AEIYNKDGNK VDLYGKAVGL HIFSKGNGEN SYGNGDMTY ARLGEKGEIQ INSDLIGYGQ M

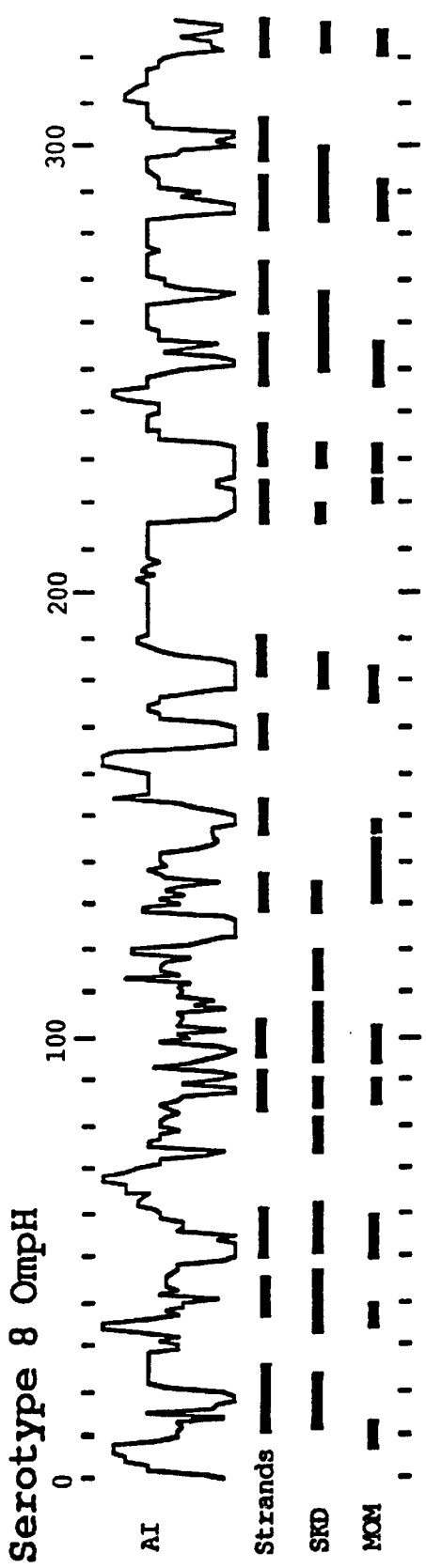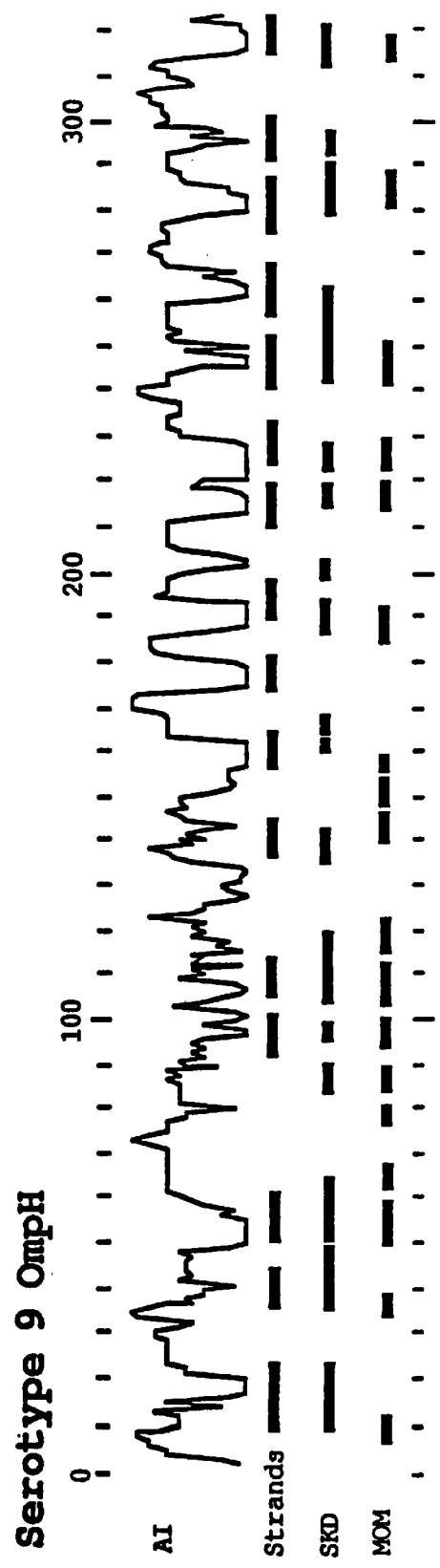
FIG. 18

| Amino Acid | Codon |
|---|---|
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

FIG. 19

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

FIG. 20

DNA ENCODING THE OUTER MEMBRANE PROTEIN OF *PASTEURELLA MULTOCIDA*

CROSS-REFERENCE TO RELATED APPLICATIONS

This application is a utility patent application claiming priority from provisional application No. 60/067,957, filed Dec. 8, 1997, the disclosure of which is incorporated by reference herein.

BACKGROUND OF THE INVENTION

Fowl cholera is a severe respiratory disease in domestic poultry and wild birds. This disease occurs throughout the year and causes great losses in the poultry industry around the world (Rhoades et al., 1989). Fowl cholera has two clinical forms, acute disease and chronic disease. The acute disease is a septicemia with high morbidity and mortality. Clinical signs of the acute disease include fever, anorexia, ruffled feathers, mucous discharge from the mouth, diarrhea, increased respiratory rate and cyanosis. Death may be the first evidence of the acute disease. The chronic form of fowl cholera is characterized by localized infections including swelling in wattles, sinuses, periorbital subcutaneous tissues, leg or wing joints, sternal bursae and foot pads, exudative conjunctivitis, pharyngitis, emaciation and lethargy (Rhoades et al., 1991; Rhoades et al., 1989).

*Pasteurella multocida* is the causative agent of fowl cholera. Almost all types of birds including chickens, turkeys, ducks and geese are susceptible to *P. multocida* infection. In addition to causing fowl cholera in birds, *P. multocida* also causes disease in mammals, including cattle, swine, horses, sheep, goats, rabbits and humans. Differences in the capsule antigen are employed to classify *P. multocida* into serogroups, i.e., serogroups A, B, D, E and F (Carter et al., 1955; Rimler et al., 1987). Differences in lipopolysaccharide antigen are used to subtype the bacteria into 16 somatic serotypes (Brogden et al., 1978; Heddleston et al., 1992). Most of the avian isolates are serotype A: 1, A:3, and A:4 (Hofacre et al., 1986).

Current control of fowl cholera mainly relies on vaccination. Two kinds of vaccines are used in poultry, the inactivated vaccines (bacterins) and attenuated live vaccines. However, a bacterin induces only homologous, i.e., serotype-specific, protection. As there are currently 16 somatic serotypes, the efficacy of bacterins is very limited. While live vaccines such as those which employ the CU, PM-1 and M-9 strains, can induce heterologous immunity, they can induce disease (Carpenter et al., 1988; Hofacre et al., 1989a; Hofacre et al., 1989b; Hofacre et al., 1986; Schlink et al., 1987a; Schlink et al., 1987b).

The outer membrane of Gram-negative bacteria contains a number of components: phospholipid layer, outer membrane proteins (OMP), and lipopolysaccharide (LPS). The outer membrane contains a number of proteins including major outer membrane porins and other proteins. There are reports that *P. multocida* outer membrane protein was able to induce protective immunity in poultry and other animals (Lu et al., 1991a; Lu et al., 1991b; Lu et al., 1988a; Lu et al., 1988b; Ruffolo et al., 1996; Zhao et al., 1995). Moreover, it has been reported that outer membrane proteins expressed by in vivo grown bacteria induced cross-protection in poultry (heterologous protection) (Rimler et al., 1994; Wang et al., 1994a; Wang et al., 1994b).

Thus, what is needed is the identification and isolation of the gene encoding the major outer membrane protein of *P. multocida*. Moreover, there is a need for improved immunogenic compositions useful to prevent or inhibit fowl cholera.

SUMMARY OF THE INVENTION

The invention provides an isolated and purified nucleic acid molecule comprising a preselected nucleic acid sequence which encodes an avian *Pasteurella multocida* outer membrane protein or polypeptide (OmpH), a biologically active subunit or a biologically active variant thereof. Preferably, the nucleic acid molecule of the invention encodes a porin. Porins are major outer membrane proteins which have pore-forming function. They serve as molecular sieves allowing polar solutes to pass through but excluding non-polar molecules of comparable sizes. As described hereinbelow, the genes (ompH) encoding OmpHs from all 16 *P. multocida* serotypes were cloned and sequenced. The OmpHs from different serotypes showed high homology in amino acid sequence (72.3% overall identity). Computer-aided secondary structure predictions revealed 16 antiparallel beta-strands connected by 8 external loops and 8 short periplasmic turns. Preferred isolated nucleic acid molecules of the invention include those having a nucleic acid sequence comprising SEQ ID NO:1 or SEQ ID NO:3, molecules encode a polypeptide having an amino acid sequence such as SEQ ID NO:2, SEQ ID NO:4, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42 or SEQ ID NO:43. The nucleic acid molecules of the invention, subunits or variants thereof, are useful to prepare probes, primers or expression cassettes which, in turn, are useful to detect, amplify and express other ompH genes and related genes.

Therefore, the invention also provides an expression cassette comprising: a preselected DNA sequence which is operably linked to a promoter functional in a host cell, which DNA sequence encodes a *Pasteurella multocida* outer membrane polypeptide, a biologically active subunit or a biologically active variant thereof. The host cell may be prokaryotic or eukaryotic in origin. Preferably, the preselected DNA sequence comprises SEQ ID NO:1 or SEQ ID NO:3, or the complement thereto. Also preferably, the preselected DNA segment encodes a polypeptide having an amino acid sequence such as SEQ ID NO:2, SEQ ID NO:4, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, or a fragment thereof. These cassettes may be employed to prepare recombinant polypeptides. For example, a nucleic acid molecule of the invention, a variant or a fragment thereof, e.g., an expression cassette of the invention, may be introduced and expressed in a cultured host cell, preferably a host cell that is stably transformed with the nucleic acid molecule, so as to yield recombinant *Pasteurella multocida* outer membrane polypeptide, a biologically active subunit, variant or derivative thereof. Preferably, the recombinant polypeptide is recovered from the host cell. The recombinant polypeptide may be recovered from cell lysates in a soluble fraction, i.e., the recombinant OmpH is not associated with membranes, in the insoluble fraction, or from supernatants, i.e., the recombinant polypeptide is secreted into the extracellular environment of the host cell. As described herein, the genes encoding mature OmpH polypeptides of *Pasteurella multocida* strains X-73 and P-1059 were expressed as fusion proteins in *Escherichia coli*. Thus, another embodiment of the invention is a fusion polypeptide comprising at least an immunogenic or antigenic portion of the *Pasteurella multocida* outer membrane polypeptide.

Yet another embodiment of the invention is isolated and purified native *Pasteurella mullocida* outer membrane protein, which native polypeptide is obtained from a particular isolate or strain of *Pasteurella multocida*. As shown hereinbelow, the major outer membrane proteins of *Pasteurella multocida* strains X-73 and P-1059 were purified by selective extraction with detergents and size exclusion chromatography. The planar lipid bilayer assay showed that the isolated and purified native OmpH of X-73 and P-1059 had pore-forming activity. Thus, a preferred embodiment of the invention is isolated and purified *Pasteurella multocida* strain X-73 outer membrane protein, a biologically active subunit, variant or derivative thereof. Another preferred embodiment is isolated and purified *Pasteurella multocida* strain P-1059 outer membrane porin protein, a biologically active subunit, variant or derivative thereof.

The invention also provides an isolated and purified peptide of the *Pasteurella multocida* outer membrane polypeptide, a biologically active variant or derivative thereof. Preferably, a peptide of the invention corresponds to extracellular domains of *Pasteurella multocida* outer membrane polypeptide. More preferably, a peptide of the invention is modified so as to yield a derivative of the peptide, e.g., a cyclized peptide. A peptide or peptide variant of the invention is useful in assays to detect antibodies specific for the peptide or for a polypeptide, a portion of which has an amino acid sequence corresponding to an epitope within the peptide. A peptide or peptide variant of the invention is also useful in an immunogenic composition to prepare antisera or vaccines.

A vaccine of the invention comprises an amount of isolated and purified *Pasteurella multocida* outer membrane protein, polypeptide, a subunit, a fragment (e.g., a peptide), a variant, a derivative, or a combination thereof, effective to immunize a susceptible vertebrate, e.g., a bovine, swine, equine, ovine, caprine, rabbit, human or avian, preferably in combination with a carrier vehicle. Preferably, the polypeptide is the outer membrane polypeptide of strain X-73 or P-1059 of *Pasteurella multocida*. Protection studies described herein showed that isolated and purified X-73 outer membrane polypeptide induced homologous protection in chickens.

Also provided is a vaccine comprising an amount of a peptide of the outer membrane polypeptide of *Pasteurella multocida*, a variant, a derivative, or a combination thereof, effective to immunize a susceptible vertebrate, optionally in combination with a carrier vehicle. A peptide vaccine of the invention preferably provides homologous protection, and more preferably heterologous protection, i.e., protection against at least two different serotypes. Preferred peptides of the invention useful to prepare vaccines or immunogenic compositions correspond to extracellular sequences, e.g., from loop 2, of the outer membrane polypeptide. Protection studies showed that a synthetic cyclic peptide derived from the predicted largest loop (loop 2) of X-73 outer membrane polypeptide, i.e., a peptide comprising SEQ ID NO:45, induced homologous protection in chickens. In contrast, synthetic linear peptides of loop 2 and loop 5 of X-73 outer membrane polypeptide did not provide protection in chickens against homologous challenge. Thus, it is envisioned that a mixture of peptides, preferably cyclic peptides, may induce broad protection, i.e., heterologous protection, against *Pasteurella multocida* infection. Moreover, it is envisioned that any of the immunogenic compositions of the invention may be employed in combination with bacterins.

Further provided is an immunogenic composition comprising an effective amount of an isolated and purified *Pasteurella multocida* outer membrane polypeptide, e.g., X-73 or P-1059 polypeptide, a subunit, a peptide, a variant, a derivative, or a combination thereof, in combination with a pharmaceutically acceptable carrier, such as an injectable or ingestible liquid carrier, wherein the administration of the immunogenic composition to a vertebrate induces the production of antibodies specific for *Pasteurella multocida* outer membrane porin polypeptide.

The invention further provides a method for detecting or determining the presence antibodies which are specific for avian *Pasteurella multocida* in a vertebrate physiological sample. The method comprises contacting an amount of purified immunogenic protein (native), polypeptide (recombinant), peptide or variant thereof, encoded by the genomic nucleic acid of *Pasteurella multocida* with the physiological sample which comprises antibodies suspected of specifically reacting with *Pasteurella multocida*, for a sufficient time to form binary complexes between at least a portion of the antibodies and an antigenic or immunogenic portion of the purified protein or polypeptide. Then the presence or amount of the complexes is detected or determined. Alternatively, isolated cells of *Pasteurella multocida*, such as a lysate from, for example, strain X-73 or P-1059, can be employed as the immunogenic material that is contacted with the physiological sample to be tested. Thus, the invention also provides kits useful to detect or determine the presence of antibodies that specifically react with an infectious agent which is associated with fowl cholera. Such a kit may comprise packaging, containing, separately packaged: (a) a solid phase capable of immobilizing a polypeptide; and (b) a known amount of a purified recombinant polypeptide or peptide which specifically reacts with antibodies specific for the agent, wherein the amino acid sequence of the polypeptide or peptide is identical to at least a portion of the sequence of the outer membrane polypeptide of *Pasteurella multocida*, or a variant thereof.

Also provided is a method for detecting nucleic acid encoding an immunogenic polypeptide associated with the causative agent of fowl cholera. The method comprises contacting an amount of nucleic acid obtained from a vertebrate physiological sample which comprises cells suspected of containing nucleic acid encoding the immunogenic polypeptide, with an amount of at least two oligonucleotides under conditions effective to amplify the nucleic acid so as to yield an amount of amplified nucleic acid. Methods to amplify nucleic acid are well known to the art. A sample of RNA may be transcribed to DNA by reverse transcription of RNA from the physiological sample. At least one oligonucleotide is specific for the nucleic acid encoding an outer membrane polypeptide of *Pasteurella multocida*. The presence of the amplified nucleic acid is then detected or determined. Preferably, amplified DNA is subjected to agarose gel electrophoresis prior to detection. Thus, the invention also provides a diagnostic kit for detecting the presence of DNA associated with fowl cholera in a sample. The kit comprises packaging containing (a) a known amount of a first oligonucleotide, wherein the first oligonucleotide consists of at least about 7 to about 50, preferably at least about 12 to about 40 nucleotides, and even more preferably about 15 to about 25 nucleotides, and wherein the oligonucleotide has at least about 70% contiguous sequence identity to a nucleic acid molecule of the invention, e.g., SEQ ID NO:1, and (b) a known amount of a second oligonucleotide, wherein the second oligonucleotide consists of at least about 7 to about 50, preferably at least about 12 to about 40 nucleotides, and even more preferably about 15 to about 25 nucleotides, and wherein the oligonucleotide has at least about 70% contiguous sequence identity to a nucleotide sequence which is complementary to a nucleic acid molecule of the invention, e.g., SEQ ID NO:1.

Yet another embodiment of the invention is a diagnostic method. The method comprises contacting an amount of DNA obtained from a physiological sample which comprises cells from a bird at risk of or afflicted with fowl cholera, or a vertebrate exposed to said bird, with an amount of at least two oligonucleotides that bind to complementary strands of said DNA at preselected regions under conditions effective to amplify the DNA, e.g., by a polymerase chain reaction, so as to yield an amount of amplified DNA. Alternatively, the DNA may be obtained by reverse transcription of RNA from the physiological sample. At least one of the oligonucleotides is specific for DNA encoding an outer membrane polypeptide of Pasteurella multocida. Then the presence of amplified DNA is detected or determined. The presence of amplified DNA is indicative of a bird infected with *Pasteurella multocida*, or afflicted with or at risk of fowl cholera, or a vertebrate exposed to said bird.

Yet another embodiment of the invention is an isolated antibody or a preparation thereof obtained from a vertebrate exposed to an immunogenic composition or vaccine of the invention wherein the preparation comprises antibodies that bind the infectious agent that is associated with fowl cholera. Preferably, the preparation is obtained from a chicken or a turkey. More preferably, the preparation binds to more than one serotype of the infectious agent. The preparations of antibodies of the invention are useful in assays, such as those described above, or to provide passive immunity to a vertebrate to which the preparation is administered.

Also provided is a method to prevent or inhibit fowl cholera, comprising: immunizing a bird with an effective amount of isolated or purified *Pasteurella multocida* outer membrane polypeptide, e.g., from strain X-73 or P-1059, a variant, a subunit (e.g., a peptide), a derivative, or a combination thereof. Preferably, the avian is immunized with a peptide of the invention, a variant, a derivative, or a combination thereof. Thus, the invention further provides an immunized bird, such as a turkey or chicken, i.e., that is resistant to infection by fowl cholera.

BRIEF DESCRIPTION OF THE FIGURES

FIG. 1. SDS-PAGE and Western blot assay of native X-73 OmpH from *P. multocida* and recombinant X-73 OmpH from *E. coli*. (A) SDS-PAGE analysis of purified native X-73 OmpH and recombinant X-73 OmpH on a 10% gel, stained with Coomassie blue. (B) Western blot of the gel in (A) probed with antiserum against X-73 bacterin. (C) Western blot of the gel in (A) probed with anti-serum against recombinant protein. Lanes in (A), (B), and (C): 1, boiled X-73 whole cell lysate; 2, 37° C. incubated X-73 whole cell lysate; 3, 37° C. incubated purified X-73 OmpH; 4, boiled purified X-73 OmpH; 5, whole cell lysate of XLI-Blue MRF' harboring pJYH1, IPTG uninduced; 6, whole cell lysate of XLI-Blue MRF' harboring pJYHI, IPTG induced (10 hours); 7, purified recombinant X-73 OmpH; 8, whole cell lysate of XLI-Blue MRF' harboring pQE32 without insert, IPTG uninduced; and 9, whole cell lysate of XL I-Blue MRF' harboring pQE32 without insert, IPTG induced (10 hours). Samples in lanes 5–9 were boiled before loading. Numbers on the left indicate the position of molecular weight standard (kDa).

FIG. 2. Southern blot analysis of restriction enzyme digests of X-73 genomic DNA probed with oligonucleotide N (SEQ ID NO:5). Lanes: 1, molecular markers; 2, HindIII digests; 3, Sau3A1 digests; and 4, TaqI digests. Numbers on the left indicate molecular sizes in kilobases.

FIG. 3. Agarose gel electrophoresis of the PCR products amplified from X-73 genomic DNA library. Lanes: 1, molecular size markers; 2, PCR products when primer A (SEQ ID NO:6) and primer D (SEQ ID NO:7) were employed; and 3, PCR products when primer B (SEQ ID NO:8) and primer D (SEQ ID NO:7) were employed. Numbers on the left indicate molecular sizes in kilobases.

FIG. 4. The DNA sequence of the omph gene of X-73. The predicted amino acid sequence (SEQ ID NO:2) is shown under the DNA sequence (SEQ ID NO:1), with the signal peptide indicated. The putative promoter sequence (−35 and −10), the ribosome binding site (RBS) and the inverse repeat are shown, as are the HindIII, Sau3A1 and TaqI sites.

FIG. 5. Comparison of the amino acid sequences of *P. multocida* X-73 OmpH (SEQ ID NO:2) (upper) and *H. influenzae* porin P2 (SEQ ID NO:9) (lower). Identity is indicated by the solid vertical line.

FIG. 6. Dot blot of genomic DNA from *P. multocida* 15 somatic serotypes, as well as the CU vaccine strain. The blotting was processed under high stringency conditions. Lanes in row (A): 1, X-73; 2, P-1059; 3, P-1662; 4, P-1702; 5, Serotype 6; 6, Serotype 7; 7, Serotype 8; and 8, Serotype 9. Lanes in row (B): 1, Serotype 10; 2, Serotype 11; 3, Serotype 12; 4, Serotype 13; 5, Serotype 14; 6, Serotype 15; 7, Serotype 16; and 8, CU strain.

FIG. 7. Western blots of whole cell lysates of 15 serotypes of *P. multocida* and CU strain probed with antiserum against recombinant OmpH. Lanes in (A): 1, X-73; 2, P-1059; 3, P-1662; 4, P-1702; S, Serotype 6; 6, Serotype 7; 7, Serotype 8; 8, Serotype 9; and 9, Serotype 10. Lanes in (B): 1, Serotype 11; 2, Serotype 12; 3, Serotype 13; 4, Serotype 14; 5, Serotype 15; 6, Serotype 16; and 7, CU strain. Numbers on the left indicate the position of molecular weight standard (kDa).

FIG. 8. Chart recording of the stepwise increase in conductance caused by the addition of purified X-73 OmpH to the aqueous phase (1 M KCl) bathing a lipid bilayer membrane made from 1.5% oxidized cholesterol in n-decan. The applied voltage was 50 mV. The X axis was chart speed with 5 cm/minute. The y axis was volts with 200 mV/unit (the vertical bar on the right side).

FIG. 9. Histogram of conductance steps in 1.0 M KCl. The membrane was made with 1.5% oxidized cholesterol in n-decane over a hole of 0.1 $mm^2$ separating the two aqueous compartments. Purified X-73 OmpH was added to one compartment and 50 mV voltage was applied. The total number of conductance steps examined was 100. The average single channel conductance was 0.62.

FIG. 10. SDS-PAGE and Western blot analysis of 35 kDa of native OmpH *P. multocida* P-1059 and recombinant P-1059 OmpH expressed in *E. coli*. (A) PAGE of the whole cell lysates and purified polypeptides on a 10% polyacrylamide gel, stained with Coomassie blue. (B) Western blot of the gel in (A) probed with antiserum against *P. multocida* P-1059 bacterin. Lanes in (A) and (B): 1, whole cell lysate of *P. multocida* P-1059, boiled; 2, whole cell lysate of *P. multocida* P-1059, not boiled; 3, purified 35 kDa major outer membrane protein; 4, XLI-Blue MRF' harboring pJYH3 uninduced; 5, XLI-Blue MRF', harboring pJYH3 induced (10 hours); 6, purified recombinant OmpH; 7, XLI-Blue MRF' harboring pQE32 without insert, uninduced; and 8, XLI-Blue MRF' harboring pQE32 without insert, induced (10 hours). Lanes 3–8 in (A) and (E) were boiled. Numbers on the left indicate the position of molecular weight standard (kDa).

FIG. 11. The DNA sequence of the *P. multocida* P-1059 omph gene (SEQ ID NO:3). The predicted amino acid sequence (SEQ ID NO:4) is shown under the DNA sequence, with the signal peptide indicated.

FIG. 12. Comparison of the amino acid sequence of *P. multocida* P-1059 OmpH (SEQ ID NO:4; upper sequence) with that of *P. multocida* X-73 OmpH (lower sequence) (SEQ ID NO:2).

Figure 13:
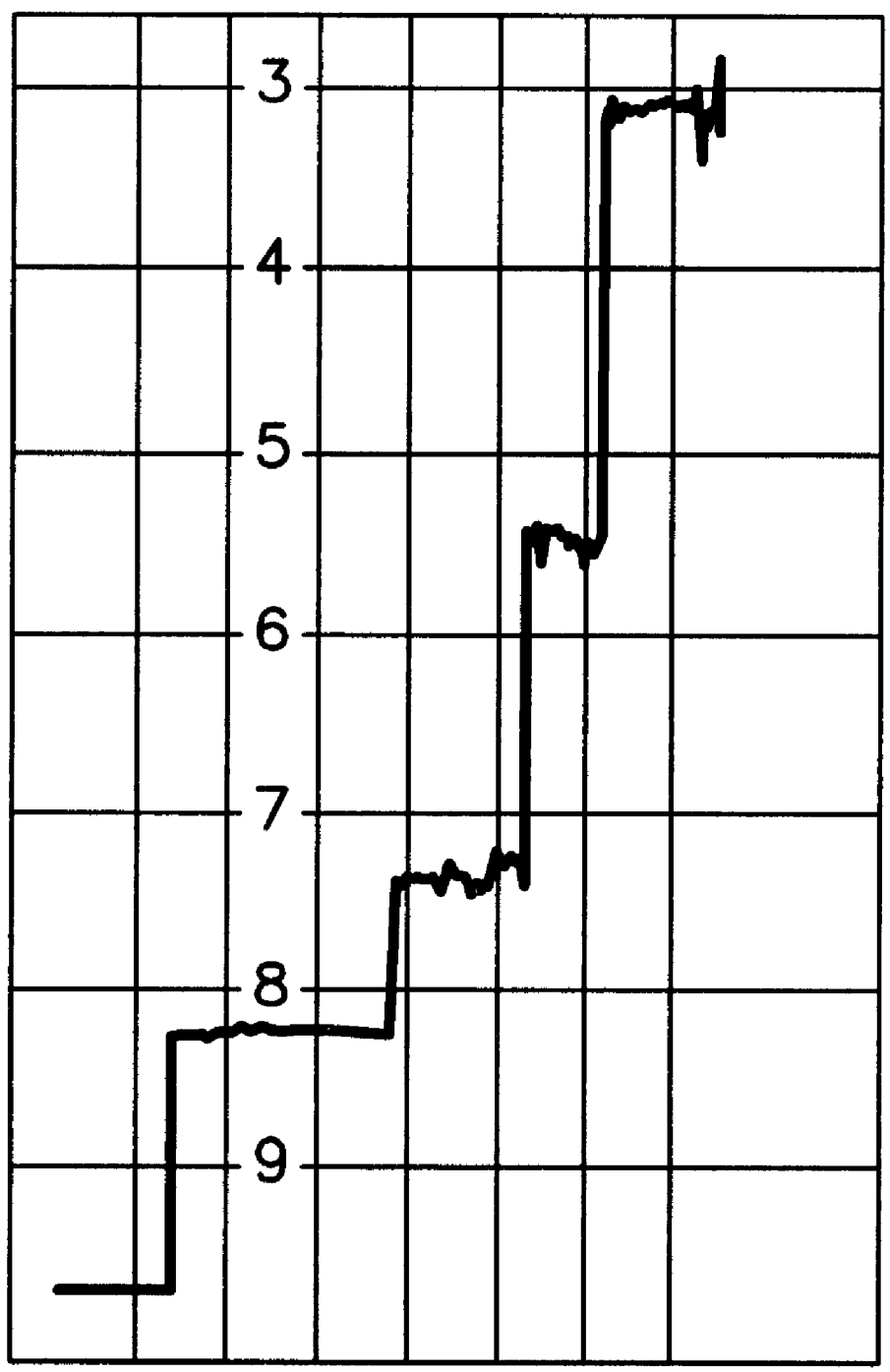

FIG. 13. Chart recording of the stepwise increase in conductance caused by the addition of purified 35 kDa OmpH of P-1059 to the aqueous phase (1 M KCl) bathing a lipid bilayer membrane made from 1.5% oxidized cholesterol in n-decan. The applied voltage was 50 mV. The X axis was chart speed with 5 cm/minute. The y axis was volts with 100 mV/unit (the vertical bar on the right side).

Figure 14:
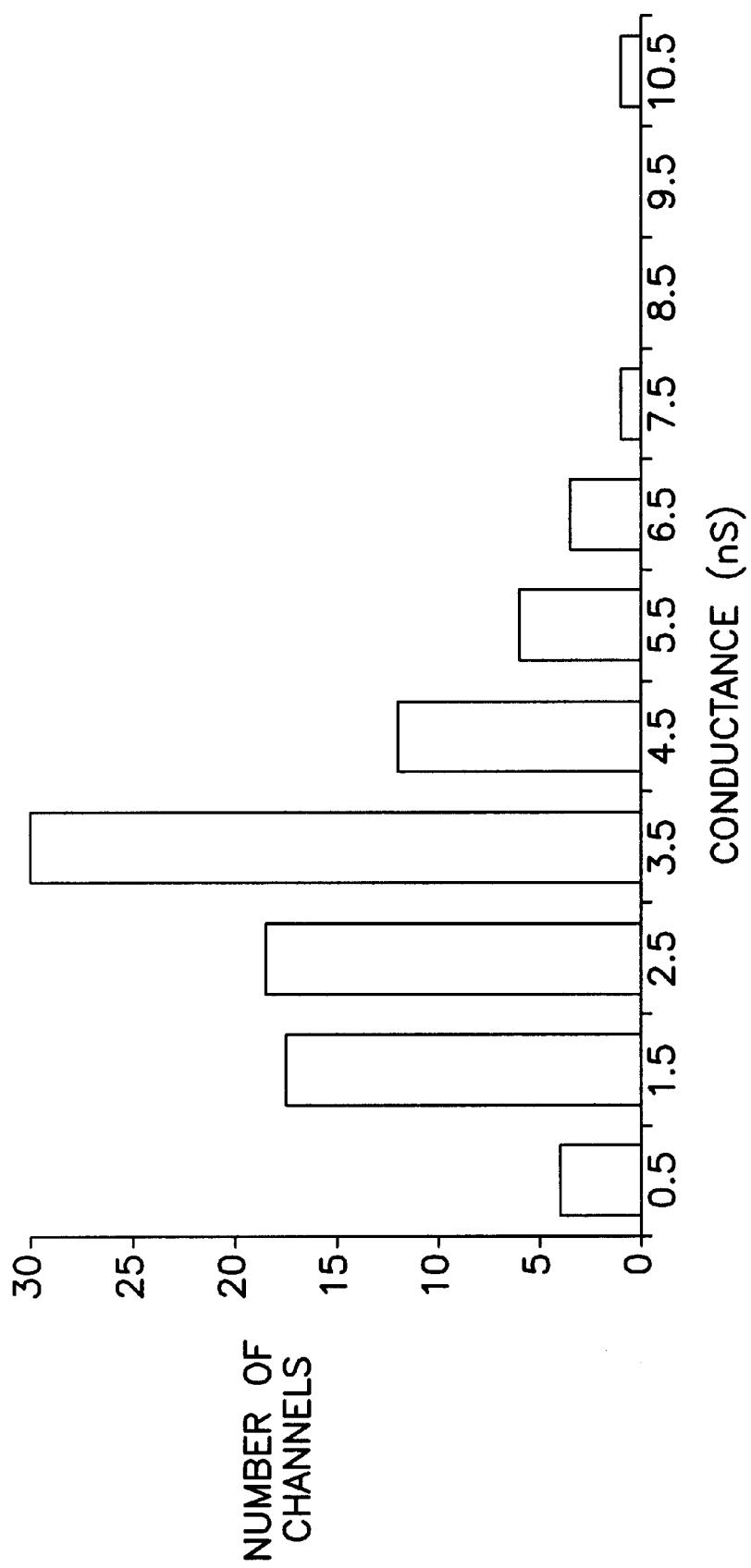

FIG. 14. Histogram of conductance steps in 1.0 M KCl. The membrane was made with 1.5% oxidized cholesterol in n-decan over a hole of 0.1 mm² separating the two aqueous compartments. Purified 35 kDa OmpH of P-1059 was added to one compartment and 50 mV voltage was applied. The total number of conductance steps examined was 91. The average single channel conductance was 0.67.

FIG. 15. Deduced amino acid sequences, multiple sequence aligniept and predicted secondary structures of *P. multocida* OmpHs. Identities of amino acids are boxed in black and conserved amino acid substitutions are boxed in gray, respectively. S1–S16 (bars) indicate the predicted antiparallel beta-strands, L1–L8 inmicate the predicted external loops, and T1–T8 indicate the predicted periplasmic turns. Serotvpe 1 is SEQ ID NO:59, Serotvoe 3 is SEQ BD NO:60. Cu strain is SEQ TD NO:61. Serotype 4 is SEQ ID NO:31. Serotype 5 is SEQ ID NO:32, Serotype 6 is SEQ ID NO:33. Serotype 7 is SEQ ID NO:34. Serotype 8 is SEQ ID NO:35, Serotyne 9 is SEQ ID NO:36. Serotype 10 is SEQ ID NO:37. Serotype 11 is SEQ ID NO:38. Serotype 12 is SEQ ID NO:39. Serotype 13 is SEQ ID NO:40 Serotype 14 is SEQ ID NO:41, Serotye 5 is SEQ ID NO:42 and Serotype 16 is SEQ ED NO:43.

Figure 16:
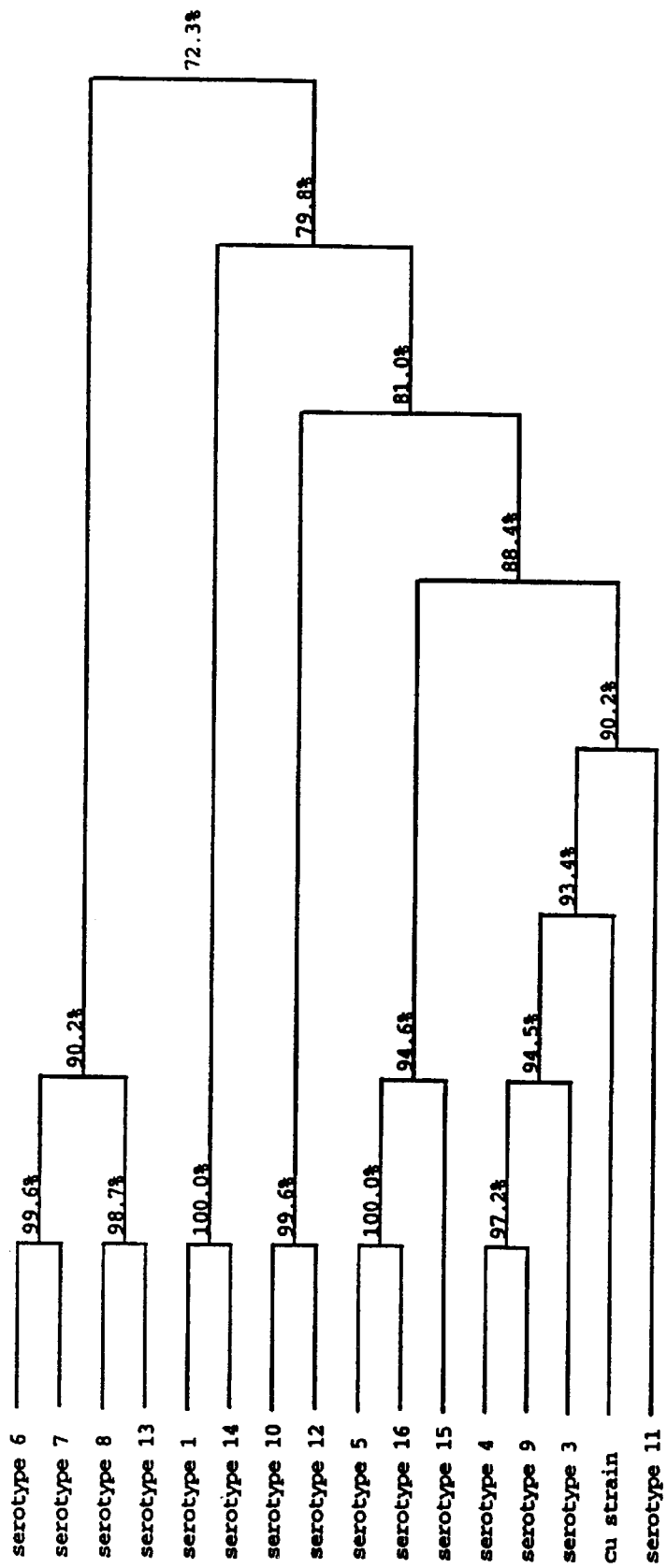

FIG. 16. Phylogenetic tree of omphs of 15 *P. multocida* serotypes and the CU strain.

FIG. 17. Multiple sequence alignment of serotype 8 and serotype 9 OmpHs with porins of *R. capsulatus* (RCAPORfN), *R. blastica* (RELASTICA), and *E. coli* (ECOOMPF; ECOPHOE). The beta-strands of the four porins with known crystal structure and the predicted beta-strands of serotype 8 and serotype 9 OmpHs are indicated by bars (S1–S16) under the sequences.

FIG. 18. Correlation of sided beta-sheet amphiphilicity index (SKD), hydrophobic moment and antigenic index (AI) profiles of serotype 8 OmpH (upper part) and serotype 9 OmpH (lower part) with their predicted beta-strands by sequence alignment (Strands). The predicted beta-strands are indicated by horizontal bars. The numbers indicate the amino acid positions. The vertical short bars indicate 10 amino acid intervals.

FIG. 19. Codons for specified amino acids.

FIG. 20. Exemplary and preferred amino acid substitutions for variant peptides or polypeptides of the invention.

DETAILED DESCRIPTION OF THE INVENRTION

Definitions As used herein, a "peptide" of the OmpH of *Pasteurella multocida* refers to a peptide which comprises no more than 75, preferably about 10 to about 50, and more preferably about 20 to about 40, peptidyl residues which have 100% contiguous amino acid sequence homology or identity to the amino acid sequence of a particular outer membrane polypeptide of an isolate of avian *Pasteurella multocida*. For example, a preferred peptide of the invention is a peptide of the OmpH of *Pasteurella multocida* X-73 which forms an exposed loop on the outer surface of *Pasteurella multocida* and, relative to other isolates, is of varied sequence and/or length. Preferably, peptides of the invention are homologous to regions having both variations in sequence and length, e.g., loop 2 or loop 5 (see FIG. 15), and which are immunogenic. Also preferably, the peptide corresponds to a region which comprises subtype specific, or non-subtype specific, epitopes useful for homologous, or heterologous, respectively, protection. Preferably, the epitopes are B-cell and T-cell epitopes. A preferred peptide of the invention corresponds to SEQ ID NO:45, a subunit or a derivative thereof.

An alignment of the amino acid sequences of the outer membrane polypeptide of *Pasteurella multocida* isolates, such as the alignment depicted in FIG. 15, provides a general method to identify the location of peptides within the scope of the invention. Moreover, it is envisioned that peptides within the scope of the invention may comprise moieties other than the amino acid sequences which are derived from the outer membrane polypeptide of *Pasteurella multocida*, e.g., amino acid residues not present in the native OmpH of *Pasteurella multocida* (i.e., a fusion protein), nucleic acid molecules or targeting moieties such as antibodies or fragments thereof, so long as these moieties do not substantially reduce the biological activity of the peptide. A substantial reduction in activity means a reduction in activity of greater than about 99%. Peptide variants include peptides having at least one D-amino acid.

An isolated "variant" of a peptide of the invention is a peptide comprising no more than 75, preferably about 10 to about 50, and more preferably about 20 to about 40, peptidyl residues which have at least 50%, preferably at least about 80%, and more preferably at least about 90%, but less than 100%, contiguous amino acid sequence homology or identity to the amino acid sequence of the corresponding native peptide of a wild type OmpH of *Pasteurella multocida*.

Likewise, a "variant" polypeptide of OmpH is a polypeptide having at least 50%, preferably at least about 80%, and more preferably at least about 90%, but less than 100%, contiguous amino acid sequence homology or identity to the amino acid sequence of the corresponding native wild type OmpH of a particular isolate of *Pasteurella multocida*. A variant polypeptide of the invention may include amino acid residues not present in the corresponding wild type native OmpH, and internal deletions relative to the corresponding wild type native OmpH. Polypeptide variants include polypeptides having at least one D-amino acid.

Polypeptides, peptides or variants thereof which are subjected to chemical modifications, such as esterification, amidation, reduction, protection and the like, are referred to as "derivatives." For example, a modification known to improve the immunogenicity, stability and/or bioavailability of peptides in vivo is the cyclization of the peptide, for example through one or more disulfide bonds. One such modification is the synthesis of a cyclic reverse sequence derivative (CRD) of a peptide of the invention. A linear peptide is synthesized with all D-form amino acids using the reverse (i.e., C-terminal to N-terminal) sequence of the peptide. If necessary, additional cysteine residues are added to the N and C termini (if the peptide sequence does not already have N and C terminal cys residues), thereby allowing oxidative cyclization. However, the term "CRD" includes cyclization by other mechanisms, e.g., via a peptidyl bond, and the like.

Also included within the scope of the term "derivative" is linear reverse D (LRD) and cyclized forward L (CFL)

derivatives. LRD derivatives have the reverse (i.e., C-terminal to N-terminal) sequence of the peptide with all D-form amino acids, but are not cyclized. CFL derivatives have the forward (i.e., N-terminal to C-termrinal) sequence of the peptide with all L-form amino acids, but with additional N and C terminal cys residues (if the peptide sequence does not already have cys residues at either the N or the C terminal position), followed by oxidative cyclization, or cyclization by an alternative method. A preferred derivative of the invention is a cyclic derivative of SEQ ID NO:45.

An isolated "variant" nucleic acid molecule of the invention is a nucleic acid molecule which has at least 80%, preferably at least about 90%, and more preferably at least about 95%, but less than 100%, contiguous nucleotide sequence homology or identity to the nucleotide sequence of the corresponding wild type nucleic acid molecule, e.g., a DNA sequence comprising SEQ ID NO:1 or SEQ ID NO:3, which encodes an OmpH of P. multocida. Moreover, a variant nucleic acid molecule of the invention may include nucleotide bases not present in the corresponding wild type nucleic acid molecule, as well as internal deletions relative to the corresponding wild type nucleic acid molecule.

Preferably, the polypeptides and peptides of the invention are biologically active. For example, a "biologically active" peptide or variant thereof, or polypeptide or variant thereof, of the invention has at least about 1%, preferably at least about 10%, more preferably at least about 50%, and even more preferably at least about 90%, the activity of a peptide having, for example, SEQ ID NO:45, or a polypeptide comprising SEQ ID NO:2 or SEQ ID NO:4 The activity of polypeptide or peptide of the invention can be measured by methods well known to the art including, but not limited to, the ability of the polypeptide or peptide to be bound by antibodies specific for OmpH, the ability of the polypeptide or peptide thereof to elicit a sequence-specific immunologic response when the polypeptide or peptide is administered to an animal such as a bird or a mammal, e.g., rabbit, goat, bovine, sheep, rat or mouse, the correlation of fowl cholera with the presence of amino acid sequences in the affected host corresponding to at least a portion of the polypeptide, or, for isolated OmpH, the ability to form pores as measured by methods well known to the art (see, for example, Bangham et al., 1967, Luckey et al., 1980, Nikado et al., 1981, Nikado et al., 1983 (liposome swelling assay); Benz et al., 1978, and Ikeda et al., 1988 (planar lipid bilayer assay); Hein et al., 1987, Sonntag et al., 1988, Szelcman et al., 1983, (uptake of radiolabeled substrate); Sawai et al., 1977, Zimmermann et al., 1977 (β-lactamase activity in the periplasmic space); and Struyve et al., 1992 (antibiotic resistance)). Preferably, the immunologic response is a humoral response, i.e, antibody response, directed to a particular epitope on the polypeptide or peptide. More preferably, the presence of antibodies specific for that epitope correlates with the *P. multocida* infection status of the organism.

As used herein, the terms "isolated and/or purified" refer to in vitro preparation, isolation and/or purification of a nucleic acid molecule, polypeptide or peptide of the invention, so that it is not associated with in vivo substances and is substantially free of infectious agents.

I. Nucleic Acid Molecules of the Invention

A. Sources of the Nucleic Acid Molecules of the Invention

Sources of nucleotide sequences from which the present nucleic acid molecules encoding OmpH, a subunit or a variant thereof, or the nucleic acid complement thereof, include total RNA, or genomic DNA or cDNA from any isolate of *P. multocida* or from physiological fluid or tissue of eukaryotic organisms infected with *P. multocida*, preferably an infected avian. Other sources of the DNA molecules of the invention include genomic libraries derived from any *P. multocida*-infected eukaryotic cellular source. Moreover, the present DNA molecules which encode a subunit of full-length OmpH may be prepared in vitro, e.g., by synthesizing an oligonucleotide of about 200, preferably about 100, more preferably about 75, nucleotides in length, or by subcloning a portion of a DNA segment that encodes a particular OmpH.

B. Isolation of a Gene Encoding a *P. mullocida* OmpH

A nucleic acid molecule encoding an OmpH of the invention can be identified and isolated using standard methods, as described by Sambrook et al., *Molecular Cloning: A Laboratory Manual*, Cold Spring Harbor, NY (1989). For example, reverse-transcriptase PCR (RT-PCR) can be employed to isolate and clone OmpH cDNAs. A primer which is complementary to the RNA encoding an OmpH, and preferably hybridizes to the 3' two-thirds of the RNA can be employed as a primer in a reverse transcriptase reaction to prepare first-strand cDNAs from isolated RNA which contains RNA sequences of interest, e.g., total RNA isolated from an infected avian tissue. RNA can be isolated by methods known to the art, e.g., using TRIZOL™ reagent (GIBCO-BRL/Life Technologies, Gaithersburg, Md.). Resultant first-strand cDNAs are then amplified in PCR reactions.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers comprising at least 7–8 nucleotides. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, New York, 1989). Thus, PCR-based cloning approaches rely upon conserved sequences deduced from alignments of related gene or polypeptide sequences.

Primers are made to correspond to highly conserved regions of polypeptides or nucleotide sequences which were identified and compared to generate the primers, e.g., by a sequence comparison of other bacterial porin genes or OmpH genes. One primer is prepared which is predicted to anneal to the antisense strand, and another primer prepared which is predicted to anneal to the sense strand, of a DNA molecule which encodes OmpH.

The products of each PCR reaction are separated via an agarose gel and all consistently amplified products are gel-purified and cloned directly into a suitable vector, such as a known plasmid vector. The resultant plasmids are subjected to restriction endonuclease and dideoxy sequencing of double-stranded plasmid DNAs. Alternatively, the gel-purified fragment can be directly sequenced.

As used herein, the terms "isolated and/or purified" refer to in vitro isolation of a nucleic acid molecule or polypeptide molecule from its natural cellular environment, and from association with other components of the cell, such as nucleic acid or polypeptide, so that it can be sequenced, replicated, and/or expressed. For example, "isolated OmpH nucleic acid" is RNA or DNA containing greater than 9, preferably 36, and more preferably 45 or more, sequential nucleotide bases that encode at least a portion of OmpH, or a variant thereof, or a RNA or DNA complementary thereto, that is complementary or hybridizes, respectively, to RNA or DNA encoding the OmpH and remains stably bound under stringent conditions, as defined by methods well known in the art, e.g., in Samibrook et al., supra. Thus, the RNA or DNA is "isolated" in that it is free from at least one contaminating nucleic acid with which it is normally associated in the natural source of the RNA or DNA and is preferably substantially free of any other RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source. An example of isolated OmpH nucleic acid is RNA or DNA that encodes a *P. multocida* OmpH and shares at least about 70%, preferably at least about 80%, and more preferably at least about 90%, sequence identity with the OmpH polypeptide having SEQ ID NO:2, SEQ ID NO:4, SEQ ID NO:31, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, or SEQ ID NO:43.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.*, 9, 6103 (1981), and Goeddel et al., *Nucleic Acids Res.*, 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

As used herein, the term "derived" with respect to a RNA molecule means that the RNA molecule has complementary sequence identity to a particular DNA molecule.

C. Variants of the Nucleic Acid Molecules of the Invention

Nucleic acid molecules encoding amino acid sequence variants of OmpH or a peptide thereof are prepared by a variety of methods known in the art. These methods include, but are not limited to, isolation from a natural source (in the case of naturally occurring amino acid sequence variants or serotypes) or preparation by oligonucleotide-mediated (or site-directed) mutagenesis, PCR mutagenesis, and cassette mutagenesis of an earlier prepared variant or a non-variant version of OmpH.

Oligonucleotide-mediated mutagenesis is a preferred method for preparing amino acid substitution variants of OmpH. This technique is well known in the art as described by Adelman et al., *DNA*, 2, 183 (1983). Briefly, OmpH DNA is altered by hybridizing an oligonucleotide encoding the desired mutation to a DNA template, where the template is the single-stranded form of a plasmid or bacteriophage containing the unaltered or native DNA sequence of OmpH. After hybridization, a DNA polymerase is used to synthesize an entire second complementary strand of the template that will thus incorporate the oligonucleotide primer, and will code for the selected alteration in the OmpH DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.*, 75 5765 (1978).

The DNA template can be generated by those vectors that are either derived from bacteriophage M13 vectors (the commercially available M 13 mp 18 and M13mp19 vectors are suitable), or those vectors that contain a single-stranded phage origin of replication as described by Viera et al., *Meth. Enzymol.*, 153, 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, New York, 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of OmpH, and the other strand (the original template) encodes the native, unaltered sequence of OmpH. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for peptide or polypeptide production, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as E. coli JM 101.

For example, a preferred embodiment of the invention is an isolated and purified DNA molecule comprising a preselected DNA segment encoding OmpH having SEQ ID NO:2, wherein the DNA segment comprises SEQ ID NO:1, or variants of SEQ ID NO:1, having nucleotide substitutions which are "silent" (see FIG. 19). That is, when silent nucleotide substitutions are present in a codon, the same amino acid is encoded by the codon with the nucleotide substitution as is encoded by the codon without the substitution. For example, valine is encoded by the codons GTT, GTC, GTA and GTG. A variant of SEQ ID NO:1 at the third codon in the mature form of the polypeptide (GTT in SEQ ID NO:1) includes the substitution of GTC, GTA or GTG for GTT. Other "silent" nucleotide substitutions in SEQ ID NO:1 which can encode a polypeptide corresponding to SEQ ID NO:2 can be ascertained by reference to FIG. 19 and page D1 in Appendix D in Sambrook et al., Molecular Cloning: A Laboratory Manual (1989). Nucleotide substitutions can be introduced into DNA segments by methods well known to the art. See, for example, Sambrook et al., supra. Likewise, nucleic acid molecules encoding other OmpHs may be modified in a similar manner. Thus, nucleic acid molecules encoding at least a portion of OmpH, or the complement thereto, may be modified so as to yield nucleic acid molecules of the invention having silent nucleotide substitutions, or to yield nucleic acid molecules having nucleotide substitutions that result in amino acid substitutions (see polypeptide and peptide variants hereinbelow).

II. Preparation of Agents Falling Within the Scope of the Invention

A. Nucleic Acid Molecules

1. Chimeric Expression Cassettes

To prepare expression cassettes for transformation herein, the recombinant or preselected DNA sequence or segment may be circular or linear, double-stranded or single-stranded. A preselected DNA sequence which encodes an RNA sequence that is substantially complementary to a RNA sequence encoding OmpH is typically a "sense" DNA sequence cloned into a cassette in the opposite orientation (i.e., 3' to 5' rather than 5' to 3'). Generally, the preselected DNA sequence or segment is in the form of chimeric DNA, such as plasmid DNA, that can also contain coding regions flanked by control sequences which promote the expression of the preselected DNA present in the resultant cell line.

As used herein, "chimeric" means that a vector comprises DNA from at least two different species, or comprises DNA from the same species, which is linked or associated in a manner which does not occur in the "native" or wild type of the species.

Aside from preselected DNA sequences that serve as transcription units for OmpH, or portions thereof, a portion of the preselected DNA may be untranscribed, serving a regulatory or a structural function. For example, the preselected DNA may itself comprise a promoter that is active in the host cell, or may utilize a promoter already present in the genome that is the transformation target. Many promoter elements well known to the art may be employed in the practice of the invention.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Other elements functional in eukaryotic host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of E. coli, the beta-glucuronidase gene (gus) of the uidA locus of E. coli, and the luciferase gene from firefly Photinus pyralis. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

2. Transformation into Host Cells

The recombinant DNA can be readily introduced into the host cells, e.g., mammalian, bacterial, yeast or insect cells by transfection with an expression vector comprising DNA encoding OmpH or its complement, by any procedure useful for the introduction into a particular cell, e.g., physical or biological methods (e.g., recombinant phage or viruses), to yield a transformed cell having the recombinant DNA stably integrated into its genome, so that the DNA molecules, sequences, or segments, of the present invention are expressed by the host cell.

Physical methods to introduce a preselected DNA into a host cell include calcium phosphate precipitation, lipofection, particle bombardment, microinjection, electroporation, and the like. The main advantage of physical methods is that they are not associated with pathological or oncogenic processes of viruses in eukaryotic hosts. However, they are less precise, often resulting in multiple copy insertions, random integration, disruption of foreign and endogenous gene sequences, and unpredictable expression.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of bacterial origin, but cell lines or host cells of mammalian origin may be employed, as well as plant, insect, yeast, or fungal sources. Generally, the preselected DNA sequence is related to a DNA sequence which is resident in the genome of the host cell but is not expressed, or not highly expressed, or, alternatively, overexpressed. Alternatively, the preselected DNA sequence is not related to a DNA sequence which is resident in the genome of the host cell.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence. Preferably, the transfected DNA is a chromosomally integrated recombinant DNA sequence, which comprises a gene encoding OmpH or its complement, which host cell may or may not express significant levels of autologous or "native" OmpH.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular OmpH, e.g., by immunological means (ELISAs and Western blots) or by assays described herein to identify agents falling within the scope of the invention.

To detect and quantitate RNA produced from introduced preselected DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the products of the introduced preselected DNA sequences or evaluating the phenotypic changes brought about by the expression of the introduced preselected DNA segment in the host cell.

B. Polypeptides. Peptides. Variants. and Derivatives Thereof

The present isolated, purified polypeptides, peptides, variants or derivatives thereof, can be synthesized in vitro, e.g., by the solid phase peptide synthetic method or by recombinant DNA approaches (see above). When a OmpH DNA of the invention is expressed in a recombinant cell, it is necessary to purify the recombinant polypeptide from other recombinant cell proteins or polypeptides to obtain preparations that are substantially homogenous as to the recombinant OmpH. For example, the culture medium or lysate can be centrifuged to remove particulate cell debris. The membrane and soluble protein fractions are then separated. OmpH may then be purified from the soluble protein fraction. Alternatively, OmpH may be purified from the insoluble fraction, i.e., refractile bodies (see, for example, U.S. Pat. No. 4,518,526), if necessary. OmpH polypeptide may be purified from contaminant soluble or membrane proteins and polypeptides by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography, and the like.

If expressed as a fusion polypeptide, the fusion polypeptide may be purified by methods specific for the non-OmpH portion of the fusion polypeptide. For example, if the fusion polypeptide is a histidine tagged fusion polypeptide, Ni-NTA resin may be employed to purify the fusion polypeptide.

OmpH, a variant, or a peptide thereof, can also be prepared by in vitro transcription and translation reactions. An OmpH expression cassette can be employed to generate OmpH gene-specific transcripts which are subsequently translated in vitro so as to result in a preparation of substantially homogenous OmpH, variant OmpH, or a biologically active subunit thereof. The construction of vectors for use in vitro transcription/translation reactions, as well as the methodologies for such reactions, are well known to the art.

To prepare peptides of the invention, the solid phase peptide synthetic method is preferably employed. The solid phase peptide synthetic method is an established and widely used method, which is described in the following references: Stewart et al., *Solid Phase Peptide Synthesis*, W. H. Freeman Co., San Francisco (1969); Merrifield, *J. Am. Chem. Soc.*, 85 2149 (1963); Meienhofer in "Hormonal Proteins and Peptides," ed.; C. H. Li, Vol. 2 (Academic Press, 1973), pp. 48–267; and Bavaay and Merrifield, "The Peptides," eds. E. Gross and F. Meienhofer, Vol. 2 (Academic Press, 1980) pp. 3–285. These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; or ligand affinity chromatography.

Once isolated and characterized, derivatives, e.g., chemically derived derivatives, of a given recombinant OmpH or peptide thereof can be readily prepared. For example, amides of the OmpH, a variant or a peptide thereof may also be prepared by techniques well known in the art for converting a carboxylic acid group or precursor, to an amide. A preferred method for amide formation at the C-terminal carboxyl group is to cleave the peptide from a solid support with an appropriate amine, or to cleave in the presence of an alcohol, yielding an ester, followed by aminolysis with the desired amine.

Salts of carboxyl groups of a polypeptide, peptide or variant of the invention may be prepared in the usual manner by contacting the polypeptide, peptide, or variant thereof with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of OmpH, a peptide or a variant thereof may be prepared by utilizing an N-acyl protected amino acid for the final condensation, or by acylating a protected or unprotected polypeptide or peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N- and O-acylation may be carried out together, if desired.

Formyl-methionine, pyroglutamine and trimethyl-alanine may be substituted at the N-terminal residue of the polypeptide, peptide or variant thereof. Other amino-terminal modifications include aminooxypentane modifications (see Simmons et al., *Science*, 276, 276 (1997)).

In addition, the amino acid sequence of a polypeptide or peptide of the invention can be modified so as to result in a variant. The modification includes the substitution of at least one amino acid residue in the polypeptide or peptide for another amino acid residue, including substitutions which utilize the D rather than L form, as well as other well known amino acid analogs. These analogs include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, omithine, citruline, a-methyl-alanine, para-benzoyl-phenylalanine, phenylglycine, propargylglycine, sarcosine, and tert-butylglycine.

One or more of the residues of the polypeptide or peptide can be altered, so long as the peptide variant is biologically active. For example, it is preferred that the variant has at least about 10% of the biological activity of the corresponding non-variant polypeptide, such as a polypeptide having SEQ ID NO:2. Conservative amino acid substitutions are preferred—that is, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids.

Conservative substitutions are shown in FIG. 20 under the heading of exemplary substitutions. More preferred substitutions are under the heading of preferred substitutions. After the substitutions are introduced, the variants are screened for biological activity.

Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic; trp, tyr, phe.

The invention also envisions polypeptide or peptide variants with non-conservative substitutions. Non-conservative substitutions entail exchanging a member of one of the classes described above for another.

Acid addition salts of amino residues of the polypeptide, peptide or variant thereof may be prepared by contacting the polypeptide, peptide or variant with one or more equivalents of the desired inorganic or organic acid, such as, for example, hydrochloric acid. Esters of carboxyl groups of the polypeptides, peptides or variants may also be prepared by any of the usual methods known in the art.

Other modifications include the reduction of cysteinyl thiol groups with 2-mercaptoethanol and carboxymethylated with iodoacetamide as described by Lambden et al. (1981).

Moreover, it is also envisioned that the peptides of the invention are modified in a manner that increases their stability in vivo, or which presents immunogenic epitopes in a more native configuration. These modified agents are termed "derivatives." Methods to prepare such derivatives are well known to the art. One method is to prepare derivatives which are cyclized peptides (see EPA 471,453 (amide bonds); EPA 467,701 (disulfide bonds); EPA 467,699 (thioether bonds)). Other modifications are disclosed in Jameson et al. (*Nature*, 368, 744 (1994)); U.S. Pat. No. 4,992,463; and U.S. Pat. No. 5,091,396. For example, to cyclize peptides by oxidation of free cysteinyl thiol groups, peptide (0.1 mg ml$^{-1}$) is reacted for 1 hour at 0° C. with iodine (1 mM in methanol) and the oxidation is then quenched with sodium thiosulphate. The mixture is subjected to reverse-phase HPLC on a semi-preparative Zorbax C8 column, followed by gel filtration on a Zorbax GF250 column. Two peaks which are separated by the gel filtration step were further analyzed by mass spectroscopy, using an Applied Biosystems Biolon 20 Biopolymer plasma desorption time-of-flight Mass Analyzer. The first peak is resolved by mass analysis into two species, a partially protected monomer peptide and a dimeric peptide. The material is tested for free cysteine thiol groups with Ellman's reagent [5,5-dithio-bis(2-nitrobenzoic acid); Sigma] at the highest concentration of peptide before saturation (20 mg ml$^{-1}$).

This peak represents the cyclic peptide and is stored at pH 4.0 at −20° C. until used (see Tam & Lu (1989)). A preferred embodiment of the invention is OmpH peptide or variant that has been cyclized by addition of one or more cysteine residues to the N and/or C terminus of the peptide with subsequent oxidation of the free cysteinyl thiol groups.

III. Detection of *P. multocida* Antibodies

The present invention further relates to diagnostic assays for use in veterinary medicine. For diagnosis of fowl cholera or *P. multocida* infection status, the presence of antibodies to the OmpH of *P. multocida* in animal serum is determined. Many types of test formats, as one skilled in the art will recognize, can be used. Such tests include, but are not limited to, IFA, RIA, RIST, ELISA, agglutination and hemagglutination. The diagnostic assays can be performed using standard protocols.

Specifically, a diagnostic assay of the present invention can be constructed by coating on a surface (i.e., a solid support) for example, a plastic bead, a test tube, a fiber strip, a microtitration plate or a membrane (e.g., nitrocellulose membrane), all or a unique portion of the OmpH polypeptide or peptide (natural or synthetic), or an isolated *P. multocida* preparation, and contacting it with the serum or other physiological fluid taken from an animal suspected of having a *P. multocida* infection or fowl cholera. Following removal of the physiological fluid, any antibody bound to the immobilized OmpH, peptide or lysed bacterial preparation (the antigen) can be detected, preferably by reacting the binary antibody-antigen complexes with a “detection antibody”, which detection antibody comprises a detectable label or a binding site for a detectable label. Suitable detectable labels are enzymes, fluorescent labels or radiolabels. Binding sites for detectable labels include avidin, biotin, streptavidin and the like.

In another embodiment of the diagnostic assay of the present invention, all or a unique portion of the OmpH polypeptide or peptide, or lysed bacterial preparation, is bound to an inert particle of, for example, bentonite, polystyrene, or latex. The particles are mixed with serum from an animal in, for example, a well of a plastic agglutination tray. The presence or absence of antibodies in the animal’s serum is determined by observing the settling pattern of the particles in the well.

IV. Dosages. Formulations and Routes of Administration of the Bacterial Preparations. Polvpeptides and Peptides of the Invention Isolated recombinant bacterial preparations, polypeptides or peptides of the invention are preferably administered to a vertebrate, e.g., a bird such as a turkey or chicken, so as to result in an immune response specific for *P. multocida*, OmpH or a peptide thereof, including the peptide or polypeptide encoded by the nucleic acid molecules of the invention. These compounds and compositions can be administered to avians and mammals for veterinary use, such as for use with domestic or farm animals. In general, the dosage of recombinant bacteria required for efficacy will range from about $10^4$ to about $10^{11}$, preferably about $10^5$ to about $10^{10}$, and more preferably about $10^6$ to about $10^9$, colony forming units (CFU), although other amounts may prove efficacious. For polypeptides and peptides of the invention, the dosage required is about 1 μg to about 10 mg, preferably about 10 μg to about 1 mg, and more preferably about 100 μg to about 500 μg, although other dosages may be employed. In particular, for administration of polypeptide or peptide of the invention to a bird, e.g., turkeys or chickens, the amount administered may be at dosages of at least about 1 μg to about 10 mg, preferably about 10 μg to about 1 mg, and more preferably about 100 μg to about 500 μg, although other dosages may provide beneficial results. Dosages within these ranges can be administered via bolus doses or via a plurality of unit dosage forms, until the desired effects have been obtained. The amount administered will vary depending on various factors including, but not limited to, the specific immunogen chosen, the weight, physical condition and age of the animal, and the route of inoculation. Thus, for peptides and polypeptides, the absolute weight of the polypeptide or peptide included in a given unit dosage form of vaccine can vary widely, and depends upon factors such as the species, age, weight and physical condition of the animal considered for vaccination, as well as the method of administration. Such factors can be readily determined by the veterinarian employing animal models or other test systems which are well known to the art. A unit dose of a polypeptide or peptide vaccine is preferably administered parenterally, e.g., by subcutaneous or by intramuscular injection.

The polypeptides or peptides of the invention may also be conjugated or linked to an immunogenic protein, such as KLH or albumin, to enhance their immunogenicity. For example, synthetic peptides are coupled to KLH through the C-terminal cysteine of the peptide using the heterobifunctional reagent N-γ-maleimidobutyric acid N-hydroxysuccinimide ester (GMBS; Sigma). Carrier protein [4 mg KLH $ml^{-1}$ in 100 μl phosphate buffered saline (PBS) pH 7.4] is activated by reaction with GMBS (0.5 mg per 5 μl dimethylformamide) for 1 hour at 25° C. under nitrogen gas. The activated protein is separated from excess GMBS by gel filtration on Sephadex G25 (Pharmacia). Column fractions containing the carrier protein (monitored by $A_{280}$) are pooled, and added to 4 mg peptide dissolved in an equivalent volume of PBS. The mixture is gassed with nitrogen, and incubated at 25° C. for 3 hours with gentle stirring. The progress of the conjugation is monitored colorimetrically from reactivity of free cysteine thiol groups with Ellman’s reagent. Coupling is complete when no color change is observed. The carrier-conjugated peptides are stored at −20° C. until used.

Preferably, the administration of the therapeutic agents of the invention is to a bird so as to result in an immune response which inhibits or prevents fowl cholera, or so as to result in the production of antibodies to the *P. multocida*, the OmpH, or peptide employed as an immunogen. Both local and systemic administration is contemplated. Systemic administration is preferred.

Also envisioned is the administration of maternal antibody, which antibody is obtained from a female animal exposed to a recombinant bacterial preparation, a nucleic acid molecule, peptide or polypeptide of the invention. For example, a hen is vaccinated with at least one of the immunogenic compositions of the invention. The hen then provides passive immunity to progeny through the transfer of maternal antibody to the embryo. Alternatively, an egg-laying animal, e.g., a chicken, may be immunized and the eggs from that animal collected. Antibody is recovered from the eggs and then administered to susceptible animals, e.g., turkeys, to provide passive protection. Preferably, the turkeys are subsequently exposed to live or killed *P. multocida*, or other compositions of the invention, to provide active protection.

The recombinant bacterial compositions may be administered as live, tmodified-live (attenuated) or inactivated bacteria, or optionally administered as a combination of attenuated, inactivated, and/or live bacteria, or in combination with a polypeptide or peptide of the invention, or any combination thereof. Moreover, the administration of more than one immunogenic agent of the invention to an animal may occur simultaneously or at different times. The bacteria may be inactivated by agents including, but not limited to, formalin, phenol, ultraviolet radiation, and β-propiolactone.

Typically, immunogenic compositions are prepared for injection or infision, either as liquid solutions or suspensions. Solid forms suitable for solution in, or suspension in, liquid vehicles prior to injection or infusion may also be prepared. The preparation may also be emulsified. The active ingredient can be mixed with diluents, carriers or excipients which are physiologically acceptable and compatible with the active ingredient(s). Suitable carriers can be positively or negatively charged or neutral avridine-containing liposomes, oil emulsions; live-in-oil; killed-in-oil, water-in-oil; $Al(OH)_3$; oil emulsion with terpene oils squalene or squalene; or aqueous. Suitable diluents and excipients are, for example, water, saline, PBS, glycerol, or the like, and combinations thereof. In addition, if desired, the compositions may contain minor amounts of auxiliary substances such as wetting or emulsifying agents, stabilizing or pH-buffering agents, and the like.

Such compositions are conventionally administered parenterally, by injection, for example in birds, either intravenously, intramuscular injection to breast, lung or thigh, subcutaneous injection, wing web injection, or administration via the beak, spraying the animals and their environment, e.g., their housing or yard, or adminstration in the drinking water or feed. The administration of maternal antibody or recombinant bacteria is preferably in feed or water. Polypeptide or peptide is preferably administered via injection. Formulations which are suitable for other modes of administration include suppositories, cloaca, insufflated powders or solutions, eye drops, nose drops, intranasal aerosols, and oral formulations, e.g., introduced into drinking water. Oral formulations include such normally employed excipients as, for example, pharmaceutical grades of alkylcelluloses, mannitol, dextrose, lactose, starch, magnesium stearate, sodium saccharin, cellulose, magnesium carbonate, and the like. Thus, these compositions can take the form of solutions, suspensions, tablets, pills, hard or soft gelatin capsules, sustained-release formulations such as liposomes, gels or hydrogels; or powders, and can contain about 10% to about 95% of active ingredient, preferably at about 25% to about 70%.

One or more suitable unit dosage forms comprising the bacterial preparations, polypeptides or peptides of the invention, which may optionally be formulated for sustained release. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

To prepare an immunogenic composition comprising a polypeptide, peptide or variant thereof, the purified polypeptide, peptide or variant can be isolated as described hereinabove, lyophilized and stabilized. Alternatively, the polypeptide or peptide may be modified so as to result in a derivative polypeptide or peptide, as described above. The polypeptide or peptide antigen may then be adjusted to an appropriate concentration, optionally combined with a suitable carrier and/or suitable vaccine adjuvant, and preferably packaged for use as a vaccine. Suitable adjuvants include, but are not limited to, surfactants, e.g., hexadecylamine, octadecylanine, lysolecithin, di-methyldioctadecylammonium bromide, N,N-dioctadecyl-n'-N-bis(2-hydroxyethyl-propane di-amine), methoxyhexadecylglycerol, and pluronic polyols; polanions, e.g., pyran, dextran sulfate, poly IC, polyacrylicacid, carbopol; peptides, e.g., muramyl dipeptide, dimethylglycine, tuftsin, oil emulsions, alum, and mixtures thereof. Finally, the immunogenic product may be incorporated into liposomes for use in a vaccine formulation, or may be conjugated to polysaccharides or other polymers.

Vaccination schedules and efficacy testing for avians are well known to the art, e.g., see Rimler et al., 1979; Schlink et al., 1987; Wang et al., 1994a; Wang et al., 1994b; Zhang et al., 1994; and Rimler et al., 1981.

The invention will be further described by reference to the following Examples.

EXAMPLE I

Cloning and Characterization of the Major Outer Membrane Protein Gene (OmpH) of *Pasteurella Multocida* Strain X-73

Materials and Methods

Bacterial strains and plasmids. The strains or serotypes of *P. multocida* used in this research were X-73 (serotype 1), P-1059 (serotype 3), P-1662 (serotype 4), P-1702 (serotype 5), type strains of serotypes 6, 7, 8, 9, 10, 11, 12, 13, 14, 15, 16, and the CU vaccine strain (serotype 3,4). All isolates were obtained from the National Animal Disease Center (Ames, Iowa). *E. coli* strain XL1-Blue MRF' was obtained from Stratagene (La Jolla, Calif.). pUC 18 was obtained from Boehringer Mannheim (Indianapolis, Ind.). pNOTA/T7 and relevant Prime PCR Cloner system was obtained from 5 Prime-3 Prime, Inc. (Boulder, Colo.). pQE30 and pQE32 expression vector kit was obtained from Qiagen, Inc. (Chatsworth, Calif.).

Purification of the major outer membrane protein OmpH of X-73. The major outer membrane protein of *P. multocida* X-73 was purified according to the method described by Chevalier et. al. (1993). Briefly, the bacteria were cultured in brain heart infusion (BHI) at 37° C. overnight. The bacteria were then harvested and washed 3 times with phosphate buffered saline (PBS). The washed bacteria were sonicated, and then incubated with 2% sodium N-lauroyl sarcosinate in 50 mM Tris-HCl buffer (pH 7.4) and centrifuged at 206,000 g at 16° C. for 1 hour. This step was repeated once, and the insoluble material was dispersed in 2% sodium dodecyl sulfate (SDS), 0.5 M NaCl, and 5 mM EDTA in 50 mM Tris-HCl buffer (pH 7.4) by stirring at 37° C. for 2 hours. The supernatant was recovered by centrifugation at 206,000g at 25° C. for 1 hour. The supernatant was then applied on a 60×600 Superdex 200 column (Pharmacia Biotech, Piscataway, N.J.) equilibrated and eluted with 50 mM sodium phosphate buffer (pH 7.4) containing 0.1% SDS and 0.3 M NaCl. This procedure was performed at 25° C. to prevent SDS precipitation. Elution of the protein was monitored by UV absorption at 280 nm. The fractions containing OmpH were identified by SDS-polyacrylamide gel electrophoresis (SDS-PAGE) and pooled.

Ouantitation of protein and KDO. Protein was quantitated by the method of Lowry et. al. (1951), with bovine serum albumin as a standard. 2-keto-3-deoxyoctonate (KDO) was determined as described by Hanson and Phillips (1981), using commercial KDO (Sigma, St. Louis, Mo.) as a standard.

N-terminal amino acid sequencing. N-terminal sequencing of the purified X-73 outer membrane protein and recombinant protein were performed by Edman method on a Procise 494 Protein Sequencing System (Applied Biosystems, Foster, Calif.).

Oligonucleotide synthesis. The oligonucleotides were synthesized by the Molecular Genetics Instrumentation Facility of The University of Georgia (Athens, Ga.) and Retrogen Inc. (San Diego, Calif.). Deoxyinosine was also utilized for primers synthesized according to the N-terminal amino acid sequence of OmpH (Table 1).

Construction of genomic DNA library and extraction of plasmids. Genomic DNA of X-73 was isolated using GNOME DNA isolation kit (BIO 101, Inc. La Jolla, Calif.). The genomic DNA was partially digested with Sau3AI or digested to completion with TaqI. The DNA fragments between 2–20 kb of partially digested genomic DNA (fractionated on agarose gel) or the DNA fragments of completely digested genomic DNA were ligated into pUC 18 which had been digested with BamHI or AccI and dephosphorylated with alkaline phosphatase. The ligations were transformed into competent *E. coli* strain XL 1-Blue MRF' cells by electroporation using Gene Pulser (Bio-Rad Laboratories, Hercules, Calif.). The transformants were plated on Luria-Bertani (LB) media containing 200 µg/ml ampicillin. Libraries were screened by colony hybridization using digoxigenin-labeled oligonucleotide as described in the manufacturer's instruction (Boehringer Mannheim, Genius System User's Guide), or all of the clones on the plates were harvested and the plasmids were extracted using PERFECT Prep kit (5 Prime-3 Prime, Inc.).

Amplification of DNA by PCR. A portion of the ompH gene was amplified from a genomic DNA library by PCR as follows. The PCR reaction mixture consisted of 50 ng of genomic library plasmids mixture; 100 pmol of degenerate primers synthesized to encode to the N-terminal amino acid of porin H (Primer A (SEQ ID NO:6) and primer B (SEQ ID NO:8), respectively, see Table 1); 100 pmol of M13 sequencing primers (Primer C (SEQ ID NO:10) and primer D (SEQ ID NO:7), respectively, see Table 1); 0.1 mM dNTP, 1.5 mM $MgCl_2$, and 1.25 units of Taq DNA polymerase (Boehringer Mannheim) in 50 µl of reaction buffer. The amplification reaction included 1 cycle at 94° C. for 2 minutes; 35 cycles each at 94° C. for 15 seconds, 55° C. for 1 minute and 72° C. for 1 minute; and 1 cycle at 72° C. for 10 minutes. The reactions were carried out on Gene Amp PCR System 9600 (Perkin Elmer Cetus Inc., Norwalk, Conn.).

The whole porh gene was amplified by PCR as follows. PCR mixture consisted of 10 ng of genomic X-73 DNA; 30 pmol ofporH gene N-terminus primers; 30 pmol of porh gene downstream primers; the other components are the same as above. The amplification reaction included 1 cycle at 94° C. for 5 minutes; 35 cycles each at 94° C. for 15 seconds, 55° C. for 1 minute, 72° C. for 1 minute; and 1 cycle at 72° C. for 10 minutes.

Inverse PCR. Inverse PCRs were carried out according to Ochman's method (1988). Genomic DNA of X-73 was digested to completion with Sau3AI or HindIII. The digested DNAs were purified and diluted to 10 ng/µl. Self ligations were carried out at 16° C. overnight. For the PCR reaction, two DNA polymerase systems were used. Taq DNA polymerase was used for DNA amplification of self ligation of Sau3AI digested DNA. Expand long template PCR system (Boehringer Mannheim) was used for DNA amplification of self ligation of HindIII digested DNA. The PCR reaction cycle for Taq DNA polymerase was: 1 cycle at 94° C. for 2 minutes; 40 cycles each at 94° C. for 10 seconds, 60° C. for 30 seconds, 70° C. for 2 minutes; and 1 cycle at 72° C. for 10 minutes. The PCR reaction cycle for the expand long template PCR system was: 1 cycle at 94° C. for 2 minutes; 40 cycles each at 94° C. for 10 seconds, 60° C. for 30 seconds, 68° C. for 4 minutes; and 1 cycle at 68 ° C. for 10 minutes.

Subcloning of PCR products. PCR products were cloned into pNOTA/T7 plasmid for subsequent sequencing according to the manufacturer's instructions (5 Prime-3 Prime Inc.). PCR amplified whole omph genes were subcloned into pQE30 and pQE32 expression vector system for expression analysis according to the manufacturer's instructions (Qiagen).

DNA sequence determination and analysis. The PCR products and subcloned PCR inserts in plasmids were sequenced by the dideoxy-chain termination method (Sanger et al., 1977) using Applied Biosystems Model 373A Version 2. 1.0. Sequence analysis was conducted with Hitachi DNAsis Pro 3.0 software (Hitachi Software Engineering Co., Ltd., San Bruno, Calif.) and Gene Construction Kit (Textco, Inc., West Lebanon, N.H.). Sequence similarity searches were performed at the National Center for Biotechnology Information using the BLAST network service (Altschul et al., 1990).

Southern blots and dot blots. Southern blots were carried out according to Genius System User's Guide (Boehringer Mannheim). The probe used was oligo N (SEQ ID NO:5; Table 1), 3'-end labeled with digoxigenin according to the manufacturer's instruction (Boehringer Mannheim). The hybridization was carried out under high stringency (determined by washing at 42° C. in 0.1×SSC). DNA dot blots were carried out as follows. Bacterial DNA was diluted to 200 µg/ml in TrisHCl EDTA (TE) buffer, heated to 100° C. for 10 minutes and chilled immediately on ice. A 1 µl (0.2 µg) of DNA dilution was spotted onto a positively charged nylon membrane (Boehringer Mannheim). The DNA was fixed by baking at 120° C. for 30 minutes. The probe used was a PCR amplified porH gene sequence from X-73 labeled with digoxigenin using Genius 2 DNA Kit. Hybridization and detection were performed as described by the manufacturer (Boehringer Mannheim). Hybridization was carried out under high stringency (determined by washing at 65° C. in 0.5×SSC).

Expression of omph gene in *E. coli* and purification of the recombinant protein. The DNAs encoding the primary protein and the mature protein of the omph gene of X-73 were amplified from genomic X73 DNA using two pairs of primers corresponding to the N-terminal and downstream sequences of omph gene (primer G (SEQ ID NO:14) paired with primer I (SEQ ID NO:16) for primary protein, primer H (SEQ ID NO:15) paired with primer I for mature protein) (Table 3 and FIG. 4). These two PCR products were ligated into expression vectors pQE30 and pQE32 and transformed into competent *E. coli* strain XL1-Blue MRF'. pQE30 and pQE32 expression vectors have a isopropylthio-D-galactoside (IPTG) regulated promoter, T5 promoter, containing two lac operator sequences, followed by the multiple cloning site with 6×histidine tag. Under the induction of IPTG, the 6×histidine tag and the inserted gene were expressed as a fusion protein. The fusion protein is purified by affinity chromatography using Ni-NTA resin according to the materials which accompany the Qiagen QIA kit. Transformants were plated on LB plates containing 200 µg/ml ampicillin. The plasmids in the transformants were extracted and the insert in the plasmids were sequenced to confirm they contained the right sequence of omph gene. Transformants containing omph gene were cultured in SOB broth with or without IPTG. The recombinant proteins were purified according to the manufacturer's instruction (Qiagen).

SDS-PAGE and Western blots. Samples were analyzed on polyacrylarnide gel according to Laemmli's method (1970). Bacterial whole cell lysates (40 µg per well), purified native X-73 OmpH and recombinant protein (4.5 µg per well) were applied to 10% polyacrylamide gels and electrophoresed at 20 mA. The gels were stained with Coomassie blue R-250 for detecting proteins. For Western blots, the proteins were transferred to nitrocellulose membranes (Bio-Rad Laboratories) at 80 volts for 2 hours. Nitrocellulose membranes were then incubated with primary antiserum for 2 hours followed by washing in phosphate buffered saline (PBS) 3 times. The membranes were then incubated with 1:500 HRP-conjugated anti-chicken IgG (Sigma) for 1 hour and followed by washing in PBS 3 times again. Antigens on membranes were visualized by incubation with 3,3'-diaminobenzidine (DAB) and urea hydrogen peroxide solution prepared using fast DAB tablet (Sigma).

Antibody production. Antisera against bacterin of *P. multocida* strain X-73 were prepared as described (Wang et al., 1994a; Wang et al., 1994b). Antisera against native X-73 OmpH and recombinant protein from *E. coli* were prepared as follows. Purified native X-73 OmpH and recombinant protein were emulsified in complete Freund adjuvant. The ratio of aqueous phase to adjuvant was I to 3. The preparation was injected, 0.5 ml (100 µg protein) per bird, twice intramuscularly (at 5 and 8 weeks of age) two weeks apart in specific-pathogen-free (SPF) chickens. Blood was collected 14 days after the second injection. All of the above antisera were absorbed with *E. coli* strain XL 1-Blue MRF' whole cell lysates before being used on Western blot.

Enzyme-linked immunosorbent assay (ELISA). Immunoplates (Nunc, VWR Scientific, Bridgeport, N.J.) were coated at 40° C. overnight with 100 ng of the following antigens: purified X-73 OmpH, recombinant X-73 protein, and X-73 whole cell lysate in borate buffer (pH 9.5). The plates were washed three times with 0.01 M PBS containing 0.05% Tween 20 (pH 7.2), followed by adding 200 µl of blocking buffer (PBS containing 1% bovine serum albumin) and incubated at room temperature for 30 minutes. After washing, 50 µl of antisera serially diluted with blocking buffer were added and incubated at room temperature for 30 minutes. After further washing, 50 µl of 1:5000 diluted rabbit anti-chicken IgG conjugated to horseradish peroxidase (HRP) (Zymed Laboratories, Inc., San Francisco, Calif.) was added and incubated at room temperature for 1 hour. For color development, 100 µl of 3,3',5,5' tetramethybenzidine (TMB) substrate was added and incubated for 30 minutes. Then 0.25% 100 µl of hydrofluoric acid was added to stop the reaction. Absorbance was read at a wavelength of 630 nm using an ELISA reader (MR650, Dynatech Laboratories, Inc., Alexandria, Va.).

Functional assays with planar lipid bilayers. The pore-forming activity of purified X-73 outer membrane protein OmpH and recombinant X-73 OmpH protein were examined by using planar lipid bilayers (Benz et al., 1987; Benz et al., 1978; Hancock et al., 1986). Lipid bilayers made from 1.5% oxidized cholesterol in n-decane were formed across a 0.1 mm$^2$ hole separating two compartments of a Teflon chamber containing 1.0 M KCl. Electrodes were implanted in each compartment, one connected to a voltage source and one to a current amplifier and chart recorder with the output monitored on an oscilloscope. The protein samples were highly diluted in 0.1%. Triton X-100 and approximately 5 ng of the protein was added to one compartment. A voltage of 50 mV was applied across the lipid bilayer. Increases in conductance were recorded, and average single-channel conductances were calculated.

Protection studies in chickens. Purified X-73 outer membrane protein OmpH and recombinant protein from *E. coli* were mixed with monophosphoryl lipid A (Sigma) 0.25 mg/ml. The preparations were used for vaccination in specific pathogen free (SPF) chickens. The birds were divided into 5 groups with 10 birds per group. Group 1 and group 2 were injected intramuscularly with purified native X-73 OmpH and recombinant protein preparation, respectively, 100 µg protein (0.5 ml) per bird. Group 3 was injected intramuscularly with 100 µg per bird native OmpH treated with protease (Boehringer Mannheim). Group 4 was injected intramuscularly with *P. multocida* X-73 bacterin prepared as described previously (Wang et al., 1994a; Wang et al., 1994b). Group 5 was not vaccinated. The birds were vaccinated twice (at 5 weeks and 8 weeks of age) two weeks apart. Fourteen days after the second vaccination, a blood sample was taken from each bird and the birds were challenged with 100 colony forming units (CFU) *P. multocida* X-73. The birds were observed for 10 days after challenge and mortalities were recorded.

Results

Figure 1B:
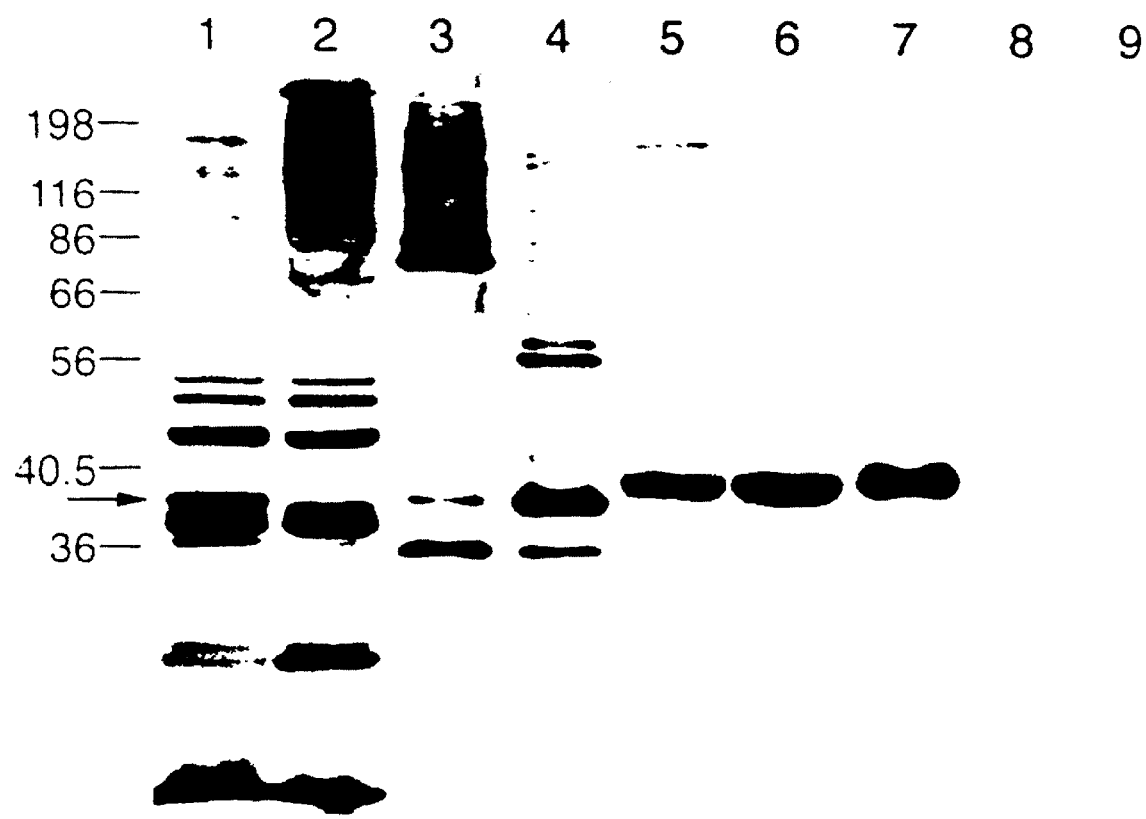
Figure 1C:
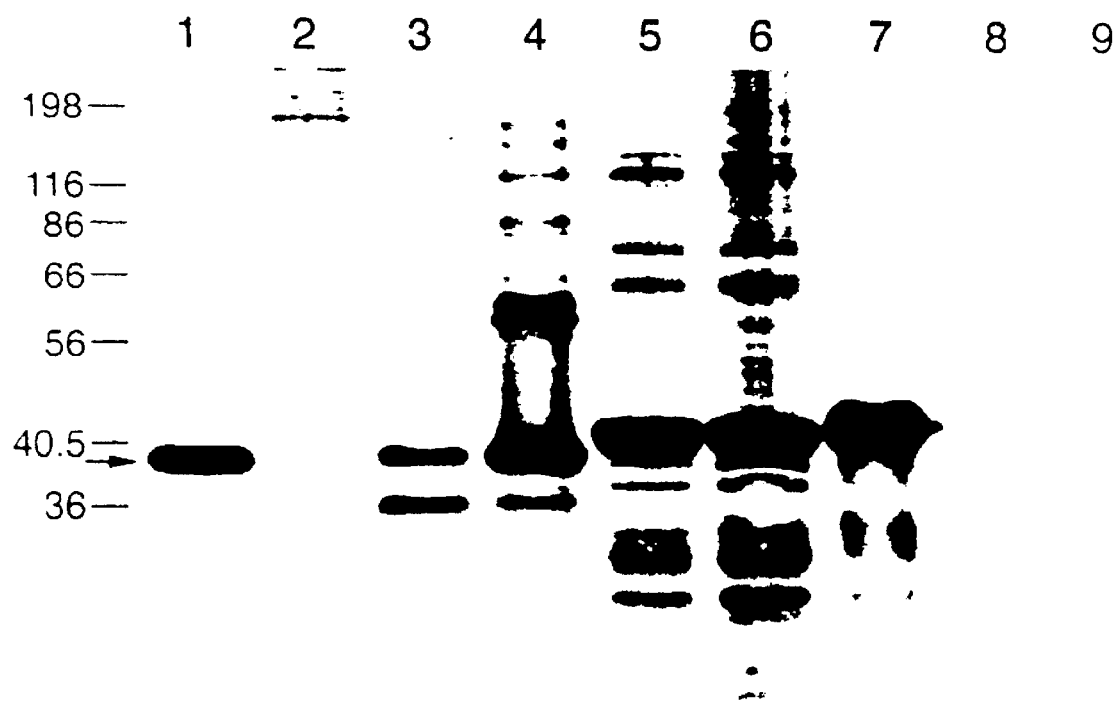
Figure 3:
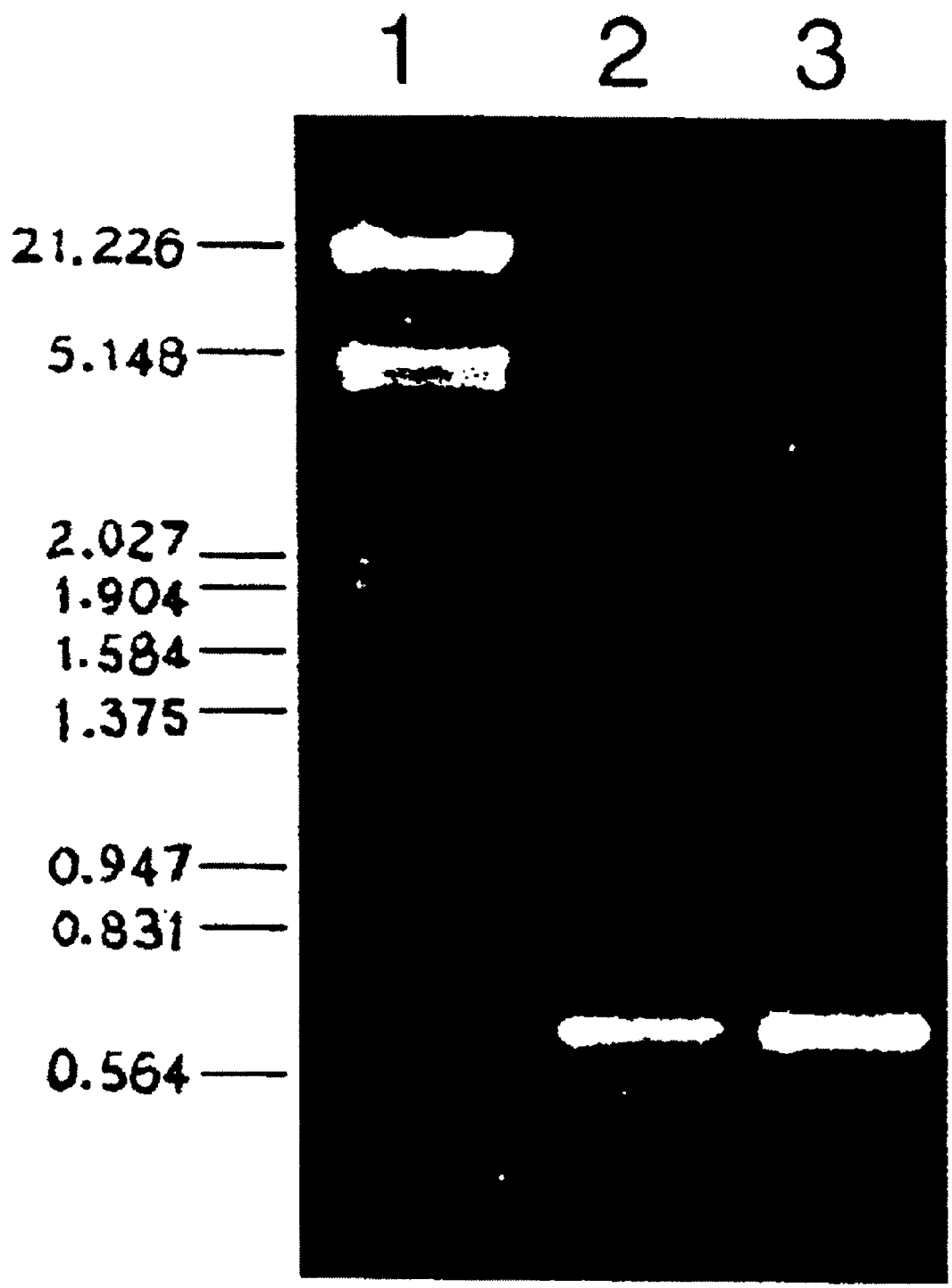

Purification and amino acid sequencing of X-73 major outer membrane protein OmpH. The X-73 major outer membrane protein was purified by detergent treatment of the cell envelope and size exclusion chromatography. The purified outer membrane protein still contained a trace amount of lipopolysaccharides (LPSS) indicated by detection of 0.418 µg KDO (mg proteins$^{-1}$). This indicated that OmpH tends to associate with LPS as has been described for other porins (Gulig et al., 1985; Schindler et al., 1981). The whole cell lysate of X-73 and purified OmpH were analyzed on PAGE and Western blot (FIGS. 1A, 1B, 1C, lanes 1–4). The protein samples dissolved in loading buffer were treated with incubation at 37° C. for 30 minutes or boiled at 100° C. for 10 minutes before loading on the gel.

A heat modifiable property was observed for the major outer membrane protein OmpH (FIGS. 1A and 1B, lanes 1–4; the arrow indicates the position of OmpH monomer). As shown in FIG. 1, the major outer membrane protein band (OmpH monomer) disappeared when the sample was not boiled, but a ladder of high molecular mass protein bands between 76 kDa and 210 kDa appeared at the top region of the gel. The same phenomena occurred to the purified outer membrane protein (FIGS. 1A and 1B, lanes 3 and 4). In SDS-PAGE analysis, the boiled purified outer membrane protein contained a major band with molecular mass about 37 kDa, some faint bands at the higher molecular mass position and a faint band with molecular mass about 35 kDa (FIG. 1A, lane 4). Comparing this with the Western blot assay in which these faint bands were able to react to the antiserum against recombinant OmpH (FIG. 1C, lane 4), the faint bands at the higher molecular position were most likely the insolubilized trimers/oligomers or aggregates of denatured monomers of OmpH and the 35 kDa faint band the undenatured monomers, although the possibility that they were contaminants or degraded OmpHs could not be completely excluded.

For the unboiled purified outer membrane protein, besides the ladder of high molecular protein bands between 76 kDa and 210 kDa, there was also a trace amount of monomers (FIGS. 1A, 1B, and 1C, lane 3). This indicated that a small amount of trimeric or oligomeric form of OmpH was denatured during purification. The ladder of high molecular protein bands probably represented the OmpH trimers or oligomers having different numbers of monomers. They might also represent the trimers associating with different amount of LPS. It was noted that in the Western blot assay, the antiserum against recombinant protein did not react to the unboiled native trimeric or oligomeric proteins of X-73 OmpH (FIG. 1C, lane 3). This indicated that the recombinant protein was denatured and did not contain the conformational epitopes of native OmpH.

A-T-V-Y-N-Q-D-G G-T-K-VD-V-N-G-S-L-R-X-I (SEQ ID NO:11). This N-terminal amino acid sequence was almost identical with that of previously reported porin H from P. multocida serotype D2 except differences at positions 13 and 17 (Chevalier et al., 1990). The N-terminal amino acid sequence was also very similar to that of other reported putative porins of P. multocida (Lubke et al., 1994; Marandi et al., 1996).

Design of synthetic oligonucleotides and hybridization with P. multocida DNA. Three degenerate oligonucleotides, oligo N (SEQ ID NO:5), primer A (SEQ ID NO:6), and primer B (SEQ ID NO:8) were synthesized according to the N-terminal amino acid sequence of OmpH and previous reported porin H. Primer C (SEQ ID NO:10) and primer D (SEQ ID NO:7) were M13 forward and reverse sequencing primers derived from pUC 18 sequence. Primers E to I were also synthesized to correspond to omph gene sequence. Primers A to I were used for PCR amplifications. The sequences and the positions of the primers in subsequently cloned omph gene sequence are shown in Table 1.

TABLE 1

Oligonucleotides used in this study.

| Name | Sequence | Position |
|---|---|---|
| oligo N (SEQ ID NO: 5) | 5'-AC(T/C/A/G)GT(T/C/A/G)TA(T/C)AA(T/C)CA(A/G)GA(T/C)GG-3' | 455–475 |
| primer A (SEQ ID NO: 6) | 5'-GTTTA(T/C)AA(T/C)CA(A/G)GA(T/C)GGIAC-3' | 459–478 |
| primer B (SEQ ID NO: 8) | 5'-AA(T/C)CA(A/G)GA(T/C)GGIACIAA(A/G)GT-3' | 465–484 |
| primer C (SEQ ID NO: 10) | 5'-TGTAAAACGACGGCCAGT-3' | M13 Forward |
| primer D (SEQ ID NO: 7) | 5-'AGCGGATAACAATTTCACACAGGA-3' | M13 Reverse |
| primer E (SEQ ID NO: 12) | 5'-GCTTAAGCCTTCGCCTAAATC-3' | 604–584 |
| primer F (SEQ ID NO: 13) | 5'-TTTGGTGGTGCGTATGTCTTCT-3' | 905–926 |
| primer G[b] (SEQ ID NO: 14) | 5'-TCAACTATGAAAAAGACAATCGTAG-3' | 389–410 |
| primer H[b] (SEQ ID NO: 15) | 5'-TCACAGCAACAGTTTACAATCAAGA-3' | 450–471 |
| primer I[b] (SEQ ID NO: 16) | 5'-CTAGATCCATTCCTTGCAACATATT-3' | 1604–1584 |

[a]position in the X-73 ompH gene (see FIG. 4).
[b]Three extra bases were added at the 5' ends for facilitating subcloning of the PCR products.

Oligo N was used for hybridization. DNA dot blotting with high stringency showed it hybridized with 15 somatic serotypes and the CU vaccine strain. Southern blotting of X-73 DNA showed it hybridized with a single restriction fragment (FIG. 2). The approximate sizes of the hybridized fragments were HindIII, 3.8 kb; Sau3AI, 1.4 Kb; and TaqI, 0.66 Kb. These results also indicated that there was a single chromosome copy of omph gene.

Cloning and sequencing of omph gene fragments of X-73. Initially, libraries were constructed with Sau3AI partially digested X-73 genomic DNA, screened with a probe of oligo N. The screening results were repeatedly negative regardless of the vector and E. coli strain employed, and the backgrounds were also high. Subcloning of gel extracted oligo N-hybridized HindIII and Sau3AI fragments were also negative. The negative results suggested that P. multocida OmpH is lethal for E. coli. This suggested that the smaller oligo N-hybridized fragments in the TaqI digest of X-73 DNA, which presumably did not contain a complete omph gene, would be suitable candidates for cloning. A new library was constructed with TaqI completely digested X-73 genomic DNA. The plasmids of the harvested library clones (mixture) were extracted. PCR reactions were carried out in which the whole library plasmid mixture was used as a template, primer A or primer B was used as the 5' primer and primer C (M13 forward sequencing primer) or primer D (M13 reverse sequencing primer) was used as the 3' primer (see Table 1).

PCR product of about 640 bp was obtained when primer A or primer B was paired with primer D in PCR (FIG. 3). These PCR products were purified from the gels for sequencing. The DNA sequences were determined by both direct sequencing of the PCR products and subcloning of the PCR products into pNOTA/T7 plasmids and sequencing. A 540 bp sequence was obtained. The deduced N-termninal amino acid sequence of the polypeptide encoded by the sequence matched with that of the amino terminus of X-73 OmpH. Based on this sequence, primer E and primer F corresponding to the sequence near both ends of the 540 bp fragment were synthesized (Table 1). Southern blot analysis assay showed that both primer E and F hybridized with Sau3AI and HindIII fragments in FIG. 2. Therefore, these Sau3AI and HindIII fragments contain the flanking sequence of the 540 bp fragment. Sau3AI and HindIII were used to digest X-73 genomic DNA to completion. After self-ligation, the inverse PCRs were carried out. PCR products were analyzed and sequenced. By comparing and analyzing the sequences of the initial PCR products and the subsequent inverse PCR products, the complete X-73 omph gene sequence (SEQ ID NO:1), including the upstream and downstream regulatory regions, was obtained (FIG. 4).

DNA sequence analysis and hybridization of omvh gene with *P. multocida* DNA. The coding region of omph gene is 1059 bp in length. The predicted primary protein is composed of 353 amino acids with a 20 amino acid signal peptide (SEQ ID NO:2). The signal peptide has the common characteristics associated with such sequences, a stretch of hydrophobic amino acids and an Ala-X-Ala cleavage site. The mature protein contains 333 amino acids with a predicted molecular mass of 36.665 kDa which was very close to the molecular mass of the native OmpH, which was determined electrophoretically. There are also putative −35 and −10 promoter sequences, which are similar to the consensus for these sequences in *E. coli*. There is also a Shine-Dalgarno ribosome binding site just 9 base pairs before ATG start codon and an inverse repeat as terminator after TAA stop codon. The predicted N-terminal amino acid sequence matches with that of OmpH determined by amino acid sequencing. A sequence similarity search in GenBank database revealed that the omph gene and the predicted amino acid sequence show similarities to other bacterial porins, especially to *H. influenzae* porin P2 (38% identity for amino acid sequence) (FIG. 5). The amino acid composition of OmpH is typical of nonspecific bacterial porins: a highly negative hydropathy index, high glycine content, low proline content, and a lack of cysteines.

Figure 6:
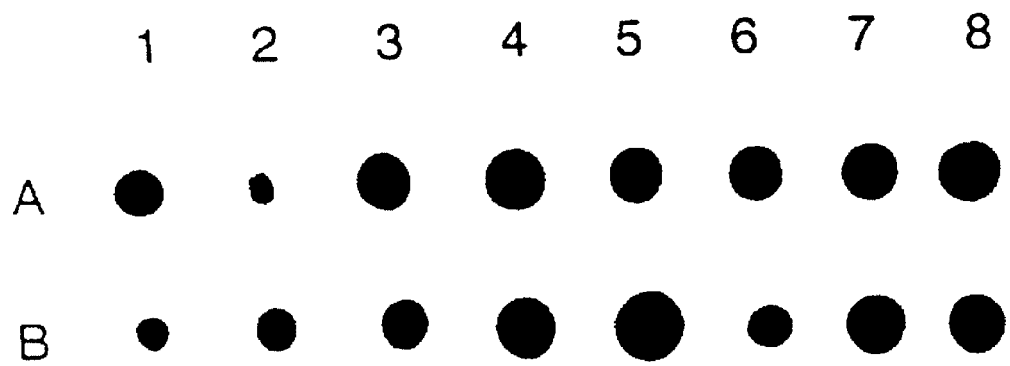

Fifteen somatic serotypes of *P. multocida* and the CU vaccine strain were analyzed to determine the homology and distribution of the omph gene. The labeled omph gene sequence hybridized, under high stringency, with genomic DNAs from 15 somatic serotypes, as well as the vaccine strain CU (FIG. 6).

Expression of omnh gene in *E. coli*. Transformation of recombinant pQE30, which encodes omph containing a signal peptide was repeatedly unsuccessful or only a few colonies were obtained. The plasmids in all of these colonies contained truncated or deleted omph gene after sequence analysis. Transformation of *E. coli* with recombinant pQE32, which contained an omph gene encoding the mature protein resulting in about 2,000 colonies. Five colonies were randomly picked for sequence confirmation of the insert in the plasmids. One colony was chosen for further expression analysis. The plasmid in this colony was designated as pJYH 1. The recombinant protein was purified and the N-terminus was sequenced to confirm that the recombinant protein contained the N-terminal amino acid sequence of OmpH. The recombinant protein has 13 amino acids fused at the N-terminus of OmpH. The recombinant OmpH expressed in *E. coli* was analyzed and detected by PAGE and/or Western blot (FIGS. 1A, 1D and 1C, lanes 5–7). It was interesting that both induced and uninduced *E. coli* harboring pJYHI produced the recombinant OmpH. This indicated that the T5 promoter in pJYHI was not tightly controlled. This also indicated that the mature recombinant OmpH was not lethal for *E. coli*. The fusion recombinant protein had a molecular mass of about 40 kDa (FIG. 1).

Figure 7A:
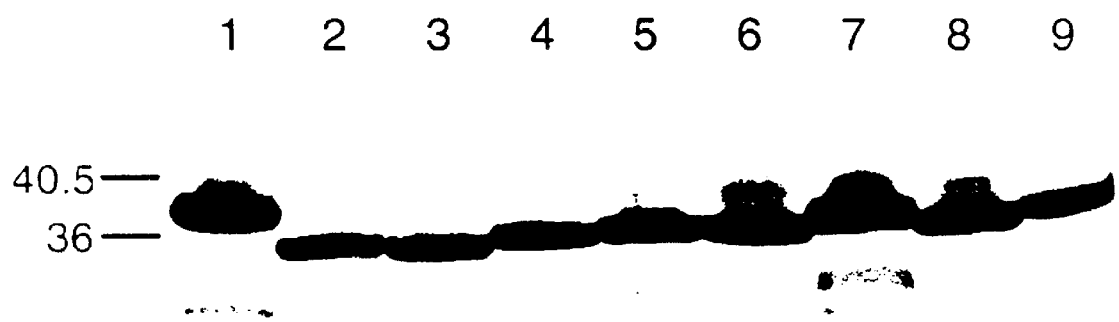
Figure 7B:
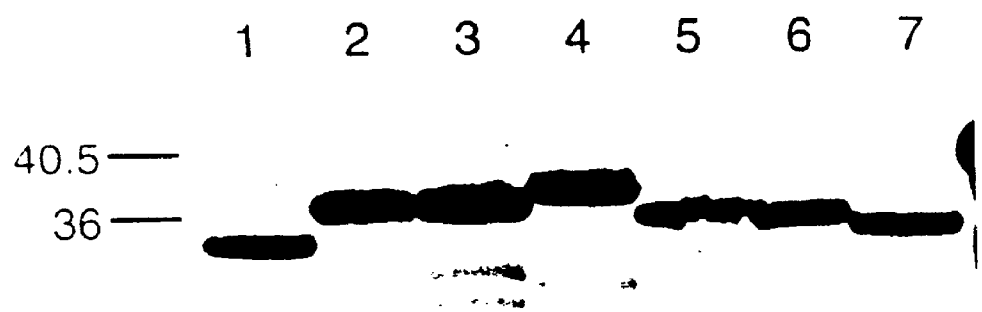

In Western blotting analysis, three antisera, antiserum against X-73 bacterin, antiserum against purified native OmpH and antiserum against recombinant OmpH, were used to detect the recombinant protein. All of the antisera reacted with the recombinant protein and the reaction patterns were the same (FIGS. 1B and 1C). Antiserum against recombinant OmpH of X-73 also reacted to a protein band with molecular masses from 34–37 kDa in 15 somatic serotypes of *P. multocida*, as well as the CU vaccine strain (FIG. 7).

Figure 8:
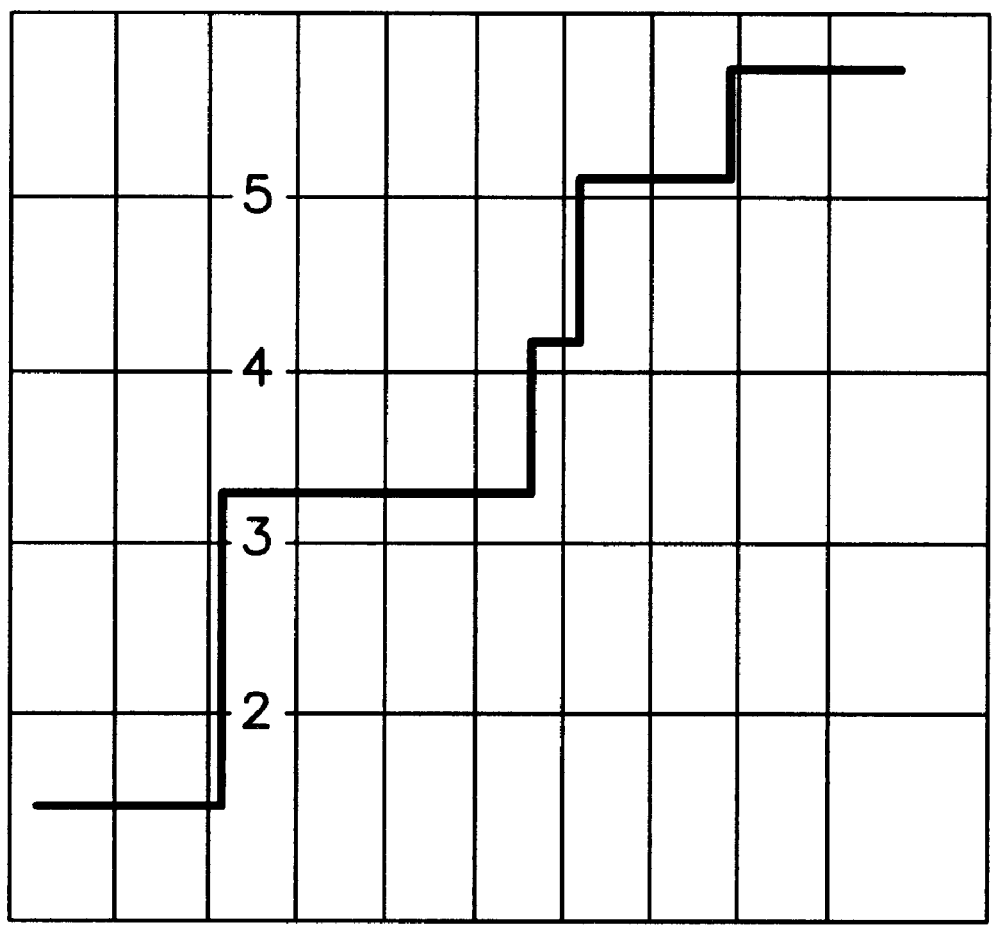
Figure 9:
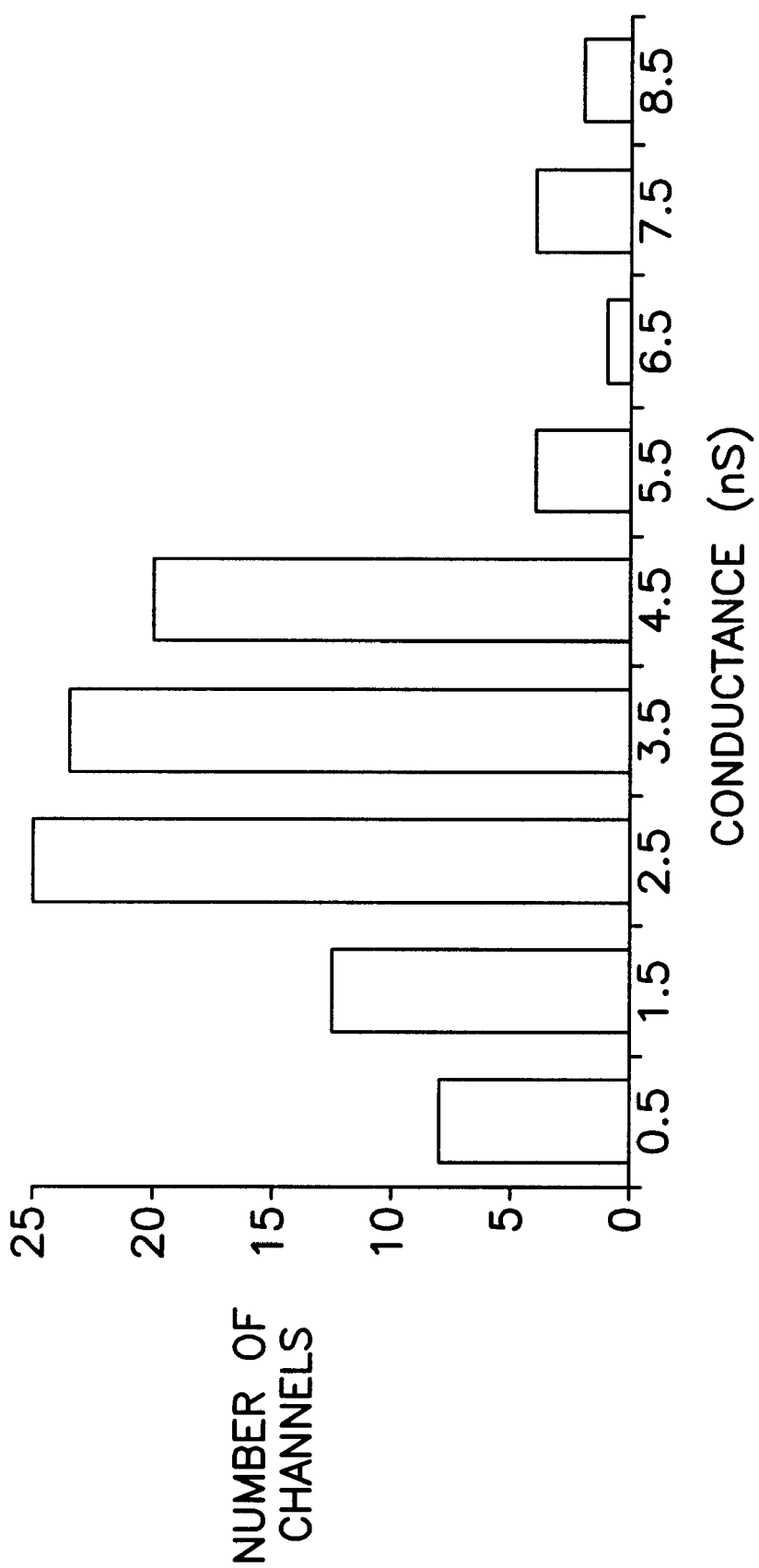

Single-channel conductance of X-73 OmpH and recombinant protein. In order to obtain a single insertion of the porins into the bilayer, the purified X-73 OmpH sample was highly diluted and added to one compartment of the chamber. A voltage of 50 mV was applied. When the purified X-73 OmpH was added, stepwise increases in membrane conductance were observed. This was attributed to the insertion of OmpH into the bilayer and caused the cross-membrane flow of ions in the aqueous phase. The conductance events were amplified through a current amplifier and recorded by a chart recorder. A typical recording is shown in FIG. 8. The observed staircase pattern of conductance increase is typical of porins. The distribution of single-channel increments in conductance caused by X-73 OmpH in 1.0 M KCl is shown in FIG. 9. The average conductance for single channels was 0.62 nS. No conductance increase was observed for recombinant protein. Circular dichroism (CD) spectroscopy was also conducted for comparison of the CD spectra between native OmpH and recombinant protein. There were significant differences in their CD spectra, which indicates that the native OmpH contains a large amount of beta sheets, but the recombinant protein mainly contains irregular structures.

Protection studies. Five groups of SPF birds were used for protection studies using the purified native X-73 OmpH and the recombinant OmpH. *P. multocida* X-73 bacterin was used as positive control and the non-vaccinated groups of birds were used as negative controls. ELISA was used to measure the antibody titers of vaccinated birds. The results of protection studies are shown in Table 2. The purified native X-73 OmpH induced 100% protection against homologous strain challenge. The protease treated native OmpH and recombinant protein induced no protection.

TABLE 2

Protection of vaccinated chickens following challenge [A] with *P. multocida* X-73

| Antigen[B] | ELISA titer against homologous antigen[C] | | No. Dead/Total |
|---|---|---|---|
| | Pre- | Post- | (%)[D] |
| X-73 OmpH | 10 | 56234 | 0/11 (0)[a] |
| Recombinant protein | 10 | 30000 | 9/11 (82)[b] |
| X-73 OmpH protease treated | ND[E] | ND[E] | 10/11 (91)[b] |
| X-73 bacterin | 10 | 31623 | 0/11 (0)[a] |
| non-vaccination | ND[E] | ND[E] | 9/11 (82)[b] |

[A]Chickens were challenged with 100 CFU/bird of X-73.
[B]Chickens were vaccinated at 5 and 8 weeks of age.
[C]Antibody titer was measured before (Pre-) and after vaccination (Post-). Antisera of a group were pooled and measured two times.
[D]Within a column, values followed by different lowercase superscripts are significantly different $p < 0.01$).
[E]ND. Not determined.

Discussion

The trimeric form or oligomeric form of OmpH was purified by selective extraction of the disrupted bacterial cells with sodium N-lauroyl sarcosinate and SDS, followed by size exclusion chromatography. Although the OmpH was significantly purified, the protein still contained a trace amount of LPS as detected by KDO method. Porins usually have a strong association with LPS. It is difficult to obtain a porin completely free of LPS contamination. The OmpH showed heat-modifiable properties when analyzed on PAGE. The fully denatured monomer of OmpH has a molecular mass of approximately 37 kDa. The unboiled OmpH displayed as a ladder of high molecular proteins which may represent the trimeric form or oligomeric form of OmpH and may also associated with LPS as has been described for other putative *P. multocida* porins (Lubke et al., 1994). The N-terminal amino acid sequence of OmpH is very similar to other putative *P. multocida* porins including porin H. They might be the same major outer membrane porin of *P. multocida*. The minor difference might be because they are isolated from different strains or serotypes.

The sequence of omph gene predicted a protein (OmpH) which has typical characteristics of Gram-negative bacterial porins. The amino acid sequence shows similarities to other bacterial porins and has highest similarity to *H. influenzae* protein P2 (38% identity). Protein P2 has been characterized as a porin (Vachon et al., 1986).

The previously reported high molecular mass "cross protection factors" (Wang et al., 1994a; Wang et al., 1994b; Wang 1993) may be the native trimeric or oligomeric forms of OmpH which were not fully solubilized during Western blotting. The differences of molecular masses in "cross-protection factors" at high molecular mass position may be due to the association of different amounts of LPS to the protein (Lubke et al., 1994). Actually, the N-terminal amino acid sequences of "cross-protection factors" 179 kDa and 153 kDa proteins (which were from strain P-1059) are completely identical to that of strain P-1059 OmpH. However, the relationship between OmpH and "cross-protection factors" still need to be further studied.

In the planar lipid bilayer assay, the native X-73 OmpH demonstrated pore-forming activity. This experiment firmly proved that the X-73 major outer membrane protein is a porin. The recombinant OmpH expressed in *E. coli* showed no pore-forming function. This may be because that the recombinant OmpH was not properly folded in *E. coli* or the protein was denatured during purification due to the use of strong denaturants such as guanidine hydrochloride and urea.

In the protection studies, the purified native X-73 OmpH induced 100% protection as did the X-73 bacterin. However, the recombinant OmpH induced little protection. ELISA assay showed that both proteins stimulated high titers of antibodies against homologous antigens. The Western blot showed that the antibodies induced by recombinant protein only reacted to denatured X-73 OmpH, but did not react to native X-73 OmpH, while the antibodies induced by native OmpH were able to react to undenatured native X-73 OmpH. This indicated that the recombinant OmpH was a denatured protein which could not induce antibodies against native conformational epitopes of X-73 OmpH. The ELISA assay showed that the antiserum induced bv the recombinant protein contained very low antibody titers against native OmpH in the whole cell lysate of X-73. According to previous reports of immunization studies with other bacterial porins, the trimeric or native conformation of porin is considered crucial for induction of protective immunity (Marjatta et al., 1992; Muttilainen et al., 1995; Wetzler et al., 1992). The induction of cross-protection by X-73 OmpH in turkeys against strain P-1059 (serotype 3) challenge was also determined. The results showed that X-73 OmpH induced little and inconsistent cross-protection. Although the purified X-73 OmpH still contained a small amount of LPS, the results in Table 1 showed that the induction of homologous protection was due to the protein, not due to the contaminating LPS. It was also unlikely that the protection was induced by the trace amount of the contaminated proteins although this possibility could not be excluded.

The hybridization of the X-73 omph gene sequence with the chromosomal DNAs of the other *P. multocida* serotypes and the reaction of antiserum against X-73 recombinant OmpH to a protein band of the other somatic serotypes indicate that the OmpH gene is conserved among all of the *P. multocida* serotypes.

EXAMPLE II

Characterization of *Pasteurella multocida* Strain P-1059 35kDa Major Outer Membrane Protein and its Encoding Gene Materials and Methods Bacterial strains and plasmids. *P. multocida* P-1059 was obtained from the National Animal Disease Center (Ames, Iowa). *E. coli* strain XL 1-Blue MRF' was obtained from Stratagene (La Jolla, Calif.). pQE expression vector kit was obtained from Qiagen Inc. (Chatsworth, Calif.).

Purification of the major outer membrane protein of P-1059. The major outer membrane protein of P-1059 was purified by detergent (2% sodium N-lauroyl saitcosinate and 2% sodium dodecyl sulfate) treatment of disrupted bacterial cells, followed by size exclusion chromatography as described previously (Chevalier et al., 1993). The whole cell lysate of P-1059 and purified outer membrane protein were analyzed on sodium dodecyl sulfate (SDS) polyacrylamide gel electrophoresis (PAGE) and Western blot as described previously (Laemmli, 1970).

Quantitation of protein and KDO. Protein was quantitated by the method of Lowry et al. (1951). 2-keto-3-deoxyoctonate (KDO) was determined as described by Hanson and Phillips (1981).

N-terminal amino acid sequencing. N-terminal-sequencing of the purified 35 kDa outer membrane protein and recombinant protein was performed by the Edman method on a Procise 494 Protein Sequencing System (Applied Biosystems, Foster, Calif.).

Ionic conductance assay. The pore-forming function of purified P-1059 outer membrane protein was examined by using planar lipid bilayers as described above (Example 1). Lipid bilayers consisting of 1.5% oxidized cholesterol in n-decan were formed across a 0.1 $mm^2$ hole separating two compartments of a Teflon chamber. Each compartment contained 1.0 M KCl solution. Highly diluted purified outer membrane protein (approximately 5 ng) was added to one compartment of the chamber and a voltage of 50 mV was applied. Increases in conductance were recorded and average single-channel conductances were calculated.

Oligonucleotides svnthesis. The oligonucleotides were synthesized by Retrogen Inc. (San Diego, Calif.). Three oligonucleotides used for the PCR reaction were synthesized (three extra bases were added at 5' ends for facilitating subcloning of the PCR products): Primer A 5'-TCAACTATGAAAAAGACAATCGTAG-3' (SEQ ID NO:50), Primer B 5'-TCACAGCAACAG TTTACAATCAAGA-3' (SEQ ID NO:51; primer C 5'-CTAGATCCATTCCTTGCAACATATT-3' (SEQ ID NO:52). Primer A was designed based on the DNA sequence of *P. multocida* X-73 omph gene. Primer C was designed based on the downstream sequence of the coding region of *P. multocida* X-73 omph gene (Example 1). Primer B was derived from the DNA sequence of *P. multocida* P-1059 omph gene encoding primary protein. Primer A paired with Primer C was used for amplification of X-73 omph gene homolog encoding primary protein in *P. multocida* P-1059. Primer B paired with primer C was used for amplification of X-73 omph gene homolog encoding mature protein in *P. multocida* P-1059.

Amplification of DNA bv PCR. The *P. multocida* X-73 OmpH homolog in *P. multocida* P-1059 was amplified by PCR as follows. The PCR mixture consisted of 10 ng of genomic P-1059 DNA; 30 pmol of each ofthe 5' and 3' primer; 0.1 mM dNTP, 1.5 mM $MgCl_2$ and 1.25 units of Taq DNA polymerase (Boehringer Mannheim, Indianapolis, Ind.) in 50 $\mu$l of reaction buffer. The amplification reaction included first 94° C. for 2 minutes; then 35 cycles each at 94° C. for 15 seconds, 55° C. for 1 minute, 72° C. for 1 minute; and 72° C. for 10 minutes. The reactions were carried out on Gene Amp PCR system 9600 (Perkin Elmer Cetus Inc., Norwalk, Conn.). The PCR products were separated on 0.8% agarose gels.

Cloning of PCR Products. The PCR products were ligated into expression vectors pQE30 and pQE32. These two expression vectors have an isopropylthio-D-galactoside (IPTG) regulated promoter, T5 promoter, containing two lac operator sequences, followed by the multiple cloning site with 6×histidine tag. Under the induction of IPTG, the 6×histidine tag and the inserted gene were expressed as a fusion protein. The fusion protein can be easily purified by affinity chromatography using Ni-NTA resin. The ligation of PCR products into plasmids was performed as follows: The PCR products were purified using QIAquick PCR purification kit (Qiagen), then treated with 1 mm dTTP and 3 units T4 polymerase in 35 $\mu$l buffer solution (33 mM Tris-acetate, pH 8.0; 66 mM potassium acetate; 10 mM magnesium acetate; 5 mM dithiothreitol) for 30 minutes at 12° C.) to trim 3' ends. Treated PCR products were purified by ethanol precipitation. pQE30 and pQE32 plasmids were digested by BamHI and HindIII, then treated with 0.1 mM dATP, 0.1 mM dGTP and 4 units Klenow enzyme in 20 μl buffer solution for 15 minutes at room temperature to fill in 3' ends. Treated vector DNA was purified by ethanol precipitation. The treated PCR fragments and vector DNA were then mixed together for a ligation reaction overnight at 160° C. The ligation mixture was transformed into competent *E. coli* strain XL1-Blue MRF' by electroporation using Gene Pulser (Bio-Rad Laboratories, Hercules, Calif.). The transformants were plated on Luria-Bertani (LB) plates containing 200 μg/ml ampicillin. The plasmids were extracted and were used for sequencing of the inserts. The plasmid containing omph gene homolog encoding mature protein was designated as pJYH3.

Sequence determination and analysis. The PCR products and the subcloned PCR inserts in plasmids were sequenced by the dideoxy-chain termination method (Sanger et al., 1977) using Applied Biosystems Model 373A version 2.1.0. Sequence analysis was conducted with Hitachi DNAsis Pro 3.0 Software (Hitachi Software Engineering Co. Ltd., San Bruno, Calif.) and Gene Construction Kit (Textco Inc., West Lebanon, N.H.). Sequence similarity searches were performed at the National Center for Biotechnology Information using BLAST network service (Altschcel et al., 1990).

Antibody preparation. Antisera against P-1059 bacterin and recombinant protein purified from *E. coli* were prepared as described above (Example 1). Antiserum was absorbed with the whole cell lysate of *E. coli* strain XLI-Blue MRF' before being used on Western blot.

Expression, SDS-PAGE and Western blots. The *E. coli* colony containing pJYH3 was cultured in SOB media, induced by isopropylthio-D-galactoside (IPTG) at a concentration of 2 mM for 10 hours. The recombinant proteins were purified using Ni-NTA resin according to the manufacturer's instruction (Qiagen). The bacterial pellets and the purified recombinant proteins were solubilized in sample buffer and incubated at 37° C. or boiled at 100° C. for 10 minutes. The samples (40 μg per well for whole cell lysates and 5 ug per well for purified 35 kDa major outer membrane protein and recombinant protein) were then analyzed on 10% polyacrylamide gels according to Laemmli (1970). The separated proteins were stained with Coomassie blue for detecting proteins. For Western blots, the proteins were transferred to nitrocellulose membranes (Bio-Rad Laboratories) at 80 volts for 2 hours. Nitrocellulose membranes were then incubated with antiserum against *P. multocida* P-1059 bacterin, then incubated with 1:500 HRP-conjugated anti-chicken IgG (Sigma, St. Louis, Mo.) for 1 hour followed by washing in phosphate buffered saline (PBS). Antigen-antibody complexes on the membrane were visualized by incubation with 3,3'diaminobenzidine (DAB) and urea hydrogen solution prepared using fast DAB tablets (Sigma).

Results

Figure 10A:
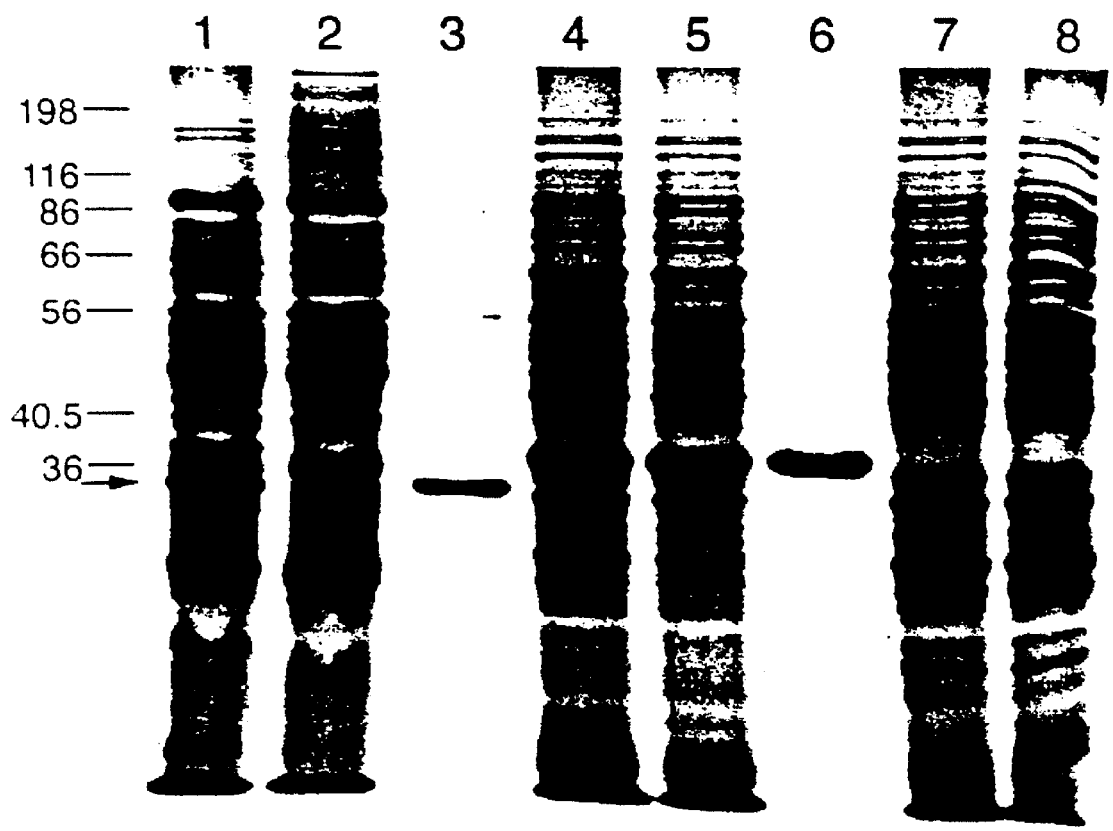
Figure 10B:
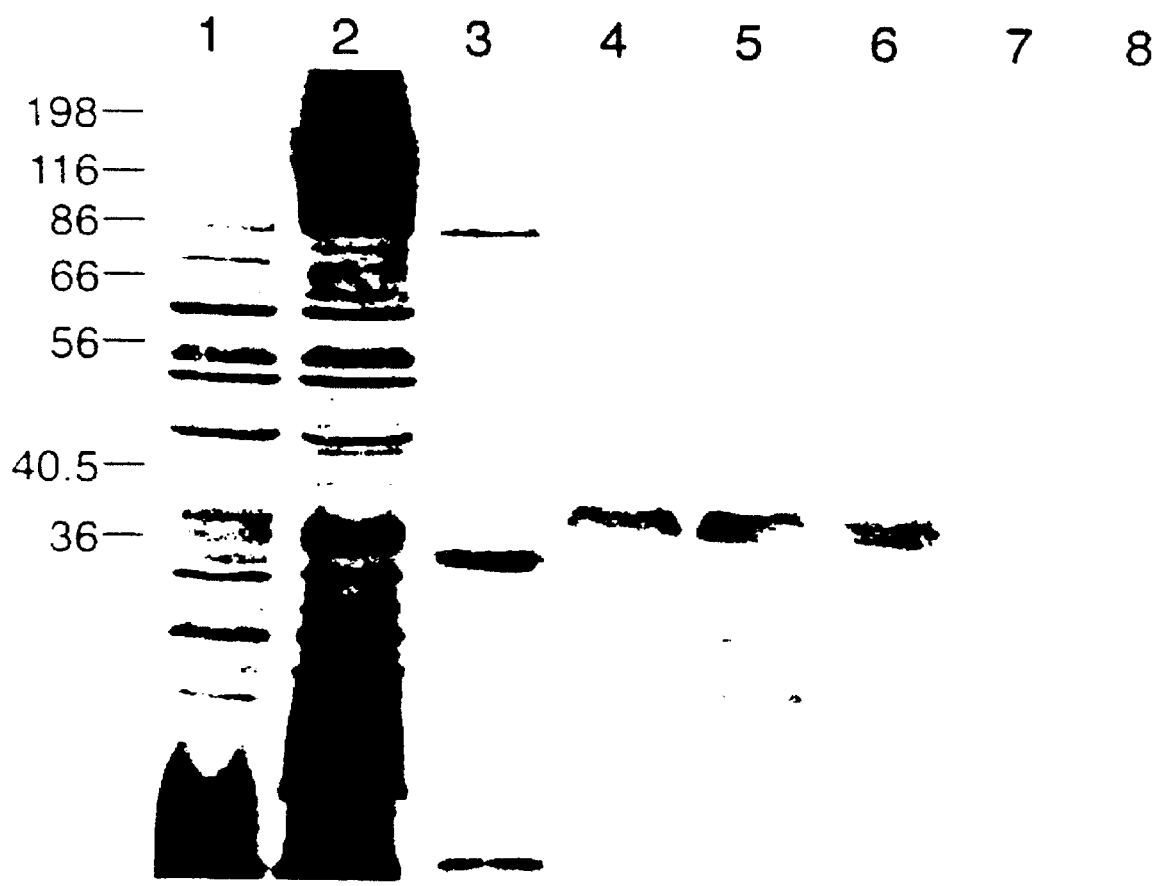

Purification and N-terminal amino acid sequencing of P1059 35 kDa major outer membrane protein. The trimeric or oligomeric form of the major outer membrane protein was significantly purified. But the purified protein still contained a small amount of lipopolysaccharides (LPSS) that was detected by KDO measurement. The whole cell lysate of *P. multocida* P-1059 and the purified major outer membrane protein were analyzed on SDS-PAGE and Western blot (FIG. 10). The 35 kDa major outer membrane protein showed a heat-modifiable property, i.e., the 35 kDa protein disappeared when the samples were not boiled, but a ladder of high molecular mass protein bands between 86 kDa and 210 kDa appeared at the top region of the gel (FIGS. 10A and 10E, lane 1 and lane 2). The arrow indicate the position of 35 kDa major outer membrane protein monomer). The N-terminus of the purified 35 kDa outer membrane protein had the following sequence: A-T-V-Y-N-Q-D-G-T-K-V-D-V-N-G-S-V-R-L-I (SEQ ID NO:17). This N-terminus was almost identical with that of strain X-73 OmpH except at position 17 where there was a valine for P-1059 35 kDa protein and a leucine for X-73 OmpH.

Ionic conductance of purified P-1059 major outer membrane protein. A stepwise increase in ion conductance was observed when purified 35 kDa outer membrane protein was added to one compartment of the chambers (FIG. 13). The distribution of single-channel conductance increments of the purified outer membrane protein in 1.0 M KCl was shown in FIG. 14. The average single channel conductance was 0.67 nS. A total of 91 conductance steps were recorded.

PCR amplification of P-1059 omph gene. *P. multocida* P-1059 omph gene homolog was successfully amplified from genomic DNA using primers derived from *P. multocida* X-73 omph gene. The PCR products were directly sequenced by primer walking in both directions. The DNA sequence of *P. multocida* P-1059 omph gene homolog is shown (FIG. 11). This sequence was further confirmed by the sequence of PCR product amplified using pfu DNA polymerase, which has proofreading function (Stratagene, La Jolla, Calif.). The coding region of omph gene homolog for primary protein was 1029 base pairs (bp) in length. The deduced primary protein is composed of 343 amino acids with a 20 amino acid signal peptide. The mature protein was composed of 323 amino acids with a molecular weight of 35.222 kDa. The predicted molecular mass of the mature protein was very close to that of the 35 kDa major outer membrane protein shown on SDS-PAGE. The deduced amino acid sequence showed 84% identity to *P. multocida* X-73 OmpH (FIG. 12). A similarity search in the GenBank database revealed that the amino acid sequence of *P. multocida* P-1059 OmpH had similarities with other porins of Gram-negative bacteria. The amino acid composition of *P. multocida* P-1059 OmpH was very similar to that of *P. multocida* X-73 OmpH and was typical of nonspecific bacterial porins: a highly negative hydropathy index, high glycine contents, low proline contents and lack of cysteine.

Expression of P-1059 omph gene in *E. coli*. Transformation of recombinant pQE32, which contained *P. multocida* P-1059 omph gene homolog for mature protein, produced about 2,500 colonies. Five colonies were randomly picked for sequence determination. The recombinant plasmid chosen for further analysis was designated as pJYH3. The mature protein gene in pJYH3 was expressed and detected in *E. coli* strain XLI-Blue MRF' (FIG. 15). The *P. multocida* P-1059 OmpH was expressed as a fusion protein with extra amino acids fused at the N-terminus. This fusion protein had a molecular mass of about 37 kDa and was reacted to the antiserum against *P. multocida* P-1059 bacterin (FIG. 10, lanes 4–6). Also the 35 kDa major outer membrane protein of *P. multocida* P-1059 was reacted to the antiserum against purified recombinant protein. Both induced and uninduced *E. coli* harboring pJYH3 produced the recombinant OmpH. This indicated that the T5 promoter in pJYH3 was not tightly controlled.

Discussion

The major outer membrane proteins of some *P. multocida* strains have been reported to show general properties of other bacterial porins. Chevalier et. al. purified the major outer membrane protein, protein H of *P. multocida* serotype D2 strain 7473 and 9222, and characterized protein H as a porin by planar lipid bilayer assay and electron microscopic image assay (1993). Lubke et al. showed that the 35 kDa major outer membrane protein of *P. multocida* serotype A 225 had heat-modifiable properties (1994). Marandi et al. purified a 32 kDa major outer membrane protein, a putative porin of *P. multocida* P210 (serotype D) (1996). The N-terminal amino acid sequences of these outer membrane proteins are very similar. They may belong to the same class of major outer membrane porins of *P. multocida*.

The 35 kDa major outer membrane protein from *P. multocida* P-1059 (serotype 3) was purified and characterized. The 35 kDa protein was shown to be heat-modifiable in SDS-PAGE analysis. Functional assay by planar lipid bilayer technique demonstrated that the 35 kDa protein has pore-forming activity.

Using primers based on cloned *P. multocida* X-73 omph gene sequence, the omph gene homolog from *P. muliocida* P-1059 chromosome DNA was amplified. The deduced amino acid sequence showed 84% identity with *P. multocida* X-73 OmpH. And the deduced N-terminal amino acid sequence matched the N-terminal amino acid sequence of the 35 kDa major outer membrane protein determined by amino acid sequencing. Also, in Western Blot assay the antiserum against recombinant protein reacted to the 35 kDa major outer membrane protein of *P. multocida* P-1059. These results showed that the omph gene homolog in *P. multocida* P-1059 encoded the 35 kDa major outer membrane protein of *P. multocida* P-1059.

The purified 35 kDa major outer membrane protein of *P. multocida* P-1059 and its recombinant protein from *E. coli* were used to immunize the turkeys. Both of them failed to induce consistent protection against homologous strain challenge.

EXAMPLE III

Sequence Analysis of *Pasteurella Multocida* Major Outer Membrane Protein and Application of Synthetic Peptides in Vaccination of Chickens Against Homologous Strain Challenge Materials and Methods Bacterial strains. The strains or serotypes of *P. multocida* used in this study were X-73 (serotype 1), P-1059 (serotype 3), P-1662 (serotype 4), P-1072 (serotype 5), type strains of serotypes 6, 7, 8, 9, 10, 11, 12, 13, 14, 15, 16, and the CU vaccine strain (serotype 3,4). All isolates were obtained from the National Animal Disease Center (Ames, Iowa).

Oligonucleotide synthesis. The oligonucleotides were synthesized by Retrogen Inc. (San Diego, Calif.). Two oligonucleotides based on DNA encoding the N-terminal sequence and noncoding 3' sequence of X-73 omph gene were synthesized for PCR amplification. The sequences of the two primers were as follows:

5'-ACTATGAAAAAGACAATCGTAG-3' (SEQ ID NO:53)

5'-GATCCATTCCTTGCAACATATT-3' (SEQ ID NO:54)

Isolation of *P. multocida* genomic DNA and amplification of OmpH genes bv PCR. *P. multocida* genomic DNAs were isolated using GNOME DNA isolation kit according to the manufacturer's instruction (BIO 101, Inc. La Jolla, Calif.). The isolated genomic DNAs were used for PCR amplification as follows. PCR mixtures consisted of 20 ng of *P. multocida* genomic DNA; 60 pmol of primer A and primer B each; 0.1 mM DNTP, 1.5 mM MgCl, and 2.5 units of Taq DNA polymerase (Boehringer Mannheim, Indianapolis, Ind.) or pfu DNA polymerase (Stratagene, La Jolla, Calif.) in 100 μl of reaction buffer. The amplification reactions were performed on Gene Amp PCR System 9600 (Perkin Elmer Cetus Inc., Norwalk, Conn.) under following conditions: 94° C. for 5 minutes; then 35 cycles each at 94° C. for 15 seconds, 55° C. for 1 minute, 72° C. for 1 minute; and lastly 72° C. for 10 minutes. The PCR products were analyzed on 0.8% agarose gel.

Sequence determination and analvsis. The PCR products were purified using QIAGEN quick PCR purification kit (Oqtagen Inc., Chatsworth, Calif.). The purified PCR products were directly sequenced by the dideoxy-chain termination method (Sanger et al., 1977) using Applied Biosystem Model 373A Version 2.1.0. Sequence analysis was conducted with GCG package (Genetics Computing Groups, Madison, Wis.) and Hitachi DNAsis Pro 3.0 software (Hitachi Software Engineering Co., Ltd., San Bruno, Calif.). Sequence similarity searches were performed using BLAST network service at the National Center for Biotechnology Information (NCBI) (Altshul et al., 1996). Secondary structure predictions were performed using multiple sequence alignment and the following supportive analyses: antigenic index plot (AI)(Jameson et al., 1988), hydrophobic moment analysis (MOM)(Esisenberg et al., 1984), and sided beta-sheet amphiphilicity index analysis (SKD) (Jahnig, 1990). The SKD indices for beta-strand were calculated manually using the equation as described by Jahnig (1990) and the amino acid hydrophobicity indices used were from Kyte and Doolittle (1982).

Synthetic peptides. Single peptides and multiple antigen peptides (MAP) derived from loop 2 and loop 5 of *P. multocida* X-73 OmpH were synthesized using ACT 350 Multiple Peptide Synthesizer (Advanced Chemtech, Louisville, Ky.) at the Molecular Genetics Instrumentation Facility of the University of Georgia (Athens, Ga.). The cyclization of the peptides was achieved by oxidation of free cysteinyl thiol groups as described by Tam and Lu (1980). The sequences of the synthetic peptides are shown in Table 3.

Protection studies using svnthetic peptides in chickens. Five week old specific pathogen free (SPF) chickens were injected intramuscularly with synthetic peptides emulsified in Freund's complete adjuvant (1:1), 100 μg (0.5 ml) per bird for MAP-L2 and MAP-L5, 200 μg (0.5 ml) per bird for Cyclic-L2 and Cyclic-LS. The injections were repeated 2 weeks later (at 7 weeks of age) with the same preparations emulsified in Freund's incomplete adjuvant. One group of chickens injected with X-73 bacterin made as previously described (Wang et al., 1994) and another group of chickens without vaccination were used as positive and negative controls respectively. Fourteen days after the second injection, a blood sample was taken from each bird and the birds were then challenged with 1120 cfu *P. multocida* X-73. The birds were observed for 18 days after challenge and mortalities were recorded.

Enzyme-linked immunosorbent assay (ELISA). Immunoplates (Nunc, VWR Scientific, Bridgeport, N.J.) were coated at 40° C. overnight with 100 ng of the following antigens: MAP-L2, MAP-LS, Cyclic-L2 Cyclic-LS, the whole cell lysates of X-73 and the whole cells of X-73. The plates were washed three times with 0.01 M phosphate buffered saline (PBS) containing 0.05% Tween 20 (pH 7.2), followed by adding 200 μl of blocking buffer (PBS containing 1% bovine serum albumin) and incubated at room temperature for 30 minutes. After washing, 50 μl of antisera serially diluted with blocking buffer was added and incubated at room temperature for 30 minutes. After further washing, 50 μl of 1:5000 diluted rabbit anti-chicken IgG conjugated to horseradish peroxidase (HRP) (Zymed Laboratories, Inc., San Francisco, Calif.) was added and incubated at room temperature for 1 hour. For color development, 100 μl of 3,3',5,5' tetramethylbenzidine (TMB) substrate was added and incubated for 30 minutes. Then 100 μl of 0.25% hydrofluoric acid was added to stop the reaction. Absorbance was read at a wavelength of 630 nm using an ELISA reader (MR650, Dynatech Laboratories, Inc. Alexandria, Va.).

Whole cell ELISA. Whole cell ELISA was performed according to the method of Abdillahi and Poolman (1978). *P. multocida* X-73 was grown in brain heart infusion (BHI) broth at 37° C. overnight. The bacteria were pelleted and washed 3 times with 0.01 M PBS (pH 7.2). After inactivation of the bacteria at 56° C. in a waterbath for 30 minutes, the suspension was adjusted to an absorbance of 0.05 at 620 nm. Then 100 μl of the bacterial suspension in PBS was added into the wells of the immunoplate and allowed to evaporate overnight at 37° C. The subsequent steps were the same as ELISA (above).

Preparation of whole cell lysate of *P. multocida* X-73. Whole cell lysate was made as previously described (Wang et al., 1992).

Results

PCR amplification and sequencing of *P. multocida* omvh genes. omph genes were successfully amplified from all serotypes. A single PCR product with a similar molecular size of approximately 1 kb was obtained from each strain. The PCR products were purified and directly sequenced by the strategy of primer walking in both directions.

Sequence analysis of *P. multocida* omph genes. The coding regions of all omph genes were 954–999 base pairs in length, the deduced mature proteins of OmpH were 318–333 amino acids in length (FIG. 15). The amino acid sequence and compositions of all OmpHs were very similar and were typical of the Gram-negative bacterial porins: highly negative hydropathy index, lack of stretches of hydrophobic residues, high glycine content, low proline content and lack of cysteine (Table 3).

TABLE 3

Synthetic peptides used for immunization.

| Peptide | Sequence |
|---|---|
| MAP-L2 (SEQ ID NO: 45) | SKNVPVQVKDQQGEVVREYEVEKLGNNVHV |
| MAP-L5 (SEQ ID NO: 44) | KYVKQEVEQNPPAAQKVFKDEK |
| Cyclic-L2 (SEQ ID NO: 55) | CSKNVPVQVKDQQGEVVREYEVEKLGNNVHVC |
| Cyclic-L5 (SEQ ID NO: 56) | CKYVKQEVEQNPPAAQKVFKDEKC |

Sequence similarity searches in NCSI database revealed that all OmpH proteins showed sequence similarities to other bacterial porins. The highest similarity was found with *H. influenzae* porin P2 (36–39% identity). Also similarity was found with *E. coli* major porins OmpC, OmpC, OmpF and PhoE (about 30% identity).

Multiple sequence alignment of OmpH amino acid sequences of different serotypes revealed very high homology (72.3% overall identity). Except for some variations in two regions (about 60–80 region, about 200–220 region), other regions of the amino acid sequences were very conserved with only single or a few amino acid substitutions, insertions and/or deletions (FIG. 15). Based on multiple sequence alignment, a phylogenetic tree was established for these 16 OmpH amino acid sequences (FIG. 16). In this phylogenetic tree, serotype 1 and serotype 14, serotype 5 and serotype 16 showed 100% identity, respectively. Serotype 6 and serotype 7, and serotype 10 and serotype 12 showed 99.6% identity, respectively. The group of serotypes 6, 7, 8, 13 were less closely related to the group of serotypes 1, 3, 4, 5, 9, 10, 11, 12, 14, 16 (72.3% identity), in which serotype 8 and serotype 9 are most distantly related. From these comparisons and the phylogenetic tree, the omph genes are evolutionarily conserved among *P. multocida* serotypes.

Secondary structure predictions of OmpHs. According to the crystal structures of four porins (porin of *R. capsulatus*, porin of *R. blastica*, and OmpF and PhoE of *E. coli*), the transmembrane porin is a trimer composed of three identical monomers, and each monomer is a beta-barrel structure consisting of 16 antiparallel transmembrane beta-strands and eight external loops and eight periplasmic turns. A sequence alignment for these four porins revealed that the positions of the 16 antiparallel beta-strands were highly conserved despite the low similarities in their primary amino acid sequences (about 30% identity with each other determined using Maximum Matching program in DNAsis Pro 3.0). Since the OmpHs also showed about 30% identity with these four known porins, it may be possible to use sequence alignment of OmpHs with these four porins with known crystal structure to predict the transmembrane beta-strands of the OmpHs. The omphs of serotype 8 and serotype 9, the two most distantly related OmpHs of *P. multocida*, were chosen as representatives for secondary structure predictions of OmpHs. Beta-strands were predicted in the aligned regions where the corresponding beta-strands of the four known porins existed (FIG. 17). Within these regions, no gaps existed and also no turn predictions existed according to the method of Paul and Rosenbusch (1985). Of the sixteen beta-strands, fourteen beta-strands, S1–S5 and S8–S16, were directly predicted from the sequence alignment. The prediction of the remaining two beta-strands, S6 and S7, was achieved by adjusting the alignment parameters so that the beta-strands 6 and 7 could be aligned together respectively according to the method used by Huang (1995). The other regions containing gaps and sequence variations were assumed to be external loops (L1–L8) or periplasmic turns (T1–T8) (FIGS. 15 and 17).

The above secondary structure predictions were supported by sided beta-sheet amphiphilicity, hydrophobic moment and antigenic index plot analyses of OmpHs (FIG. 18). In the sided beta-sheet amphiphilicity analysis, the amphophilic stretches approximately matched the positions of the predicted beta-strands by sequence alignment. In the hydrophobic moment analysis, most of transmembrane betastrands predicted by hydrophobic moment matched that predicted by sequence alignment. In the antigenic index plots, the minima existed in all of the positions of predicted beta-strands, which means that the predicted beta-strands were least probably exposed on the surface of OmpHs, i.e., they were embedded in the membrane (Jameson et al., 1988). In addition, it was found that the same secondary structures were predicted by sequence alignment in some short sequence repeats identified in OmpH amino acid sequences. For example, there was a repeat in serotype 9 OmpH sequence, G189–Q198 and G223–Q232, in which the amino acids were identical or equivalent. Both of the two short sequences of this repeat were predicted as beta-strands. This further support the accuracy of the previous predictions.

Protection studies. Antibody titers against homologous peptides of X-73 OmpH, whole cell lysate and whole cells of *P. multocida* X-73 were measured by ELISA. The protection index was calculated as the ratio of dead birds to total birds used in a group. The results of protection studies are shown in Table 4.

TABLE 4

ELISA reactivity of antisera induced by vaccination and protection of vaccinated chickens following challenge[A] with X-73.

| | Homologous peptide[C] | | cell lysate of X-73[C] | | Whole cell of X-73[C] | | Dead/Total[D] |
|---|---|---|---|---|---|---|---|
| Antigen[B] | Pre- | Post- | Pre- | Post- | Pre- | Post- | (%) |
| MAP-L2 | 10 | 31623 | 10 | 3872 | 800 | 1600 | 10/10 (100)[A] |
| MAP-L5 | 10 | 10000 | 10 | 707 | 800 | 3200 | 10/10 (100)[A] |
| Cyclic-L2 | 10 | 1000 | 10 | 1000 | 800 | 3200 | 3/10 (30)[B] |
| Cyclic-L5 | 10 | 3000 | 10 | 707 | 800 | 3200 | 10/10 (100)[A] |
| Bacterin | ND[E] | ND[E] | ND[E] | ND[E] | ND[E] | ND[E] | 0/10 (0)[B] |
| None | ND[E] | ND[E] | ND[E] | ND[E] | NE[E] | ND[E] | 10/10 (100)[A] |

[A]Chickens were challenged with 1120 CFU/bird of X-73.
[B]Chickens were vaccinated at 5 weeks and 8 weeks of age.
[C]Antibody titers were measured before (Pre-) and after vaccination (Post-). The sera of a group were pooled and measured two times.
[D]Within a column, values followed by different lowercase superscripts are significantly different ($p < 0.01$).
[E]ND. Not done.

The linear peptides, MAP-L2 and MAP-LS induced very high titers of antibodies against homologous peptides (1000–3000 fold increase), but low titers of antibodies against native protein (OmpH) in the whole cell lysate of X-73 (70–400 fold increase). Cyclic peptides induced low titers against both homologous peptides and native protein (ompH). Both linear MAP peptides and cyclic peptides induced antibodies with similar titers reacting with the bacterial cell surface of X-73 in whole cell ELISA.

Discussion

As membrane proteins, the amino acid sequences of porins are unusual because they contain a high density of charged residues and there are no apparent hydrophobic stretches long enough to span a membrane as an alpha helix (Jap et al., 1990). The secondary structures of porins are exclusively composed of transmembrane anti-parallel beta-strands which are connected by loops and turns to form a beta-barrel (Cowan et al., 1992; Kreusch et al., 1994; Weiss et al., 1992). Porins are generally conserved in a certain bacteria species or family in that they share high homology in primary amino acid sequence and secondary structure. The OmpHs of *P. multocida* shows general properties of Gram-negative bacterial porins in amino acid compositions, hydrophobicity profiles and similarities of predicted secondary structures to known bacterial porins. By sequence alignment, all *P. multocida* omph genes and the encoded proteins (OmpHs) were found to have high homology. Sixteen transmembrane beta-strands were predicted by sequence alignment. This prediction was also supported by the sided beta-sheet amphiphilicity index analysis, hydrophobic moment analysis, the antigenic index plots and the sequence repeat analysis of OmpHs. In these analyses, the antigenic index has not been used before in secondary structure predictions of porins. The antigenic index was originally proposed to predict potential antigenic determinants of proteins (Jameson et al., 1988). The antigenic index plots of the four porins with known crystal structure also matched well with their crystal secondary structure profiles.

The sequence alignment and secondary structure prediction provide valuable information for the design of synthetic peptides as vaccine candidates. Although all the OmpH sequences are generally in high homology, they have some variations in amino acid composition and in the length of the sequence. Most of the variations are confined to two discrete regions. These two regions are correspondingly predicted as the two largest loops, loop 2 and loop 5, which have highest variations in both sequence and length. These two loops may contain serotype specific epitopes which may induce protective antibodies. Peptides in two forms, including linear MAPs and cyclic peptides (Table 3), were synthesized and tested in chickens for their capacity to induce protection. The cyclic peptides were designed to mimic the native conformation of the loops.

Although linear peptides (MAP) induced high titer of antibodies against homologous peptides, the antisera showed low or weak reaction with native protein (OmpH) and no protection was induced in chickens. This indicated that the antisera induced by linear peptides contained none or a very small amount of antibodies which recognized the protective epitopes on the native protein. Polyclonal antisera induced against synthetic peptides probably contains antibodies to a wide range of conformations the peptides may possess in solution. only some of them may recognize the conformational epitopes of the native protein (Altschul et al., 1990).

Cyclic peptides induced low titers of antibodies against homologous peptides but a high proportion of these antibodies, especially antibodies against cyclic-L2, were against native protein because the antibody titers against native protein were similar to the titer against homologous cyclic peptides as shown in Table 4. This indicates that antibodies induced by cyclic peptides recognized epitopes on the native protein. The observation that cyclic-L5 did not induce protection may suggest that loop 5 does not contain protective epitopes. Because all antisera induced by the synthetic peptides reacted positively with the cell surfaces in the whole cell ELISA, L2 and L5 are likely surface exposed. This provides evidence for the confirmation of our previous secondary structure predictions.

Although cyclic-L2 induced a low titer of antibodies against itself and native protein, it was sufficiently immunogenic to induce significant protection without conjugation to a carrier protein, indicating that cyclic-L2 contained both protective B-cell epitopes and T-cell epitopes. T-celi epitopes in cyclic-L2 could be important for inducing immune memory in immunized chickens. it is difficult to explain the relationship between the low antibody titer and the significant protection induced by cyclic-L2. This may be because cyclic-L2 induced functional and conformationally relevant antibodies able to react with OmpH at the cell surface of *P. muliocida* X-73.

References

Abdillahl, H., and T. T. Poolman. Whole-cell ELISA for typing *Neisseria meningitides* with monoclonal antibodies. *FEMS Microbial. Lett.* 48:367–371. 1978.

Adler, B., R. Chancellor, P. Homchampa, M. Hunt, C. Ruffolo, R. Stugnell, and D. Wapling. Immunity and vaccine development in *Pasteurella multocida* infections. *J. Biotechnol.* 44:139–144. 1996.

Altschul, S. F., W. Gish, W. Miller, E. W. Myers, and D. J. Lipman. Basic local alignment search tool. *J. Mol. Biol.* 215:403–410. 1990.

Altschul, S. F., W. Gish, W. Miller, E. W. Myers and D. J. Lipman. Basic local alignment search tool. *J. Mol. Biol.* 215:403–404. 1990.

Ax-non, R. Synthetic peptides as the basis for vaccine design. *Mol. Immunol.* 28:209–215. 1991.

Baalsifud, K. J. Atrophic rhinitis in goats in Norway. *Vet. Rec.* 121:350–353. 1987.

Baba, T. Cell-mediated immune protection in chickens against *Pasteurella multocida*. *Res. Vet. Sci.* 36:225–230. 1984.

Baba, T., T. Ando, and M. Nukina. Effect of bursectomy and thymectomy on *Pasteurella multocida* infection in chickens. *J. Med. Microbiol.* 11:281–288. 1978.

Bairey, M. H. Immune response to fowl cholera antigens. *Am. J. Vet. Res.* 36:575–578. 1975.

Bangham, A. D., J. De Gler, and G. D. Greville. Osmotic properties and water permeability of phospholipid liquid crystals. *Chem. Phys. Lipids.* 1:225–246. 1967.

Benz, R., and R. E. W. Hancock. Mechanism of ion transport through the anion-selective channel of the *Pseudomonas aeruginosa* outer membrane. *J. Gen. Physiol.* 89:275–295. 1987.

Benz, R., K. Janko, and P. Lauger. Formation of large ion-permeable membrane channels by the matrix protein (porin) of *Escherichia coli*. *Biochim. Biophys. Acta* 5111:238–247. 1978.

Benz, R., and K. Bauer. Permeation of hydrophilic molecules through the outer membrane of Gram-negative bacteria. *Eur. J. Biochem.* 176:1–19. 1988.

Benz, R., K. Janko, W. Boos, and P. Lauger. Formation of large ion-permeable membrane channels by the matrix protein (porin) of *Escherichia coli*. *Biochim. Biophys. Acta.* 511:305–319.1978.

Benz, R., and R. E. W. Hancock. Mechanism of ion transport through the anion-selective channel of the Pseudomonas aeruginosa outer membrane.*J. Gen. Physiol.* 89:275–295. 1987.

Benz, R. Structure and function of porins from Gram-negative bacteria. *Annu. Rev. Microbiol.* 42:359–393. 1988.

Benz, R. Uptake of solutes through bacterial outer membranes, p. 397–423. In: J. M. Ghuysen and R. Hakenbeck (eds.), Bacterial Cell Wall. *Elsevier Science B. V.,* Amsterdam. 1994.

Beveridge, T. J. Ultrastructure, chemistry, and function of the bacterial wall. *Int. Rev. Cytology.* 72:229–317. 1981.

Bierer B. W., and W. T. Derieux. Immunologic response of turkeys to an avirulent *Pasteurella multocida* vaccine in the drinking water. *Pout. Sci.* 51:408–416. 1972.

Bierer, B. W., and W. T. Derienx. Immunologic response of turkey poults of various ages to an avirulent *Pasteurella multocida* vaccine in the drinking water. *Poult. Sci.* 54:784–787. 1975.

Birdsell, D. C., and E. H. Cota-Robles. Production and ultrastructure of lysozyme and ethylenediaminetetraacetate-lysozyme spheroplasts of *Escherichia coli*. *J. Bacteriol.* 93:427–437. 1967.

Bording, A., K. Nirmark, and E. Smidt. Field trials with a new genetically engineered vaccine for protection against progressive atrophic rhinitis in pigs. *Acta. Vet. Scand.* 35:155–163. 1994.

Botcher, L., A. Liibke, and E. Hellmann. In vitro binding of *Pasteurella multocida* cell wall preparations to tracheal mucus of cattle and swine and to a tracheal epithet cell wall preparation of cattle. *Zentralbl. Veterinarmed. B.* 38:721–730. 1991.

Brey B. W., and W. T. Derieux. Immunologic response of turkeys to an avirulent *Pasteurella multocida* vaccine in the drinking water. 2. Duration of immunity. *Pout. Sc.* 51:1402–1408. 1972.

Brogden, K. A., and P. A. Rebers. Serologic examination of the Westphal-type lipoppolysaccharides of *Pasteurella multocida*. *Am. J. Vet. Res.* 39:1680–1682. 1983.

Brogden, K. A., K. R. Rhoades, and K. L. Heddleston. A new serotype of *Pasteurella multocida* associated with fowl cholera. *Avian Dis.* 22;185–195. 1978.

Brogden, K. A., and R. B. Rimler. Lysates of Turkey grown *Pasteurella multocida*: partial solubilization of the cross-protection factor(s). *Am. J. Vet. Res.* 43:1781–1785. 1982.

Brogden, K. A., and R. B. Rimler. Lysates of Turkey grown *Pasteurella multocida*: effects of solubilizing agents on the Immunologic properties of membrane vesicles. *Am. J. Vet. Res.* 44:428–432. 1983.

Burns, J. L., and A. L. Smith. A major outer membrane protein functions as a porin in *Haemophilus influenzae*. *J. Gen. Microbiol.* 133:1273–1277. 1987.

Cameron, C. M., and F. J. Bester. The inefficacy of polivalent *Pasteurella multocida* vaccine for sheep. Onderstepoort. *J. Vet. Res.* 50:101–104. 1983.

Carbonetti, N. H., and P. F. Sparling. Molecular cloning and characterization of the structural gene for protein I, the major outer membrane protein of *Neisseria gonorrhoeae*. *Proc. Natl. Acad. Sci. USA*. 84:9084–9088. 1987.

Carpenter, T. E., K. P. Snipes, D. Wallis, and R. H. McCapes. Epidemiology and financial impact of fowl cholera in turkeys: A retrospective analysis. *Avian Dis.* 32:16–23. 1988.

Carter, G. R. Studies on *Pasteurella multocida*. 1. A hemaaglutination test for identification of serological types. *Am. J. Vet. Res.* 16:481–484. 1955.

Chanter, N., and J. M. Rutter. Colonization by *Pasteurella multocida* in atrophic rhinitis of pigs and immunity to the osteolytic toxin. *Vet. Micobiol.* 25:253–265. 1990.

Chanter, N., J. M. Rutter, and A. Mackenzie. Partial purification of an osteolytic toxin from *Pasteurella multocida*. *J. Gen. Microbiol.* 132:1089–1097. 1986.

Chen, R., C. Kramer, W. Schmidmay, U. Chen-Schmelsser, and U. Henning. Primary structure of major outer membrane protein I (OmpF protein, porin) of *Escherichia coli*. *Blr. Biochem. J.* 203:33–43. 1980.

Chevalier, G., H. Duclohier, D. Thomas, E. Shechter, and H. Wroblewski. Purification and characterization of protein H, the major porin of *Pasteurella multocida*. *J. Bacteriol.* 175:266–276. 1993.

Choi, Kim-K., S. K. Maheswaran, L. J. Felice, and T. W. Molitoi. Relationship between the iron regulated outer membrane proteins and the outer membrane proteins of in vivo grown *Pasteurella multocida*. *Vet. Microbiol.* 28:75–92. 1991.

Choi, K. H., S. K. Maheswaran, and L. J. Felice. Characterization of outer membrane protein-enriched extracts from *Pasteurella multocida* isolated from turkeys. *Am. J. Vet. Res.* 50:676–683. 1989.

Christodoulides, M., B. T. McGuinness and E. Heckels. Immunization with synthetic peptides containing epitopes of the class I outer membrane protein of Neisseria meningitides: production of bactericidal antibodies on immunization with a cyclic peptide. *J. Gen. Microbiol.* 139:1729–1738. 1993.

Collier, J. R. Significance of bacteria in bovine respiratory disease. *J. Am. Vet. Med. Assoc.* 153:1645–1651. 1968.

Cowan, S. W., T. Schirmer, G. Rummel, M. Stelert, R. Ghosh, R. A. Pauptit, J. Jansonius, and J. P. Rosenbusch. Crystal structure explain functional properties of two *E. coli* porins. *Nature* 358:727–733. 1992.

DeAngelis, P. L. Enzymological characterization of the *Pasteurella multocida* hyaluronic acid synthase. *Biochemistry*. 35:9768–9771.1996.

Delamarche, C., F. Manoha, G. Behar, R. Houlgatte, U. Hellman, and H. Wrobkewski. Characterization of the *Pasteurella multocida* skp and FirA genes. *Gene* 161:39–43. 1995.

Dick, J. W., and J. W. Johnson. Fowl cholera immunity in broiler breeder chickens determined by the enzyme-linked immunosorbent assay. *Avian Dis*. 29:706–714. 1985.

DiGiacomo, R. F., B. J. Deep, W. E. Giddens, D. L. Bernard, and M. M. Chengappa. Atrophic rhinitis in New Zealand white rabbits infected with *Pasteurella multocida. Am. J. Vet. Res*. 50:1460–1465.1989.

Dominick, M. A. and R. B. Rimler. Turbinate atrophy in gnotobiotic pigs intranasally inoculated with protein toxin isolated from type D *Pasteurella multocida. Am. J. Vet. Res*. 47:1532–1536. 1986.

Drezeniek, R., W. Scharmann, and E. Balke. Neuraminidase and N-acetylneuraminate pyruvate-lyase of *Pasteurella multocida. J. Gen. Microbiol*. 72:357–368. 1972.

Dua, S. K., and S. K. Maheswairan. Studies on *Pasteurella multocida* VI. Nature of systemic immunity and analysis of the correlation between levels of immunity induced by various fowl cholera vaccines and protection against challenge. *Avian Dis*. 22:748–764. 1978.

Dubreuil, J. D., L. Gilbert, and M. Jacques. Cell surface characteristics and virulence in mice of *Pasteurella multocida. Int. J. Med. Microbiol. Virol. Parasitol. Infect. Dis*. 276:366–373.

Eisenberg, D., E. Schwarz, M. Komaromy, and R. Wall. Analysis of membrane and surface protein sequences with the hydrophobic moment plot. *J. Mol. Biol*. 179:125–142. 1984.

Elling, F., K. B. Pedersen, P. Hogh, and N. T. Foged. Characterization of the dermal lesions induced by a purified protein from toxigenic *Pasteurella multocida*. APMIS. 96:50–55. 1988.

Erler, W., K. D. Flossman, H. Feist, and S. Jacob. Diestrukturelemente in den lipopolysacchariden des chemotypes IV von *Pasteurella multocida. Z. Allg. Mikrobiol*. 21:569–579. 1981.

Felix, R., H. Fleisch, and P. L. Frandsen. Effect of *Pasteurella multocida* toxin on bone resorption in vitro. *Infect. Immun*. 60:4984–4994. 1992.

Ferenci, T. From sequence alignment to structure prediction: the case of the OmpF porin family. *Mol. Microbiol*. 14(i): 188–189. 1994.

Ficken, M. D. and R. J. Barnes. Acute airsacculitis in turkeys inoculated with *Pasteurella multocida. Vet. Pathol*. 26:231–237. 1989.

Foged, N. T. *Pasteurella multocida* toxin, Ch 2. APMIS. Supplerhentum No. 25. 100:11–27. 1992.

Foged, N. T. Quantitation and purification of the *Pasteurella multocida* toxin by using monoclonal antibodies. *Infect. Immun*. 56:1901–1906. 1988.

Foged, N. T., K. B. Pedersen, and F. Elling. Characterization and biological effects of the *Pasteurella multocida* toxin. FEMS Microbol. Lett. 43:45–51. 1987.

Frederiksen, W. A Note on the name of *Pasteurella multocida*, p. 35–36. In: C. Adlam and J. M. Rutter (eds.), Pasteurella and Pasteure-Llosis. Academic Press, Inc. San Diego. 1989.

Frederiksen, W. Pasteurellosis of Man, p. 303–320. In: C. Adlam and J. M. Rutter (eds.), Pasteurella and Pasteurellosis. Academic Press, Inc., San Diego. 1989.

Friedlander, R. C., L. D. Olson, and E. L. McCune. Comparison of live avirulent M-9, Minnesota, and CU fowl cholera vaccines. *Avian Dis*. 35:251–256. 1991.

Frymus, T., E. Muller, B. Franz, and K. Petzold. Protection by toxoid-induced antibody of gnotobiotic piglets challenged with the dermonecrotic toxin of *Pasteurella multocida. J. Vet. Med. B*. 36:674–680. 1989.

Gerhardt, P., R. G. E. Murray, R. N. Costilow, E. W. Nester, W. A. Wood, N. R. Krieg and G. B. Phillips (eds.), Manual of Methods for General Bacteriology. American Society for Microbiology, Washington, DC.

Gilleland, Jr., H. E., M. G. Parker, J. M. Matthews, and R. D. Berg. Use of a purified outer membrane protein F (porin) preparation of *Pseudomonas aeruginosa* as a protective vaccine in mice. *Infect. Immun*. 44:49–54. 1984.

Gilleland, Jr., H. E., L. B. Gilleland, and J. M. Matthews-Greer. Outer membrane protein F preparation of *Pseudomonas aerugiznosa* as a vaccine against chronic pulmonary infection with heterologous immunotype strains in a rat model. *Infect. Immun*. 56:1017–1022. 1988.

Gilleland, Jr., H. E., L. B. Gilleland, and J. M. Mathews-Greer. Outer membrane protein F preparation of *Pseudomonas aeruginosa* as vaccine against chronic pulmonary infection with heterologous immunotype strains in a rat model. *Infect. Immun*. 56:1017–1022. 1988.

Glisson, J. R., M. D. Contreras, I-H. N. Cheng, and C. Wang. Cross-protection studies with *Pasteurella multocida* bacterins containing bacteria propagated in ion-depleted medium. *Avian Dis*. 37:1074–1079. 1993.

Glisson, J. R., and I-H. N. Cheng. In vivo antigen expression by *Pasteurella multocida. Avian Dis*. 35:392–396. 1991.

Gloricso, J. C., G. W. Jones, H. G. Rush, L. J. Pentler, C. A. Darif, and J. E. Coward. Adhesion of type A *Pasteurella multocida* to rabbit pharyngeal cells and its possible role in rabbit respiratory tract infections. *Infect. Immun*. 35:1103–1109. 1982.

Gulig, P. A., and E. J. Hansen. Co-precipitation of lipopolysaccharide and the 39000-molecular-weight major outer membrane protein of *Haemophilus influenzae* type b by lipopolysaccharide-directed monoclonal antibody. *Infect. Immun*. 49:819–827.1985.

Hall, W. J., K. L. Heddleston, D. H. Legenhausen, and R. W. Hughes. Studies on pasteurellosis. 1. A new species of *Pasteurella multocida* encountered in chronic fowl cholera. *Am. J. Vet. Res*. 16:598–604. 1985.

Hancock, R. E. W. Model membrane studies of porin function, p. 187–225. In: M. Inouye (ed.), Bacterial Outer Membranes as Model Systems. John Wiley & Sons, New York. 1986.

Hancock, R. E. W., and R. Benz. Demonstration and chemical modification of a specific phosphate binding site in the phosphate-starvation-inducible outer membrane porin protein P of *Pseudomonas aeruginosa. Biochim. Biophys. Acta* 860:669–707.1986.

Hancock, R. E. W., D. N. Karunaratne and C. BerneggerEgli. Molecular organization and structural role of outer membrane macromolecules, p. 263–279. In: J. M. Ghuysen and R. Hakenbeck (ed.), Bacterial Cell Wall. Elsevier Science B. V., Amsterdam. 1994.

Hansen, E. J., S. E. Elelzel, K. Orth, C. R. Moomaw, J.II. Radolf, and C. A. Slaughter. Structural and antigenic conservation of the P2 porin protein among strains of *Haemophilus influenzae* type b. *Infect. Immun*. 57:3270–3275.1989.

Hansen, E. J., and F. R. Gonzales. 1988. Cloning of the gene encoding the major outer membrane protein of *Haemophilus influenzae* type b. *Infect. Immun*. 56:2709–2716.

Hansen, L. M., and D. C. Hirsh. Serum resistance is correlated with encapsulation of avian strain of *Pasteurella multocida*. *Vet. Microbiol.* 21:177–184. 1989.

Hanson, R. S., and J. A. Phillips. 1981. Chemical composition. p. 328–364. In: P. Gerhardt, R. G. E., Murray, R. N. Costilow, E. W. Nester, W. A. Wood, N. R. Krieg and G. B. Phillips (eds.), Manual of Methods for General Bacteriology. American Society for Microbiology, Washington, D.C.

Harmon, B. G., J. R. Blisson, K. S. Latimer, W. L. Steffens, and J. C. Nunnally. Resistance of Pasteurella multocida A:3,4 to phagocytosis by turkey macrophages and heterophils. *Am. J. Vet. Res.* 52: 1507–1511. 1991.

Heddleston, K. L., J. E. Gallagher, and P. A. Rebers. Fowl cholera immune response in turkeys. *Avian Dis.* 14:626–635. 1970.

Heddleston, K. L., J. E. Gallagher, and P. A. Rebers. Fowl cholera: Gel diffusion preca-pitin test for serotyping *Pasteurella multocida* from avian species. *Avian Dis.* 16:925–936. 1972.

Heddleston, K. L., and P. A. Rebers. Fowl cholera: Cross-immunity induced in turkeys with formalin-killed in vivo-propagated *Pasteurella multocida*. *Avian Dis.* 16:578–586. 1972.

Heddleston, K. L., and P. A. Rebers. Fowl cholera bacterins: Host-specific cross-immunity induced in turkeys with *Pasteurella multocida* propagated in embryonating turkey eggs. *Avian Dis.* 18:213–219. 1974.

Heddleston, K. L., and P. A. Rebers. Properties of free endotoxin from *Pasteurella multocida*. *Am. J. Vet. Res.* 36:573–574. 1975.

Heddleston, K. L., P. A. Rebers, and A. E. Ritchie. Immunizing and toxic properties of particulate antigens from two immunogenic types of *Pasteurella multocida* of avian origin. *J. Immun.* 96:124–133.1966.

Heddleston, K. L., L. P. Walko, and P. A. Rebers. Dissociation of a fowl cholera strain of *Pasteurella multocida*. *Avian Dis.* 8:649–657. 1964.

Hein, H.-G., J. Kyngdon, and T. Ferenci. Sequence determinants in the lamb gene of *Escherichia coli*. influencing the binding and pore selectivity of malto porin. *Gene.* 53:287–292. 1987.

Hirsh, D. C., L. D. Martin, and K. R. Rhoades. Resistance plasmids of *Pasteurella multocida* isolated from turkeys. *Am. J. Vet. Res.* 46:1490–1497. 1985.

Hofacre, C. L., and J. R. Glisson. A serotypic survey of *Pasteurella multocida* isolated from poultry. *Avian Dis.* 30:632–633. 1986.

Hofacre, C. L., J. R. Glisson, and S. H. Kleven. Evaluation of *Pasteurella multocida* mutants of low virulence. II. Immunologic response of turkeys. *Avian Dis.* 33:275–278. 1989.

Hofacre, C. L., J. R. Glisson, S. H. Kleven, J. Brown, and G. N. Rowland. Evaluation of *Pasteurella multocida* mutants of low virulence. 1. Development and pathogenicity. *Avian Dis.* 33:270–274. 1989.

Hofacre, C. L., J. E. Glisson, and S. H. Kleven. Comparison of vaccination protocols of broiler breeder hens for *Pasteurella multocida* utilizing enzyme-linked immunosorbent assay and virulent challenge. *Avian Dis.* 31:260–263. 1987.

Hu, S. P., L. J. Feoice, V, Sivanandan, and S. K. Maheswaran. Siderophore production by *Pasteurella multocida*. *Infect. Immun.* 54:804–810. 1986.

Huang, H., and R. E. W. Hancock. The role of specific surface loop regions in determining the function of the imipenem-specific pore protein OprD of *Pseudomonas aeruginosa*. *J. Bacteriol.* 178:3085–3090. 1996.

Huang, H., D. Jeanteur, F. Pattus and R. E. W. Hancock. Membrane topology and site-specific mutagenesis of *Pseudomonas aeruginosa* porin OprD. *Mol. Microbiol.* 16:931–941. 1995.

Ifeanyi, F. I., and W. E. Bailie. Passive protection of mice with antiserum to neuraminidase from *Pasteurella multocida* serotype A:3. *Vet. Res. Commun.* 16:97–105. 1992.

Ikeda, J. S., and D. C. Hirsh. Antigenically related iron-regulated outer membrane proteins produced by different somatic serotypes of *Pasteurella multocida*. *Infect. Immun.* 56:2499–2502. 1988.

Illina, Z. M., and M. 1. Zasukhin. Role of Pasteurella toxin in the pathogenesis of infectious atrophic rhinitis. Sb.Nauchn. Rab. Sib. Nauchn. Issled. *Vet. Inst. Omsk.* 25:76–86. 1975.

Isibasi, A., V. Ortiz-Navarrete, J. Paniagua, R. Pelayo, C. Gonzales, J. A. Garcia, and J. Kumate. Active protection of mice against *Salmonella typhi* by immunization with strain-specific porins. *Vaccine.* 10:811–813. 1992.

Isibasi, A., V. Ortiz, M. Vargas, J. Paniagua, C. Gonzalez, J. Moreno, and J. Kumate. Protection against Salmonella typhi infection in mice after immunization with outer membrane proteins isolated from *Salmonella typhi* 9,12, d,vi. *Infect. Immun.* 56:2953–2959. 1988.

Jacques, M., M. Kobisch, M. Belangeit, and F. Dugal. Virulence of capsulated and noncapsulated isolates of *Pasteurella multocida* and their adherence to porcine respiratory tract cells and mucus. *Infect. Immun.* 61:4785–4792. 1993.

Jacques, M., and B. Foiry. Electron microscopic visualization of capsular material of *Pasteurella multocida* types A and D labeled with polycationic ferritin. *J. Bacteriol.* 169:3470–3472. 1987.

Jahnig, F. Structure predictions of membrane proteins are not that bad. *Trends Biochem. Sci.* 15:93–95. 1990.

Jameson, B. A. and H. Wolf. The antigenic index: a novel algorithm for predicting antigenic determinants. CA-DIOS. 4:181–186. 1988.

Jap, B. K., and P. T. Walian. Biophysics of the structure and the function of porins. *Quart. Rev. Biophys.* 23:367–403. 1990.

Jeanteur, D., J. H. Lakey, and F. Pattus. The bacterial porin superfamily: sequence alignment and secondary structure prediction. *Mol. Microbiol.* 5: 2153–2164. 1991.

Jeanteur, D., J. H. Lakey, and F. Pattus. The porin superfamily: diversity and common features, p. 363–380. In: J. M. Ghuysen and R. Hakenbeck (eds.), Bacterial Cell Wall. Elsevier Science B. V., Amsterdam. 1994.

Kamp, E. M., and T. G. Kimman. Induction of nasal turbinate atrophy in germ free pigs, using *Pasteurella multocida* as well as bacterin free crude and purified dermonecrotic toxin of *P. multocida*. *Am. J. Vet. Res.* 49:1844–1849. 1988.

Kamp, E. M., P. J. van der Heijden, and B. T. Tetenburg. Purification of a heat labil dermonecrotic toxin from culture fluid of *Pasteurella multocida*. *Vet. Microbiol.* 13:235–248. 1987.

Kamps, A. M. I. E., E. M. Kamp, and M. A. Smits. Cloning and expression of the dermonecrotic toxin gene of *Pasteurella multocida* ssp. multocida in *Escherichia coli*. FEMS Microbiol. Lett. 67:187–190. 1990.

Kasten, R. W., L. M. Hansen, J. Hinojoza, D. Bieber, W. W. Ruehl, and D. C. Hirsh. *Pasteurella multocida* produces a protein with homology to the P6 outer membrane protein of *Haemophilus influenzae*. *Infect. Immun.* 63:989–993. 1995.

Knox, K. W., and R. V. S. Bain. The antigens of *Pasteurella multocida* type I: I. capsule polysaccharides. *Immunology* 3:352–362. 1960.

Kreusch, A., A. Neubuser, E. Schiltz, J. Weckesser, and G. E. Schulz. Structure of the membrane channel porin from *Rhodopseudomonas blastica* at 2.OA resolution. *Protein Sci.* 3:58–63. 1994.

Kyte, J. and R. F. Doolittle. A simple method for displaying the hydropathic character of a protein. *J. Mol. Biol.* 157:105–132. 1982.

Laemmli, U. K. Cleavage of structural proteins during the assembly of the head of bacteriophage T4. *Nature.* 227:680–685. 1970.

Lambden, P. R., Robetson, J. N. and P. J. Watt. The preparation and properties of α-pili and β-pili from variants of *Neisseria gonorrhoeae* P9. *J. Gen. Microbiol.* 124:109–117. 1981.

Lax, A. J., and N. Chanter. Cloning of the toxin gene from *Pasteurella multocida* and its role in atrophic rhinitis. *J. Gen. Microbiol.* 136:81–87. 1990.

Lee, M. D., and R. E. Wooley. The effect of plasmid acquisition on potential virulence attributes of *Pasteurella multocida*. *Avian Dis.* 39:451–457. 1995.

Lee, M. D., R. E. Wooley, and J. R. Glisson. Invasion of epithelial cell monolayers by turkey strains of *Pasteurella multocida*. *Avian Dis.* 38:72–77. 1994.

Lee, M. D., R. E. Wooley, J. R. Glisson, and J. Brown. Comparison of *Pasteurella multocida* serotype 3, 4 isolates from turkeys with fowl cholera. *Avian Dis.* 32:501–508. 1988.

Lowry, O. H., N. J. Rosebrough, A. L. Farr, and R. J. Randall. Protein measurement with the Pholin phenol reagent. *J. Bio. Chem.* 193:265–267. 1951.

Lu, Y. S., S. J. Afendis, and S. P. Pakes. Identification of immunogenic outer membrane proteins of *Pasteurella multocida* 3:A in rabbits. *Infect. Immun.* 56:1532–1537, 1988.

Lu, Y. S., L. W. Gerrity, S. J. Afendis, L. Watkins, and S. P. Pakes. Distribution of a monoclonal antibody recognized protective protein immunogen on the outer membranes of *Pasteurella multocida* rabbit isolates. *J. Clin: Microbiol.* 26:1326–1330. 1988.

Lu, Y. S., W. C. Lai, S. P. Pakes, L. C. Nie. A monoclonal antibody against a *Pasteurella multocida* outer membrane protein protects rabbits and mice against pasteurellosis. *Infect. Immun.* 59:172–180. 1991.

Lu, Y. S., W. C. Lai, S. P. Pakes, and C. Stefanu. The outer membrane of *Pasteurella multocida* 3:A protects rabbits against homologous challenge. *Infect. Immun.* S9:4517–4523. 1991.

Lu, Y. S., S. P. Pakes, L. Massey. Hyperimmune serum from rabbits immunized with potassium thiocyanate extract of *Pasteurella multocida* protect against homologous challenge. *J. Clin. Microbiol.* 25:2173–2180. 1987.

Lubke, A., L. Hartmann, W. Schroder, and E. Hellamann. Isolation and partial characterization of the major protein of outer membrane of *Pasteurella haemolvtica* and *Pasteurella multocida. Int. J Med. Microbiol. Virol. Parasitol. Infect. Dis.* 281:45–54. 1994.

Lubke, A., L. Hartmann, W. Schroder, and E. Hellmann. Isolation and partial characterization of the major protein of one outer membrane of *Pasteurella haemolytica* and *Pasteurella multocida. Int. J Med. Microbiol. Virol. Paresitol. Infect. Dis.* 28:45–54. 1994.

Luckey, M., and H. Nikaido. Specificity of-diffusion channels produced by lambda phage receptor protein of *Escherichia coli. Proc. Natl. Acad Sci. USA.* 77:165–171. 1980.

Lugtenberg, B., and L. van Alphen. Molecular architecture and functioning of the outer membrane of *Escherichia coli* and other Gram-negative bacteria. *Biochim. Biophys. Acta.* 737:51–115. 1983.

Lugtenberg, B., R. van Boxtel, D. Evenberg, M. de Jong, P. Storm, and J. Frik. Biochemical and immunological characterization of cell surface proteins of *Pasteurella multocida* strains causing atrophic rhinitis in swine. *Infect. Immun.* 52:175–182. 1986.

Lugtenberg, B., R. van Boxtel, and M. de Jong. Atrophic rhinitis of swine: correlation of *Pasteurella multocida* pathogenicity with membrane protein and lipopolysaccharide patterns. *Infect. Immun.* 46:48–54. 1984.

Maheswaran, S. K., and E. S. Thies. Influence of encapsulation on phagocytosis of *Pasteurella multocida* by bovine neutrophils. *Infect. Immun.* 26:76–81. 1979.

Makela, P. H., N. Kuusi, M. Nurminen, H. Saxen, and M. Valtonen. 1982. Bacterial vaccines. p. 360–365. In Weinstein, L., B. N. Fields, J. B. Robbins, J. C. Hill, and J. C. Sadoff (eds.), Seminars in infectious disease IV, Thieme-Stratton, Inc., New York.

Mannheim, W., and Carter, G. R. Family III. Pasteurellaceae Pohl 1981, 382. p. 550–558. In: N. R. Krieg and J. G. Holt (eds.), Bergey's Manual of Systematic Bacteriology. Vol. 1. Williams and Wilkins Co., Baltimore/London. 1984.

Manning, P. J., M. A. Naasz, D. Delong, and S. L. Leary. Pasteurellosis in laboratory rabbits: Characterization of lipopolysaccharides of *Pasteurella multocida* by polyacrylamide gel electrophoresis, immunoblot techniques, and enzyme-linked immunosorbent assay. *Infect. Immun.* 53:460–463. 1986.

Manoha F, G. Chevaliar, H. Wroblewski, and C. Delamarche. Cloning and expression of two *Pasteurella multocida* genes in *Escherichia coli. Biochemie* 76:9–14. 1994.

Marandi, V. M., J. D. Dubruil, and K. R. Mittal. The 32 kDa major outer-membrane protein of *Pasteurella multocida* capsular serotype D. *Microbiol.* 142:199–206. 1996.

Marjatta, N., S. Butcher, I. I-Heikkila, E. Wahistrom, S. Muttilainen, K. R-Nyman, M. Sarvas, and P. H. Makela. The class 1 outer membrane protein of *Neisseria meningitides* produced in *Bacillus subtilis* can give rise to protective immunity. *Mol. Microbiol.* 6:2499–2506. 1992.

Marshall, M. S. Development of an attenuated fowl cholera-vaccine. Master's thesis. Brigham Young University, Provo, Utah. p. 1–67. 1981.

Marshall, M. S., R. A. Robinson, and M. M. Jensen. Use of an enzyme-linked immunosorbent assay to measure antibody responses in turkeys against *Pasteurella multocida. Avian Dis.* 25:964–971. 1981.

Matsui, K., and T. Arai. Protective immunities induced by porins from mutant strains of *Salmonella typhimurium. Microbiol. Immunol.* 34:917–927. 1990.

Matsumoto, M., J. G. Strain, and H. N. Engel. The fate of *Pasteurella multocida* after intratracheal inoculation into turkeys. *Poult. Sci.* 70:2259–2266. 1991.

Matsumoto, M., and J. G. Strain. Pathogenicity of *Pasteurella multocida*. its variable nature demonstrated by in vivo passages. *Avian Dis.* 37:781–785. 1993.

Matthews-Greer, J. M-, D. E. Robertson, L. B. Gilleland, and 14. E. Gilleland, Jr. *Pseudomonas aeruginosa* outer membrane protein F produced in *Escherichia coli* retains vaccine efficacy. *Curr. Microbiol.* 20:171–175. 1990.

McGuinness, B., A. K. Barlow, I. N. Clarke, J. E. Faxley, A. Anilionis, J. T. Poolman, and J. E. Heckels. Comparative sequence analysis of the class I protein gene (pora) from three strains of *Neisseria meningitides*: synthetic peptides define the epitopes responsible for serosubtype specificity. *J. Exp. Med.* 171:1871–1882. 1990.

Miura, T., and S. Mizushima. Separation by density centrifugation of two types of membranes from spheroplast membrane of *Escherichia coli*. K12. *Biochim. Biophys. Acta*. 150:156–164. 1968.

Mosra, R., and S. Benson. Isolation and characterization of OmpC porin mutants with altered pore properties. *J. Bacteriol*. 170:528–533. 1988.

Mullan, P. B., and A. J. Lax. *Pasteurella multocida* toxin is a mitogen for bone cells in primary culture. *Infect. Immun*. 64:959–965. 1996.

Muttilainen, S., I. I-Heikkila, E. Wahlstrom, M. Nurminen, P. H. Makela, M. Sarvas. The *Neisseria meningitides* outer membrane protein Pi produced in *Bacillus subtilis* and reconstituted into phospholipid vesicles elicits antibodies to native Piepitopes. *Microb. Pathogen*. 18:423–436. 1995.

Nakae, T. Outer membrane of Salmonella. Isolation of protein complex that produces transmembrane channels. *J. Biol. Chem*. 251:2176–2178. 1976.

Nakae, T., and H. Nikaido. Outer membrane as a diffusion barrier in *Salmonella typhimurium*. *J. Riol. Chem*. 250:7359–7365. 1975.

Nakai, T., A. Sawata, M. Tsuji, Y. Samejlma, and K. Kume. Purification of dermonecrotic toxin from a sonic extract of *Pasteurella multocida* SP-72 serotype D. *Infect. Immun*. 46:429–434. 1984.

Nikaido, H. Nonspecific transport through the outer membrane p. 361–407. In: M. Inouye (ed.), Bacterial Outer Membranes. Wiley, New York. 1979.

Nikaido, H. Proteins forming large channels from bacterial and mitochondrial outer membranes: porins and phage lambda receptor protein. *Methods Enzymol*. 97:85–100. 1983.

Nikaido, H., and E. Y. Rosenberg. Effect of solute size on diffusion rates through the transmembrane pores of the outer membrane of *Escherichia coli*. *J. Gen. Physiol*. 77:121–135. 1981.

Nikaido, H., and E. Y. Rosenberg. Porin channels in *Escherichia coli*.: Studies with liposomes reconstituted from purified proteins. *J. Bacteriol*. 153:241–252. 1983.

Nikaido, H., and M. Vaara. Molecular basis of bacterial outer membrane permeability. *Microbiol. Rev*. 49:1–32. 1985.

Nakamura, K., and S. mizushima. Effects of heating in dodecyl sulfate solution on the conformation and electrophoretic mobility of isolated major outer membrane proteins from *Escherichia coli*.KI2. *J. Biochem*. 80:1411–1422. 1976.

Nurminen M., S. Butcher, 1. Idanpaan-Heikkila, E. Wahlstafom, S. Muttilainen, K. Runeberg-Nyman, M. Sarvas, and P. H. Makela. The class I outer membrane protein of *Neissersa meningitides* produced in *Bacillus subtilis* can give rise to protective immunity. *Mol. Microbiol*. 6:2499–2506. 1992.

Ochman, H., A. S. Gerber and D. L. Hartl. Genetic applications of an inverse polymerase chain reaction. *Genetics* 120:621–623. 1988.

Ogunnarlwo, J. A., J. Alcantara, and A. D. Schryvers. Evidence for non-siderophone-meflated acquisition of transferrin-bound iron by *Pasteurella multocida*. *Microb. Pathogen*. 11:47–56. 1991.

Olson, L. D., and G. T. Schlink. Onset and duration of immunity and minimum dosage with CU cholera vaccine in turkeys via drinking water. *Avian Dis*. 30:87–92. 1986.

Osborne, J. J., and R. Munson. Separation of the inner (cytoplasmic) and outer membranes of Gram-negative bacteria. *Methods Enzymol*. 31:642–653. 1974.

Pandit, K. K., and J. E. Smith. Capsular hyaluronic acid in *Pasteurella multocida* type A and its counterpart in type. D. *Res. Vet. Sci*. 54:20–24. 1993.

Pau, C., and T. P. Rosenbusch. Folding patterns of porin and bacteriorhodopsin. *EMBO J*. 4:1593–1597. 1985.

Penn, C. W., and L. K. Nagy. Isolation of protective, non-toxic capsular antigen from *Pasteurella multocida*, type B and E. *Res. Vet. Sci*. 20:90–96. 1976.

Pennings, A. M. M. A., and P. K. Storm. A test invero cell monolyers for toxin production by strains of *Pasteurella multocida* isolated from pigs suspected of having atrophic rhinitis. *Vet. Microbiol*. 9:503–508. 1984.

Pestana de Castro, A. F., P. Perreau, A. C. Rodrigues, and M. Simoes. Haemagglutinating properties of *Pasteurella multocida* type A strains isolated from rabbits and poultry. *Ann. Microbiol*. 131 A:255–263. 1980.

Petersen, S. K., and N. T. Foged. Cloning and expression of the *Pasteurella multocida* toxin gene, toxa, in *Escherichia coli*. *Infect. Immun*. 57:3907–3913. 1989.

Petersen, S. K., N. T. Foged, A. Bording, J. P. Nielsen, H. K. Riemann, and P. L. Frandsen. Recombinant derivative of *Pasteurella multocida* toxin: candidates for a vaccine against progressive atrophic rhinitis. *Infect. Immun*. 59:1387–1393. 1991.

Pettit, R. K., R. B. Rimler, and M. R. Ackerrnann. Protection of *Pasteurella multocida* dermonecotic toxin-challenged rats by toxoid-induced antibody. *Vet. Microbiol*. 34:167–173.1993.

Phillips, M., and R. B. Rimler. Protection of chicken by ribosomal vaccines from *Pasteurella multocida*: Dependence upon homologous lipopolysaccharide. *Am. J. Vet. Res*. 45:1785–1789. 1984.

Pijoan, C., and F. Trigo. Bacterial adhesion to mucosal surfaces with special reference to *Pasteurella multocida* isolated from atrophic rhinitis. *Can. J. Vet. Res*. 54 Suppl:SIG-21. 1990.

Pohl, S. DNA relatedness among members of Haemophilus, Pasteurella and Actizobacillus, p. 245–253. In M. Killian, W. Frederiksen, and E. L. Biberstein (eds.), Haemophilus, Pasteurella and Actinobacillus. Academic Press, Inc. (London) Ltd., London. 1981.

Pouedras. P., P. M. Andre, P. Y. Donnio, and J. L. Arril. Cleavage of immunoglobulin A1, A2, and G by Proteases from clinical isolates of *Pasteurella multocida*. *J. Med. Microbiol*. 37 (2):128–132. 1992.

Prantner, M. M., B. G. Harmon, J. R. Glisson, and E. A. Mahaffey. The pathogenesis of *Pasteurella multocida* serotype A:3,4 infection in turkeys: A comparison of two vaccine strains and a field isolate. *Avian Dis*. 34:260–266. 1990.

Rebers, P. A., and K. L. Heddleston. Fowl cholera: Induction of cross-protection in turkeys with bacterins prepared from host-passaged *Pasteurella multocida*. *Avian Dis*. 21:50–56. 1977.

Rebers, P. A., A. E. Jensen, and G. A. Laird. Expression of pill and capsule by the avian strain P-1059 of *Pasteurella multocida*. *Avian Dis*. 32:313–318. 1988.

Rebers, P. A., M. Phillips, R. B. Rimler, R. A. Boykins, and K. R. Rhoades. Immunizing properties of westphal lipopolysaccharide from an avian strain of *Pasteurella multocida*. *Am. J. Vet. Res*. 41:1650–1654. 1980.

Rhoades, K. R., and R. B. Rimler. *Pasteurella multocida* colonization and invasion in experimentally exposed turkey poults. *Avian Dis*. 24:381–383. 1990.

Rhoades, K. R., and R. B. Rimler. Virulence and toxigenicity of capsular serogroup D *Pasteurella multocida* strains isolated from avian hosts. *Avian Dis*. 34:384–388. 1990.

Rhoades, K. R., and R. B. Rimler. Effects of *Pasteurella multocida* endotoxins on turkey poults. *Avian Dis*. 31:523–526. 1987.

Rhoades, K. R., and R. B. Rimler. Fowl Cholera, p. 95–113. In: C. Adlam and J. M. Rutter (eds.), Pasteurella and Pasteurellosis. Academic Press, Inc. San Diego. 1989.

Rhoades, K. R., and R. B. Rimler. Pasteurellosis, p. 145–162. In: S. W. Calnek, H. J. Barnes, C. W. Beard, W. M. Reid, H. W. Yoder, Jr. (eds.), Diseases of Poultry, 9th edition, Iowa State University Press, Ames, Iowa. 1991.

Rietschel, E. T., H. Mayer, H. W. Wollenweber, U. Zahringer, O. Luderitz, O. Westphl, and H. Brade. p. 11–22. In: J. Y. Homma, S. Kanegasaki, O. Luderitz, T. Shiba, and Westphal (eds.), Bacterial Endotoxin: Chemical, Biological and Clinical Aspects, Verag Chemle, Weinheim. YEAR?

Rimler, R. B. Comparison of serologic responses of white leghorn and New Hampshire red chickens to purified lipopolysaccharides of *Pasteurella multocida*. *Avian Dis.* 28:984–989. 1984.

Rimler, R. B. Cross-protection factor(s) of *Pasteurella multocida*: passive immunization of turkeys against fowl cholera caused by different serotypes. *Avian Dis.* 31:884–887. 1987.

Rimler, R. B. Partial purification of cross-protection factor (s) from *Pasteurella multocida*. *Avian Dis.* 38:778–789. 1994.

Rimler, R. B., R. D. Angus, and M. Phillips. Lipopolysaccharides of the Heddleston serotypes of *Pasteurella multocida*. *Am. J. Vet. Res.* 45:759–763. 1984.

Rimler, R. B., and K. A. Brogden. *Pasteurella multocida* isolated from rabbits and swine: Serologic types and toxin production. *Am. J. Vet. Res.* 47:730–737. 1986.

Rimler, R. B., and M. Phillips. Fowl cholera: Protection against *Pasteurella multocida* by ribosomelipopolysaccharide vaccine. *Avian Dis.* 30:409–415. 1986.

Rimler, R. B., P. A. Rebers, and K. B. Rhoades. Fowl cholera: cross-protection induced by *Pasteurella multocida* separated from infected turkey blood. *Avian Dis.* 23:730–741. 1979.

Rimler, R. B., P. A. Rebers, and K. R. Rhoades. Modulation of cross-protection factor(s) of avian *Pasteurella multocida*. *Avian Dis.* 24:989–998. 1980.

Rimler, R. B., K. R. Rhoades. Lysates of turkey-grown *Pasteurella multocida*: protection against homologous and heterologous serotype challenge exposures. *Am. J. Vet. Res.* 42:2117–2121. 1981.

Rimler, R. B., K. R. Rhoades. Cross-protection factor(s) of *Pasteurella multocida*: passive immunization of turkeys against fowl cholera caused by different serotypes. *Avian Dis.* 31:884–887. 1987.

Rimler, R. B., and K. R. Rhoades. Serogroup F, a new capsule serogroup of *Pasteurella multocida*. *J. Clin. Microbiol.* 25:615–618. 1987.

Rimler, R. B., and K. R. Rhoades. Solubilization of membrane-associated cross-protection factor(s) of *Pasteurella multocida*. *Avian Dis.* 33:258–263. 1989.

Rimler, R. B., and K. R. Rhoades. Lysates of turkey-grown *Pasteurella multocida*: protection against homologous and heterologous serotype challenge exposures. *Avian Dis.* 2117–2121. 1981.

Rimler, R. B., and K. R. Rhoades. *Pasteurella multocida*, p. 37–73. In: C. Adlarn and J. M. Rutter (eds.), Pasteurella and Pasteurellosis. Academic Press, Inc. San Diego. 1989.

Rosenbusch, C. T., and I. A. Merchant. A study of the hemorrhagic septicemia Pasteurella. 7. *Bacteriol.* 37:69–89. 1939.

Rosendal, S., P. L. Frandsen, J. P. Nielsen, and R. Gallily. *Pasteurella multocida* toxin induces IL-6, but not IL-1 alpha or TNF alpha in fibroblasts. *Can. J. Vet. Res.* 59:154–156. 1995.

Roy, S., A. B. Das, A. N. Ghosh, and T. Biswas. Purification, Por-forming ability, and antigenic relatedness of the major outer membrane protein of *Shigella dysenteriae* type 1. *Infect. Immun.* 62:4333–4338. 1994.

Rozengurt, E., T. Higgins, N. Chanter, A. J. Lax, and J. M. Staddon. *Pasteurella multocida* toxin: Potent mitogen for cultured fibroblasts. *Proc. Natl. Acad. Sci.* 87:123–127. 1990.

Ruffolo, C. G., and D. Adler. Cloning, sequencing, expression, and protective capacity of the oma87 gene encoding the *Pasteurella multocida* 87-kilodalton outer membrane antigen. *Infect. Immun.* 64:3161–3167. 1996.

Rutter, J. M. and P. D. Luther. Cell culture assay for toxigenic *Pasteurella multocida* from atrophic rhinitis of pigs. *Vet. Rec.* 114:393–396. 1984.

Rutter, J. M., and A. Mackenzie. Pathogenesis of atrophic rhinitis in pigs: A new perspective. *Vet. Rec.* 114:89–90. 1984.

Rutter, J. M. Virulence of *Pasteurella multocida* in atrophic rhinitis of gnotobiotic pigs infected with Bordetella bronchiseptica. *Res. Vet. Sci.* 34:287–295. 1983.

Ryu, E. Studies on *Pasteurella multocida*. I. Inhibition action of blood on the growth of *P. multocida*. *Jpn. J. Vet. Sci.* 21:97–102. 1959.

Salton, M. R. J. Methods of isolation and characterization of bacterial membranes. *Methods Membr. Biol.* 6:101–105. 1976.

Salyers, A. A., and D. D. Whitt. Bacterial Pathogenesis, A Molecular Approach, ch. 3 and ch. 4, p. 30–62. ASM Press, Washington, D.C. 1994.

Sanger, F., S. Nicklen, and A. R. Coulson. DNA sequencing with chain-terminating inhibitors. *Proc. Natl. Acad. Sci. U.S.A.* 74:5463–6467. 1977.

Saukkonen, K., H. Abdillahi, J. T. Poolman and M. Leinonen. Protective efficacy of monoclonal antibodies to class 1 and class 3 outer membrane proteins of Neisseria meningitides B:15:PI. 16 in infant rat infection model: new prospects for vaccine development. *Microb. Pathog.* 3:261–267.1987.

Saukkonen, K., M. Leinonen, H. Abdillahi, and J. T. Poolman. Comparative evaluation of potential components for group B meningococcal vaccine by passive protection in the infant rat and in vitro bactericidal assay. *Vaccine* 7:325–328. 1989.

Sawai, T., K. Matsuba, and S. Yamagishl. A method for measuring the outer membrane-permeability of beta-lactam antibiotics in Gram-negative bacteria. *J. Antibiot.* 90:1134–1136. 1977.

Schindler, H., and J. P. Rosenbusch. Matrix protein from *Escherichia coli*. outer membranes forms voltage-controlled channels in lipid bilayers. *Proc. Natl. Acad. Sci. USA*. 75:3751–3755. 1978.

Schindler, H., and J. P. Rosenbush. Matrix protein in planar membranes: Clusters of channels in a native environment and their functional reassembly. *Proc. Natl. Acad Sci. U.S.A.* 78:2302–2306.1981.

Schlink, G. T., and L. D. Olson. Vaccination of turkeys breeder hens and toms for fowl cholera with cu strain. *Avian Dis.* 31:29–38. 1987.

Schlink, G. T., and L. D. Olson. Vaccination of turkeys breeder hens and toms for fowl cholera with CU strain. *Avian Dis.* 31:29–38. 1987.

Schlink, G. T., and L. D. Olson. Effects of bursectomy, irradiation, and cyclophospharnide on turkeys vaccinated with CU cholera strain. *Avian Dis.* 31:13–21. 1987.

Schlink, G. T., and L. D. Olson. Fowl cholera vaccination of growing turkeys with CU strain via routes other than oral. *Avian Dis.* 31:22–28. 1987.

Schlink, G. T., and L. D. Olson. Relationship between anti-*Pasteurella multocida* antibody titers after CU vaccination and survival after challenge. *Avian Dis.* 33:506–510. 1989.

Smith, L. D. S. Toxin production by *Pasteurella multocida. Proc. Am. Soc. Bacteriol.* p. 93. 1957.

Snipes, K. P., L. M. Hansen, and D. C. Hirsh. Plasma and iron-regulated expression of high molecular weight outer membrane proteins by *Pasteurella multocida. Am. J. Vet. Res.* 49:1336–1338. 1988.

Snipes, K. P., G. Y. Ghazikhanian, and D. C. Hirsh. Fate of *Pasteurella multocida* in the blood vascular system of turkeys following intravenous inoculation: comparison of an encapsulated, virulent strain with its avirulent, a capsular variant. *Avian Dis.* 31:254–259. 1987.

Snipes, K. P., D. C. Hirsh, R. W. Kasten, T. E. Carpenter, D. W. Hird, and R. H. McCapes. Differentiation of field isolates of *Pasteurella multocida* serotype 3,4 from live vaccine strains by genotypic characterization. *Avian Dis.* 34:419–424. 1990.

Solano, W., J. J. Giambrone, and V. S. Panangala. Comparison of enzyme-linked immunosorbent assay and indirect hemagglutination test for quantitating antibody responses in chickens against *Pasteurella multocida. Avian Dis.* 27:1034–1042. 1983.

Sonntag, I., H. Schwarz, Y. Hirota, and U. Henning. Cell envelope and shape of *Escherichia coli*.: Multiple mutants missing the outer membrane lipoprotein and other major outer membrane proteins. *J. Bacteriol.* 136:280–285. 1978.

Staddon, J. M., N. Chanter, A. J. Lax, T. E. Higgins, and E. Rozengurt. *Pasteurella multocida* Toxin, a potent mitogen, stimulates protein kinase C-dependent and -independent protein phosphorylation in Swiss 3T3 cells. *J. Bio. Chem.* 265:11841–11848. 1990.

Straus, D. C., J. D. Cooley, and C. W., Purdy. In vivo production of neuraminidase by *Pasteurella multocida* A:3 in goats after transthoracic challenge. *Curr. Microbial.* 33:266–269. 1996.

Straus, D. C., W. L. Jolly, and C. W. Purdy. Characterization of neuraminidases produced by various serotypes of *Pasteurella multocida. Infect. Immun.* 64:1446–1449. 1996.

Straus, D. C., and C. W. Purdy. Extracellular neuraminidasa production by Paste urella species isolated from infected animals. *Curr. Microbiol.* 31:312–315. 1995.

Struyve, M., J. Visser, H. Adriaanse, R. Benz, and J. Tommassen. Topology of PhoE porin: the 'eyelet' region. *Mol. Microbiol.* 7:131–140. 1992.

Suckow, M. A., T. L. Bowersock, K. Nielsen, C. E. Chrisp, P. L. Frandsen, and E. B. Janovitz. Protective immunity to *Pasteurella multocida* heat-labile toxin by intranasal immunization in rabbits. *Lab. Anim. Sci.* 45:526–532. 1995.

Sutherland, A. D., R. C. Davies, and J. Murray. An experimental anti-idiotype vaccine mimicking lipopolysaccharide gives protection against *Pasteurella multocida* type A infection in mice. *FEMS Immunol. Med. Microbiol.* 7:105–110. 1993.

Szmelcman, S., and M. Hofnung. Matose transport in *Escherichia coli* K-12: Involvement of the bacteriophage Lambda receptor. *J. Bacteriol.* 124:112–118.

Tabaraie, B., B. K. Sharma, P. Renee Sharma, R. Sehgal, and N. K. Ganguly. Evaluation of Salmonella porins as a broad spectrum vaccine candidate. *Microbiol. Immunol.* 38:553–559. 1994.

Tam, J. P., and Y. A. Lu. Vaccine engineering: enhancement of immunogenicity of synthetic peptide vaccines related to hepatitis in chemically defined models consisting of T-cell and B-cell epitopes. *Proc. Natl. Acad. Sci. USA.* 86:9084–9088. 1989.

Tokunaga, H., M. Tokunaga, and T. Nakae. Characterization of porins from the outer membrane of *Salmonella typhimurium. Eur. J. Biochem.* 95:433. 1979.

Truscott, W. M., A. T. Cheung, and D. C. Hirsh. Reduced microbicidal activity of peripheral mononuclear phagocytic cells infected with *Pasteurella multocida. Vet. Microbiol.* 21:283–290. 1990.

Truscott, W. M., and D. C. Hirsh. Demonstration of an outer membrane protein with antiphagocytic activity from *Pasteurella multocida* of avian origin. *Infect. Immun.* 56:1538–1544. 1988.

Tsuji, M., and M. Matsumoto. Immune defense mechanism against blood-born *Pasteurella multocida* in turkeys. *Res. Vet. Sci.* 48:344–349. 1990.

Tsuji, M., and M. Matsumoto. Pathogenesis of fowl cholera: Influence of encapsulation on the fate of *Pasteurella multocida* after intravenous inoculation into turkeys. *Avian Dis.* 33:238–247. 1989.

Tsuji, M., And M. Matsumoto. Evaluation of relationship among three purified antigens from *Pasteurella multocida* strain P-1059 and of their protective capacities in turkeys. *Am. J. Vet. Res.* 49:1516–1521. 1988.

Vachon, V., R. Laprade, and J. W. Coulton. Properties of the porin of *Haemophilus influenzae* type 65b in planar lipid bilayer membranes. *Biophys. Biochim. Acta.* 861:74–82. 1986.

van der Ley, P., J. van der Biezen and J. T. Poolman. Construction of *Neisseria meningitides* strain carrying multiple chromosomal copies of the pox-A gene for use in the production of a multivalent outer membrane vesicle vaccine. *Vaccine* 13:401–407. 1995.

Van der Ley, P., J. R. Heckels, M. Virji, P. Hoogerhout, and J. T. Poolman. Topology of outer membrane porin in pathogenic Neisserisa spp. *Infect. Immun.* 59:2963–2971. 1991.

van der Voort, E. R., P. van der Ley, J. van der Biezen, S. George, O. Tunnela, H. van Dijken, B. Kuipers, and J. Poolman. Specificity of human bactericidal antibodies against PorA PI.7,16 induced with a hexavalent meningococcal outer membrane vesical vaccine. *Infect. Immun.* 64:2745–2751. 1996.

Vasfi-Marandi, M., J. D. Dubreuil, and K. R. Mittal. The 32 kDa major outer-membrane Protein of *Pasteurella multocida* capsular serotype D. Microbiol. 142:199–206. 1996.

Vaught, P. W., H. C. McDougle, and H. H. Burgess. Fowl cholera in waterfowl at Squaw Creek National Wildlife Refuge, Missouri. *J. Wildl. Manage.* 31:248–253. 1967.

Veken, J. W., B. Oudega, J. Luirink, and F. K. deGraaf. Binding of bovine transferrin by *Pasteurella multocida* serotype B:2,5, a strain which cause hemorrhagic septicaemia in buffalo and cattle. *FEMS. Microbiol. Lett.* 115:253–257. 1994.

Vogel, H., and F. Jahnig. Methods for the structure of outer-membrane proteins of *Escherichia coli.* derived from Raman spectroscopy and prediction methods. *J. Mol. Biol.* 190:191–199. 1986.

Von Heijin, G. Signal sequences: The limits of variation. *J. Mol. Biol.* 184:99–105. 1985.

Wang, C. Ph.D. thesis. The University of Georgia, Athens, Ga. 1993.

Wang, C., and J. R. Glisson. Identification of common antigens of serotype 1 and serotype 3 *Pasteurella multocida* in poultry expressed in viva. *Avian Dis.* 38:334–340. 1994.

Wang, C., and J. R. Glisson. Identification of common antigens of serotype I and serotype 3 *Pasteurella multocida* in poultry expressed in vivo. *Avian Dis.* 38:334–340. 1994.

Wang, C., and J. R. Glisson. Passive cross-protection provided by antisera directed against in vivo expressed antigens of *Pasteurella multocida*. *Avian Dis.* 38:506–514. 1994.

Weiss, M. S., and G. E. Schulz. Structure of porin refined at 1.SA resolution. *J. Mol. Biol.* 227:493–509.1992.

Wetzler, L. M., M. S. Blake, K. Barry, and E. C. Gotschlich. Gonococcal porin vaccine evaluation: Comparison of por proteosomes, liposomes, and blebs isolated from rmp deletion mutants. *J. Infect. Dis.* 166:551–555. 1992.

White, D. J., W. L. Jolley, C. W. Purdy, and D. C. Straus. Extracellular neuraminidase production by a *Pasteurella multocida* A:3 strain associated with bovine pneumonia. *Infect. Immun.* 63:1703–1709. 1995.

Wijewardana, T. G., and A. D. Sutherland. Bactericidal activity in the sera of mice vaccinated with *Pasteurella multocida* type A. *Vet. Microbiol.* 24:55–62. 1990.

Wijewardana, T. G., C. F. Wilson, N. J. L. Gilmour, and I. R. Poxton. Production of mouse monoclonal antibodies to *Pasteurella multocida* type A and the immunological properties of a protective anti-lipopolysaccharide antibody. *J. Med. Microbiol.* 33:217–222. 1990.

Zhang, H., A. J. Ainsworth, R. D. Montgomery. Use of a 35.5 kDa cell membrane composition of *Pasteurella multocida* and an anti-idiotype antibody to induce protective immunity in leghorn chickens. *Vet. Immunol. Immunopathol.* 41:89–100. 1994.

Zhao, G., C. Pijoan, K. Choi, S. K. Maheswaran, and E. Trigo. Expression of ion-regulated outer membrane proteins by poycine strains of *Pasteurella multocida*. *Can. J. Vet. Res.* 59:46–50.1995.

Zimmermrann, W., and A. Rosselet. Function of the outer membrane of *Escherichia coli* as a permeability barrier to beta-lactam antibiotics. *Antimicrob. Agents Chemother.* 12:368–372. 1977.

All publications, patents and patent applications are incorporated herein by reference. While in the foregoing specification this invention has been described in relation to certain preferred embodiments thereof, and many details have been set forth for purposes of illustration, it will be apparent to those skilled in the art thatthe invention is susceptible to additional embodiments and that certain of the details described herein may be varied considerably without departing from the basic principles of the invention.

SEQUENCE LISTING

```
<160> NUMBER OF SEQ ID NOS: 61

<210> SEQ ID NO 1
<211> LENGTH: 1604
<212> TYPE: DNA
<213> ORGANISM: Pasteurella multocida

<400> SEQUENCE: 1
aaatataaat aaaatttggg tgaagtgaga aatagaggca tttacccgat gtttttatct      60
ttgatttata ctatttttgt ttttaaatca atgtgttatg ttttaaaaga aaagttctaa     120
aggaaataaa atttttaata aatgtgatct ttttaacact tttttaaccc tgaaaaaacc     180
gctgattttt tgtaacatgt tgtttttaaa ggataaggta aaaaaaaaga caaacctatt     240
ttgttttgac aagaaaacgg agctttgcta tcttgcattt gcaaaaatgt gcagacgact     300
tatcgtctgt tagtcgattt taggttgatt gagtgattgg caacaatcat ttaatcgaat     360
tataaaactc caaaaacaag gtagtgatac tatgaaaaag acaatcgtag cattagcagt     420
cgcagcagta gcagcaactt cagcaaacgc agcaacagtt tacaatcaag acggtaccaa     480
agttgatgta aacggttctt tacgtttaat ccttaaaaaa gaaaaaaatg agcgcggtga     540
tttagtggat aacggttcac gcgtttcatt caaagcatct catgatttag gcgaaggctt     600
aagcgcatta gcttatacag aacttcgttt tagtaaaaat gtacccgtgc aagtaaaaga     660
ccaacaaggt gaagtagtac gtgagtatga ggttgagaaa cttggtaaca atgttcacgt     720
aaaacgtctt tatgcgggtt tcgcgtatga aggtttaggt acattaacat tcggtaacca     780
attaactatc ggtgatgatg ttggtctatc tgactatacc tatttcaaca gtggtattaa     840
taacctcctt tctagcggtg aaaaagcaat taactttaaa tctgcagaat tcaatggttt     900
cacatttggt ggtgcgtatg tcttctctgc tgatgctgac aaacaagcat tacgtgatgg     960
tcgcggtttc gttgtagcag gtttatacaa cagaaaaatg ggtgatgttg gttttgcatt    1020
cgaagccggt tatagccaaa aatatgtgaa acaagaagtt gaacagaatc cgccagcagc    1080
```

-continued

```
acaaaaagtg tttaaagatg aaaaagagaa agctttcatg gtgggtgctg agttatcata   1140
tgctggttta gcgcttggtg ttgactacgc acaatctaaa gtgactaacg tagatggtaa   1200
aaaacgtgct cttgaagtgg gtttaaatta tgaccttaac gacagagcga aagtttacac   1260
agacttcatc tgggaaaaag aaggtcctaa aggtgatgtt acaagaaacc gtactgtcgc   1320
tgtaggtttt ggttacaaac ttcacaaaca agtggaaact tttgttgaag cagcttgggg   1380
tagagagaaa gactctgatg gtgtaacaac aaaaaacaac gtagtaggta caggtttacg   1440
cgtacacttc taatttttgt tagaatctga aaaaagccag tgttaaacac tggcttttta   1500
ttgggtttta tttgttttac ttacaataaa ttaggatttt gaaagtcgtt acgcggtcat   1560
ctttctcaaa ataatacata tcaatatgtt gcaaggaatg gatc                    1604
```

<210> SEQ ID NO 2
<211> LENGTH: 353
<212> TYPE: PRT
<213> ORGANISM: Pasteurella multocida

<400> SEQUENCE: 2

```
Met Lys Lys Thr Ile Val Ala Leu Ala Val Ala Ala Val Ala Ala Thr
 1               5                  10                  15

Ser Ala Asn Ala Ala Thr Val Tyr Asn Gln Asp Gly Thr Lys Val Asp
            20                  25                  30

Val Asn Gly Ser Leu Arg Leu Ile Leu Lys Lys Glu Lys Asn Glu Arg
        35                  40                  45

Gly Asp Leu Val Asp Asn Gly Ser Arg Val Ser Phe Lys Ala Ser His
    50                  55                  60

Asp Leu Gly Glu Gly Leu Ser Ala Leu Ala Tyr Thr Glu Leu Arg Phe
65                  70                  75                  80

Ser Lys Asn Val Pro Val Gln Val Lys Asp Gln Gln Gly Glu Val Val
                85                  90                  95

Arg Glu Tyr Glu Val Glu Lys Leu Gly Asn Asn Val His Val Lys Arg
            100                 105                 110

Leu Tyr Ala Gly Phe Ala Tyr Glu Gly Leu Gly Thr Leu Thr Phe Gly
        115                 120                 125

Asn Gln Leu Thr Ile Gly Asp Asp Val Gly Leu Ser Asp Tyr Thr Tyr
    130                 135                 140

Phe Asn Ser Gly Ile Asn Asn Leu Leu Ser Ser Gly Glu Lys Ala Ile
145                 150                 155                 160

Asn Phe Lys Ser Ala Glu Phe Asn Gly Phe Thr Phe Gly Gly Ala Tyr
                165                 170                 175

Val Phe Ser Ala Asp Ala Asp Lys Gln Ala Leu Arg Asp Gly Arg Gly
            180                 185                 190

Phe Val Val Ala Gly Leu Tyr Asn Arg Lys Met Gly Asp Val Gly Phe
        195                 200                 205

Ala Phe Glu Ala Gly Tyr Ser Gln Lys Tyr Val Lys Gln Glu Val Glu
    210                 215                 220

Gln Asn Pro Pro Ala Ala Gln Lys Val Phe Lys Asp Glu Lys Glu Lys
225                 230                 235                 240

Ala Phe Met Val Gly Ala Glu Leu Ser Tyr Ala Gly Leu Ala Leu Gly
                245                 250                 255

Val Asp Tyr Ala Gln Ser Lys Val Thr Asn Val Asp Gly Lys Lys Arg
            260                 265                 270

Ala Leu Glu Val Gly Leu Asn Tyr Asp Leu Asn Asp Arg Ala Lys Val
        275                 280                 285
```

```
Tyr Thr Asp Phe Ile Trp Glu Lys Glu Gly Pro Lys Gly Asp Val Thr
            290                 295                 300

Arg Asn Arg Thr Val Ala Val Gly Phe Gly Tyr Lys Leu His Lys Gln
305                 310                 315                 320

Val Glu Thr Phe Val Glu Ala Ala Trp Gly Arg Glu Lys Asp Ser Asp
                325                 330                 335

Gly Val Thr Thr Lys Asn Asn Val Val Gly Thr Gly Leu Arg Val His
            340                 345                 350

Phe
```

<210> SEQ ID NO 3
<211> LENGTH: 1032
<212> TYPE: DNA
<213> ORGANISM: Pasteurella multocida

<400> SEQUENCE: 3

```
atgaaaaaga caatcgtagc attagcagtc gcagcagtag cagcaacttc agcaaacgcc      60
gcaacagttt acaatcaaga cggtacaaaa gttgatgtaa acggttctgt acgtttaatc     120
cttaaaaaag aaaaaaatga gcgcggtgat ttagtggata acggttcacg cgtttctttc     180
aaagcatctc atgacttagg cgaaggttta agcgcattag cttacgcgga acttcgtttc     240
agtaaaaatg agaaagtaga agtgaaagat gcacaaaatc aacaagtagt tcgtaaatat     300
gaagttgagc gtatcggtaa cgatgttcat gtaaaacgtc tttatgcggg tttcgcgtat     360
gaaggtttag gaacattaac tttcggtaac caattaacta tcggtgatga tgttggtgtg     420
tctgactaca cttacttctt aggtggtatc aacaaccttc tttctagcgg tgaaaaagca     480
attaacttta aatctgcaga attcaacggt ttcacatttg gtggtgcgta tgtgttctca     540
gcggatgctg acaaacaagc accacgtgat ggtcgcggtt tcgttgtagc aggttttatac     600
aacagaaaaa tgggcgatgt tggtttcgca cttgaagcag gttatagcca aaaatatgta     660
acagcagcag ctaaacaaga aaagaaaaa gcctttatgg ttggtactga attatcatat     720
gctggtttag cacttggtgt tgactacgca caatctaaag tgactaacgt agaaggtaaa     780
aaacgcgcac ttgaagtagg tttaaactat gacattaatg acaaagcaaa agtttacact     840
gacttgattt gggcaaaaga aggtccaaaa ggtgcgacta caagagatcg ttctatcatc     900
ttaggtgcgg gctacaagct tcacaaacaa gttgaaacct tgttgaagg tggctggggc     960
agagagaaag atgctaatgg cgtaacaaca aagataaca aagttggtgt tggtttacgc    1020
gtacacttct aa                                                       1032
```

<210> SEQ ID NO 4
<211> LENGTH: 343
<212> TYPE: PRT
<213> ORGANISM: Pasteurella multocida

<400> SEQUENCE: 4

```
Met Lys Lys Thr Ile Val Ala Leu Ala Val Ala Ala Val Ala Ala Thr
 1                5                  10                  15

Ser Ala Asn Ala Ala Thr Val Tyr Asn Gln Asp Gly Thr Lys Val Asp
            20                  25                  30

Val Asn Gly Ser Val Arg Leu Ile Leu Lys Lys Glu Lys Asn Glu Arg
         35                  40                  45

Gly Asp Leu Val Asp Asn Gly Ser Arg Val Ser Phe Lys Ala Ser His
     50                  55                  60
```

-continued

```
Asp Leu Gly Glu Gly Leu Ser Ala Leu Ala Tyr Ala Glu Leu Arg Phe
65                  70                  75                  80

Ser Lys Asn Glu Lys Val Glu Val Lys Asp Ala Gln Asn Gln Gln Val
                85                  90                  95

Val Arg Lys Tyr Glu Val Glu Arg Ile Gly Asn Asp Val His Val Lys
            100                 105                 110

Arg Leu Tyr Ala Gly Phe Ala Tyr Glu Gly Leu Gly Thr Leu Thr Phe
        115                 120                 125

Gly Asn Gln Leu Thr Ile Gly Asp Asp Val Gly Val Ser Asp Tyr Thr
    130                 135                 140

Tyr Phe Leu Gly Gly Ile Asn Asn Leu Leu Ser Ser Gly Glu Lys Ala
145                 150                 155                 160

Ile Asn Phe Lys Ser Ala Glu Phe Asn Gly Phe Thr Phe Gly Gly Ala
                165                 170                 175

Tyr Val Phe Ser Ala Asp Ala Asp Lys Gln Ala Pro Arg Asp Gly Arg
            180                 185                 190

Gly Phe Val Val Ala Gly Leu Tyr Asn Arg Lys Met Gly Asp Val Gly
        195                 200                 205

Phe Ala Leu Glu Ala Gly Tyr Ser Gln Lys Tyr Val Thr Ala Ala Ala
    210                 215                 220

Lys Gln Glu Lys Glu Lys Ala Phe Met Val Gly Thr Glu Leu Ser Tyr
225                 230                 235                 240

Ala Gly Leu Ala Leu Gly Val Asp Tyr Ala Gln Ser Lys Val Thr Asn
                245                 250                 255

Val Glu Gly Lys Lys Arg Ala Leu Glu Val Gly Leu Asn Tyr Asp Ile
            260                 265                 270

Asn Asp Lys Ala Lys Val Tyr Thr Asp Leu Ile Trp Ala Lys Glu Gly
        275                 280                 285

Pro Lys Gly Ala Thr Thr Arg Asp Arg Ser Ile Ile Leu Gly Ala Gly
    290                 295                 300

Tyr Lys Leu His Lys Gln Val Glu Thr Phe Val Glu Gly Gly Trp Gly
305                 310                 315                 320

Arg Glu Lys Asp Ala Asn Gly Val Thr Thr Lys Asp Asn Lys Val Gly
                325                 330                 335

Val Gly Leu Arg Val His Phe
            340
```

<210> SEQ ID NO 5
<211> LENGTH: 20
<212> TYPE: DNA
<213> ORGANISM: Pasteurella multocida
<220> FEATURE:
<221> NAME/KEY: misc_feature
<222> LOCATION: (1)...(20)
<223> OTHER INFORMATION: n = A,T,C or G

<400> SEQUENCE: 5
acngtntaya aycargaygg 20

<210> SEQ ID NO 6
<211> LENGTH: 20
<212> TYPE: DNA
<213> ORGANISM: Pasteurella multocida
<220> FEATURE:
<221> NAME/KEY: modified_base
<222> LOCATION: (3)...(3)
<223> OTHER INFORMATION: n = Inosine
<220> FEATURE:
<221> NAME/KEY: modified_base

```
<222> LOCATION: (18)...(18)
<223> OTHER INFORMATION: n= Inosine

<400> SEQUENCE: 6
gtntayaayc argayggnac                                                  20

<210> SEQ ID NO 7
<211> LENGTH: 24
<212> TYPE: DNA
<213> ORGANISM: Artificial Sequence
<220> FEATURE:
<223> OTHER INFORMATION: A primer derived from pUC18

<400> SEQUENCE: 7
agcggataac aatttcacac agga                                             24

<210> SEQ ID NO 8
<211> LENGTH: 20
<212> TYPE: DNA
<213> ORGANISM: Pasteurella multocida
<220> FEATURE:
<221> NAME/KEY: modified_base
<222> LOCATION: (12)...(12)
<223> OTHER INFORMATION: n = Inosine
<220> FEATURE:
<221> NAME/KEY: modified_base
<222> LOCATION: (15)...(15)
<223> OTHER INFORMATION: n = Inosine

<400> SEQUENCE: 8
aaycargayg gnacnaargt                                                  20

<210> SEQ ID NO 9
<211> LENGTH: 357
<212> TYPE: PRT
<213> ORGANISM: Haemophilus influenzae

<400> SEQUENCE: 9
```

| Met | Lys | Lys | Thr | Leu | Ala | Ala | Leu | Ile | Val | Val | Ala | Phe | Ala | Ala | Ser |
|---|---|---|---|---|---|---|---|---|---|---|---|---|---|---|---|
| 1 | | | | 5 | | | | | 10 | | | | | 15 | |

| Ala | Ala | Asn | Ala | Ala | Val | Val | Tyr | Asn | Asn | Glu | Gly | Thr | Lys | Val | Glu |
|---|---|---|---|---|---|---|---|---|---|---|---|---|---|---|---|
| | | | 20 | | | | | 25 | | | | | 30 | | |

| Leu | Gly | Gly | Arg | Leu | Thr | Ile | Ile | Ala | Glu | Gln | Ser | Ser | Asn | Thr | Leu |
|---|---|---|---|---|---|---|---|---|---|---|---|---|---|---|---|
| | | 35 | | | | | 40 | | | | | 45 | | | |

| Asp | Asp | Gln | Lys | Gln | Gln | His | Gly | Ala | Leu | Arg | Asn | Gln | Gly | Ser | Arg |
|---|---|---|---|---|---|---|---|---|---|---|---|---|---|---|---|
| | 50 | | | | | 55 | | | | | 60 | | | | |

| Phe | His | Ile | Lys | Ala | Thr | His | Asn | Phe | Gly | Asp | Gly | Phe | Tyr | Ala | Gln |
|---|---|---|---|---|---|---|---|---|---|---|---|---|---|---|---|
| 65 | | | | | 70 | | | | | 75 | | | | | 80 |

| Gly | Tyr | Leu | Glu | Thr | Arg | Phe | Val | Ser | Lys | Tyr | Lys | Asp | Asn | Ala | Asp |
|---|---|---|---|---|---|---|---|---|---|---|---|---|---|---|---|
| | | | | 85 | | | | | 90 | | | | | 95 | |

| His | Phe | Asp | Ser | Ile | Thr | Thr | Lys | Tyr | Ala | Tyr | Val | Thr | Leu | Gly | Asn |
|---|---|---|---|---|---|---|---|---|---|---|---|---|---|---|---|
| | | | 100 | | | | | 105 | | | | | 110 | | |

| Lys | Ala | Leu | Gly | Glu | Val | Lys | Leu | Gly | Arg | Ala | Lys | Thr | Ile | Ala | Asp |
|---|---|---|---|---|---|---|---|---|---|---|---|---|---|---|---|
| | | 115 | | | | | 120 | | | | | 125 | | | |

| Gly | Ile | Thr | Ser | Ala | Glu | Asp | Lys | Glu | Tyr | Gly | Val | Leu | Asn | Asn | Ser |
|---|---|---|---|---|---|---|---|---|---|---|---|---|---|---|---|
| | 130 | | | | | 135 | | | | | 140 | | | | |

| Lys | Tyr | Ile | Pro | Thr | Asn | Gly | Asn | Thr | Val | Gly | Tyr | Thr | Phe | Glu | Gly |
|---|---|---|---|---|---|---|---|---|---|---|---|---|---|---|---|
| 145 | | | | | 150 | | | | | 155 | | | | | 160 |

| Ile | Asp | Gly | Leu | Val | Leu | Gly | Ala | Asn | Tyr | Leu | Leu | Ala | Gln | Gln | Arg |
|---|---|---|---|---|---|---|---|---|---|---|---|---|---|---|---|
| | | | | 165 | | | | | 170 | | | | | 175 | |

| Asn | Ala | His | Gly | Ser | Thr | Ala | Gly | Glu | Val | Val | Ala | Gln | Val | Ile | Ser |
|---|---|---|---|---|---|---|---|---|---|---|---|---|---|---|---|

-continued

```
                180                 185                 190
Asn Gly Val Gln Val Gly Ala Lys Tyr Asp Ala Asn Ile Ile Ala
            195                 200                 205
Gly Ile Ala Tyr Gly Arg Thr Asn Tyr Arg Glu Asp Leu Ala Ala Gln
    210                 215                 220
Gly Asp Ser Asp Lys Lys Gln Gln Val Asn Gly Ala Leu Ser Thr Leu
225                 230                 235                 240
Gly Tyr Arg Phe Ser Asp Leu Gly Leu Leu Val Ser Leu Asp Ser Gly
                245                 250                 255
Tyr Ala Lys Thr Lys Asn Tyr Lys Asp Lys His Glu Lys Arg Tyr Phe
            260                 265                 270
Val Ser Pro Gly Phe Gln Tyr Glu Leu Met Glu Asp Thr Asn Val Tyr
        275                 280                 285
Gly Asn Phe Lys Tyr Glu Arg Asn Ser Val Asp Gln Gly Lys Lys Ala
    290                 295                 300
Arg Glu His Ala Val Leu Phe Gly Val Asp His Lys Leu His Lys Gln
305                 310                 315                 320
Val Leu Thr Tyr Ile Glu Gly Ala Tyr Ala Arg Thr Arg Thr Asn Asp
                325                 330                 335
Lys Gly Lys Thr Glu Lys Thr Glu Lys Glu Lys Ser Val Gly Val Gly
            340                 345                 350
Leu Arg Val Tyr Phe
        355

<210> SEQ ID NO 10
<211> LENGTH: 18
<212> TYPE: DNA
<213> ORGANISM: Artificial Sequence
<220> FEATURE:
<223> OTHER INFORMATION: A primer derived from pUC18

<400> SEQUENCE: 10
tgtaaaacga cggccagt                                                 18

<210> SEQ ID NO 11
<211> LENGTH: 20
<212> TYPE: PRT
<213> ORGANISM: Pasteurella multocida
<220> FEATURE:
<221> NAME/KEY: VARIANT
<222> LOCATION: (1)...(20)
<223> OTHER INFORMATION: Xaa = Any Amino Acid

<400> SEQUENCE: 11

Ala Thr Val Tyr Asn Gln Asp Gly Thr Lys Val Asp Val Asn Gly Ser
  1               5                  10                  15
Leu Arg Xaa Ile
            20

<210> SEQ ID NO 12
<211> LENGTH: 21
<212> TYPE: DNA
<213> ORGANISM: Pasteurella multocida

<400> SEQUENCE: 12
gcttaagcct tcgcctaaat c                                             21

<210> SEQ ID NO 13
<211> LENGTH: 22
<212> TYPE: DNA
```

-continued

<213> ORGANISM: Pasteurella multocida

<400> SEQUENCE: 13
tttggtggtg cgtatgtctt ct 22

<210> SEQ ID NO 14
<211> LENGTH: 25
<212> TYPE: DNA
<213> ORGANISM: Pasteurella multocida

<400> SEQUENCE: 14
tcaactatga aaaagacaat cgtag 25

<210> SEQ ID NO 15
<211> LENGTH: 25
<212> TYPE: DNA
<213> ORGANISM: Pasteurella multocida

<400> SEQUENCE: 15
tcacagcaac agtttacaat caaga 25

<210> SEQ ID NO 16
<211> LENGTH: 25
<212> TYPE: DNA
<213> ORGANISM: Pasteurella multocida

<400> SEQUENCE: 16
ctagatccat tccttgcaac atatt 25

<210> SEQ ID NO 17
<211> LENGTH: 20
<212> TYPE: PRT
<213> ORGANISM: Pasteurella multocida

<400> SEQUENCE: 17

```
Ala Thr Val Tyr Asn Gln Asp Gly Thr Lys Val Asp Val Asn Gly Ser
 1               5                  10                  15

Val Arg Leu Ile
            20
```

<210> SEQ ID NO 18
<211> LENGTH:
<212> TYPE:
<213> ORGANISM:

<400> SEQUENCE: 18

000

<210> SEQ ID NO 19
<211> LENGTH:
<212> TYPE:
<213> ORGANISM:

<400> SEQUENCE: 19

000

<210> SEQ ID NO 20
<211> LENGTH:
<212> TYPE:
<213> ORGANISM:

<400> SEQUENCE: 20

000

```
<210> SEQ ID NO 21
<211> LENGTH:
<212> TYPE:
<213> ORGANISM:

<400> SEQUENCE: 21

000

<210> SEQ ID NO 22
<211> LENGTH:
<212> TYPE:
<213> ORGANISM:

<400> SEQUENCE: 22

000

<210> SEQ ID NO 23
<211> LENGTH:
<212> TYPE:
<213> ORGANISM:

<400> SEQUENCE: 23

000

<210> SEQ ID NO 24
<211> LENGTH:
<212> TYPE:
<213> ORGANISM:

<400> SEQUENCE: 24

000

<210> SEQ ID NO 25
<211> LENGTH:
<212> TYPE:
<213> ORGANISM:

<400> SEQUENCE: 25

000

<210> SEQ ID NO 26
<211> LENGTH:
<212> TYPE:
<213> ORGANISM:

<400> SEQUENCE: 26

000

<210> SEQ ID NO 27
<211> LENGTH:
<212> TYPE:
<213> ORGANISM:

<400> SEQUENCE: 27

000

<210> SEQ ID NO 28
<211> LENGTH:
<212> TYPE:
<213> ORGANISM:

<400> SEQUENCE: 28
```

-continued

```
000

<210> SEQ ID NO 29
<211> LENGTH:
<212> TYPE:
<213> ORGANISM:

<400> SEQUENCE: 29

000

<210> SEQ ID NO 30
<211> LENGTH:
<212> TYPE:
<213> ORGANISM:

<400> SEQUENCE: 30

000

<210> SEQ ID NO 31
<211> LENGTH: 323
<212> TYPE: PRT
<213> ORGANISM: Pasteurella multocida

<400> SEQUENCE: 31

Ala Thr Val Tyr Asn Gln Asp Gly Thr Lys Val Asp Val Asn Gly Ser
 1               5                  10                  15

Val Arg Leu Ile Leu Lys Lys Glu Lys Asn Glu Arg Gly Asp Leu Val
            20                  25                  30

Asp Asn Gly Ser Arg Val Ser Phe Lys Ala Ser His Asp Leu Gly Glu
        35                  40                  45

Gly Leu Ser Ala Leu Ala Tyr Ala Glu Leu Arg Phe Ser Thr Lys Glu
    50                  55                  60

Lys Val Glu Val Lys Asp Thr Gln Asn Pro Pro Lys Val Val Arg Thr
65                  70                  75                  80

Tyr Glu Val Glu Lys Ile Gly Asn Asp Val His Val Lys Arg Leu Tyr
                85                  90                  95

Ala Gly Phe Ala Tyr Glu Gly Leu Gly Thr Leu Thr Phe Gly Asn Gln
            100                 105                 110

Leu Thr Ile Gly Asp Asp Val Gly Val Ser Asp Tyr Thr Tyr Phe Leu
        115                 120                 125

Gly Gly Ile Asn Asn Leu Leu Ser Ser Gly Glu Lys Ala Ile Asn Phe
    130                 135                 140

Lys Ser Ala Glu Phe Asn Gly Phe Thr Phe Gly Gly Ala Tyr Val Phe
145                 150                 155                 160

Ser Ala Asp Ala Asp Lys Gln Ala Pro Arg Asp Gly Arg Gly Phe Val
                165                 170                 175

Val Ala Gly Leu Tyr Asn Arg Lys Met Gly Asp Val Gly Phe Ala Leu
            180                 185                 190

Glu Ala Gly Tyr Ser Gln Lys Tyr Val Thr Val Ala Lys Gln Glu Lys
        195                 200                 205

Glu Lys Ala Phe Met Val Gly Thr Glu Leu Ser Tyr Ala Gly Leu Ala
    210                 215                 220

Leu Gly Val Asp Tyr Ala Gln Ser Lys Val Thr Asn Val Asp Gly Lys
225                 230                 235                 240

Lys Arg Ala Leu Glu Val Gly Leu Asn Tyr Asp Ile Asn Asp Lys Ala
                245                 250                 255

Lys Val Tyr Thr Asp Leu Ile Trp Ala Lys Lys Gly Pro Lys Gly Ala
```

```
                    260                 265                 270
Thr Thr Arg Asp Arg Ser Ile Ile Leu Gly Ala Gly Tyr Lys Leu His
        275                 280                 285
Lys Gln Val Glu Thr Phe Val Glu Gly Gly Trp Gly Arg Glu Lys Asp
    290                 295                 300
Ala Asn Gly Val Thr Thr Lys Asp Asn Val Val Gly Val Gly Leu Arg
305                 310                 315                 320
Val His Phe

<210> SEQ ID NO 32
<211> LENGTH: 321
<212> TYPE: PRT
<213> ORGANISM: Pasteurella multocida

<400> SEQUENCE: 32

Ala Thr Val Tyr Asn Gln Asp Gly Thr Lys Val Asp Val Asn Gly Ser
1               5                   10                  15
Val Arg Leu Ile Leu Lys Lys Glu Lys Asp Lys Arg Gly Asp Leu Val
            20                  25                  30
Asp Asn Gly Ser Arg Val Ser Phe Lys Ala Ser His Asp Leu Gly Glu
        35                  40                  45
Gly Leu Ser Ala Leu Ala Tyr Ala Glu Leu Arg Phe Ser Thr Lys Glu
    50                  55                  60
Glu Val Glu Val Thr Gln Asn Gln Gln Val Val Arg Lys Tyr Lys Val
65                  70                  75                  80
Glu Arg Ile Gly Asn Asp Val His Val Lys Arg Leu Tyr Ala Gly Phe
                85                  90                  95
Ala Tyr Glu Gly Leu Gly Thr Leu Thr Phe Gly Asn Gln Leu Thr Ile
            100                 105                 110
Gly Asp Asp Val Gly Val Ser Asp Tyr Thr Tyr Phe Leu Gly Gly Ile
        115                 120                 125
Asn Asn Leu Leu Ser Ser Gly Glu Lys Ala Ile Asn Phe Lys Ser Ala
    130                 135                 140
Glu Phe Asn Gly Phe Thr Phe Gly Gly Ala Tyr Val Phe Ser Ala Asp
145                 150                 155                 160
Ala Asp Lys Gln Ala Ala Arg Asp Gly Arg Gly Phe Val Val Ala Gly
                165                 170                 175
Leu Tyr Asn Arg Lys Met Gly Asp Val Gly Phe Ala Leu Glu Ala Gly
            180                 185                 190
Tyr Ser Gln Lys Tyr Val Thr Glu Thr Ala Lys Gln Glu Lys Glu Lys
        195                 200                 205
Ala Phe Met Val Gly Thr Glu Leu Ser Tyr Ala Gly Leu Ala Leu Gly
    210                 215                 220
Val Asp Tyr Ala Gln Ser Lys Val Thr Asn Val Asp Gly Lys Lys Arg
225                 230                 235                 240
Ala Leu Glu Val Gly Leu Asn Tyr Asp Leu Asn Asp Lys Ala Lys Val
                245                 250                 255
Tyr Thr Asp Leu Ile Trp Ala Lys Lys Gly Pro Lys Gly Ala Thr Thr
            260                 265                 270
Arg Asp Arg Ala Ile Ile Leu Gly Ala Gly Tyr Lys Leu His Lys Gln
        275                 280                 285
Val Glu Thr Phe Val Glu Gly Gly Trp Gly Arg Thr Lys Asn Ala Ala
    290                 295                 300
Gly Val Thr Thr Lys Asp Asn Lys Val Gly Val Gly Leu Arg Val His
```

Phe

<210> SEQ ID NO 33
<211> LENGTH: 323
<212> TYPE: PRT
<213> ORGANISM: Pasteurella multocida

<400> SEQUENCE: 33

```
Ala Thr Val Tyr Asn Gln Asp Gly Thr Lys Val Asp Val Asn Gly Ser
 1               5                  10                  15
Val Arg Leu Leu Leu Lys Lys Glu Asn Asp Lys Arg Gly Asp Leu Ile
            20                  25                  30
Asp Asn Gly Ser Arg Val Ser Phe Lys Ala Ser His Asp Leu Gly Glu
        35                  40                  45
Gly Leu Ser Ala Leu Gly Tyr Ala Glu Leu Arg Phe Ser Asp Asp Val
    50                  55                  60
Lys Asp Gln Asp Gly Asn Val Lys Gln Pro Ile Gly Asn Lys Val
65                  70                  75                  80
His Ala Lys Arg Leu Tyr Ala Gly Phe Ala Tyr Glu Gly Leu Gly Thr
                85                  90                  95
Leu Thr Phe Gly Asn Gln Leu Thr Ile Gly Asp Asp Val Gly Val Ser
            100                 105                 110
Asp Tyr Thr Tyr Phe Asn Ser Gly Ile Asn Gly Val Leu Ile Thr Ser
        115                 120                 125
Gly Gln Lys Ala Ile Asn Phe Lys Ser Ala Glu Phe Asn Gly Phe Thr
    130                 135                 140
Phe Gly Gly Ala Tyr Val Phe Ser Gly Asp Ala Asn Lys Asp Ala Leu
145                 150                 155                 160
Arg Asp Gly Arg Gly Phe Val Val Ala Gly Leu Tyr Asn Arg Gln Ile
                165                 170                 175
Gly Asp Val Gly Phe Ala Phe Glu Ala Gly Tyr Ser Gln Lys Tyr Val
            180                 185                 190
Lys Gln Val Asp Asp Ser Val Val Pro Asn Lys Glu Trp Asp Glu Lys
        195                 200                 205
Glu Lys Ala Phe Leu Val Gly Thr Glu Leu Ser Tyr Ala Gly Leu Ala
    210                 215                 220
Leu Gly Val Asp Tyr Ala Gln Ser Lys Val Thr Asn Val Glu Gly Lys
225                 230                 235                 240
Lys Arg Ala Leu Glu Val Gly Leu Lys Tyr Glu Leu Asn Asp Lys Ala
                245                 250                 255
Lys Val Tyr Thr Asp Phe Ile Trp Ala Lys Glu Gly Pro Lys Gly Asp
            260                 265                 270
Thr Asp Arg Thr Arg Lys Ile Ala Val Gly Phe Gly Tyr Lys Leu His
        275                 280                 285
Lys Gln Val Glu Thr Phe Val Glu Gly Ala Trp Gly Arg Thr Lys Asp
    290                 295                 300
Ala Asp Gly Thr Thr Thr Lys Asn Asn Val Ile Gly Thr Gly Leu Arg
305                 310                 315                 320
Val His Phe
```

<210> SEQ ID NO 34
<211> LENGTH: 323
<212> TYPE: PRT
<213> ORGANISM: Pasteurella multocida

<400> SEQUENCE: 34

Ala Thr Val Tyr Asn Gln Asp Gly Thr Lys Val Asp Val Asn Gly Ser
1               5                   10                  15

Val Arg Leu Leu Leu Lys Lys Glu Lys Asp Lys Arg Gly Asp Leu Ile
                20                  25                  30

Asp Asn Gly Ser Arg Val Ser Phe Lys Ala Ser His Asp Leu Gly Glu
            35                  40                  45

Gly Leu Ser Ala Leu Gly Tyr Ala Glu Leu Arg Phe Ser Asp Asp Val
        50                  55                  60

Lys Asp Gln Asp Gly Asn Val Val Lys Gln Pro Ile Gly Asn Lys Val
65                  70                  75                  80

His Ala Lys Arg Leu Tyr Ala Gly Phe Ala Tyr Glu Gly Leu Gly Thr
                85                  90                  95

Leu Thr Phe Gly Asn Gln Leu Thr Ile Gly Asp Asp Val Gly Val Ser
            100                 105                 110

Asp Tyr Thr Tyr Phe Asn Ser Gly Ile Asn Gly Val Leu Ile Thr Ser
        115                 120                 125

Gly Gln Lys Ala Ile Asn Phe Lys Ser Ala Glu Phe Asn Gly Phe Thr
    130                 135                 140

Phe Gly Gly Ala Tyr Val Phe Ser Gly Asp Ala Asn Lys Asp Ala Leu
145                 150                 155                 160

Arg Asp Gly Arg Gly Phe Val Ala Gly Leu Tyr Asn Arg Gln Ile
                165                 170                 175

Gly Asp Val Gly Phe Ala Phe Glu Ala Gly Tyr Ser Gln Lys Tyr Val
            180                 185                 190

Lys Gln Val Asp Asp Ser Val Val Pro Asn Lys Glu Trp Asp Glu Lys
        195                 200                 205

Glu Lys Ala Phe Leu Val Gly Thr Glu Leu Ser Tyr Ala Gly Leu Ala
    210                 215                 220

Leu Gly Val Asp Tyr Ala Gln Ser Lys Val Thr Asn Val Glu Gly Lys
225                 230                 235                 240

Lys Arg Ala Leu Glu Val Gly Leu Lys Tyr Glu Leu Asn Asp Lys Ala
                245                 250                 255

Lys Val Tyr Thr Asp Phe Ile Trp Ala Lys Glu Gly Pro Lys Gly Asp
            260                 265                 270

Thr Asp Arg Thr Arg Lys Ile Ala Val Gly Phe Gly Tyr Lys Leu His
        275                 280                 285

Lys Gln Val Glu Thr Phe Val Glu Gly Ala Trp Gly Arg Thr Lys Asp
    290                 295                 300

Ala Asp Gly Thr Thr Thr Lys Asn Asn Val Ile Gly Thr Gly Leu Arg
305                 310                 315                 320

Val His Phe

<210> SEQ ID NO 35
<211> LENGTH: 329
<212> TYPE: PRT
<213> ORGANISM: Pasteurella multocida

<400> SEQUENCE: 35

Ala Thr Val Tyr Asn Gln Asp Gly Thr Thr Val Asp Val Asn Gly Ser
1               5                   10                  15

Val Arg Leu Leu Leu Lys Lys Glu Lys Asp Met Arg Gly Asp Leu Ile
                20                  25                  30

-continued

```
Asp Asn Gly Ser Arg Val Ser Phe Lys Ala Ser His Asp Leu Gly Glu
        35                  40                  45

Gly Leu Ser Ala Leu Gly Tyr Ala Glu Leu Arg Phe Ser Asp Asp Val
    50                  55                  60

Lys Asp Lys Asp Gly Asn Val Val Asn Gln Pro Ile Gly Asn Lys Val
65                  70                  75                  80

His Ala Lys Arg Leu Tyr Ala Gly Phe Ala Tyr Glu Gly Leu Gly Thr
                85                  90                  95

Leu Thr Phe Gly Asn Gln Leu Thr Ile Gly Asp Asp Val Gly Val Ser
            100                 105                 110

Asp Tyr Thr Tyr Phe Asn Ser Gly Ile Asn Gly Val Leu Ile Thr Ser
        115                 120                 125

Gly Gln Lys Ala Ile Asn Phe Lys Ser Ala Glu Phe Asn Gly Phe Thr
    130                 135                 140

Phe Gly Gly Ala Tyr Val Phe Ser Gly Asp Ala Asn Lys Asp Ala Leu
145                 150                 155                 160

Arg Asp Gly Arg Gly Phe Val Val Ala Gly Leu Tyr Asn Arg Gln Ile
                165                 170                 175

Gly Asp Val Gly Phe Ala Phe Glu Ala Ala Tyr Ser Gln Lys Tyr Val
            180                 185                 190

Lys Gln Lys Val Glu Gln Pro Gln Pro Leu Pro Pro Gly Gln Val Glu
        195                 200                 205

Arg Phe Lys Asp Glu Lys Glu Lys Ala Phe Leu Val Gly Ala Glu Leu
    210                 215                 220

Ser Tyr Ala Gly Leu Ala Leu Gly Val Asp Tyr Ala Gln Ser Lys Val
225                 230                 235                 240

Thr Asn Val Asp Gly Lys Lys Arg Ala Leu Glu Val Gly Leu Lys Tyr
                245                 250                 255

Asp Leu Asn Asp Lys Ala Lys Val Tyr Thr Asp Phe Ile Trp Glu Lys
            260                 265                 270

Glu Gly Pro Lys Gly Asp Val Glu Arg Thr Arg Thr Val Ala Val Gly
        275                 280                 285

Phe Gly Tyr Lys Leu His Lys Gln Val Glu Thr Phe Val Glu Gly Ala
    290                 295                 300

Trp Gly Arg Thr Lys Asp Ala Asp Gly Thr Thr Thr Lys Asp Asn Val
305                 310                 315                 320

Val Gly Thr Gly Leu Arg Val His Phe
                325

<210> SEQ ID NO 36
<211> LENGTH: 323
<212> TYPE: PRT
<213> ORGANISM: Pasteurella multocida

<400> SEQUENCE: 36

Ala Thr Val Tyr Asn Gln Asp Gly Thr Lys Val Asp Val Asn Gly Ser
 1               5                  10                  15

Val Arg Leu Ile Leu Lys Lys Glu Lys Asn Glu Arg Gly Asp Leu Val
            20                  25                  30

Asp Asn Gly Ser Arg Val Ser Phe Lys Ala Ser His Asp Leu Gly Glu
        35                  40                  45

Gly Leu Ser Ala Leu Ala Tyr Ala Glu Leu Arg Phe Ser Thr Lys Glu
    50                  55                  60

Lys Val Glu Val Lys Asp Thr Gln Asn Gln Gln Gln Val Val Arg Thr
65                  70                  75                  80
```

-continued

```
Tyr Glu Val Glu Lys Ile Gly Asn Asp Val His Val Lys Arg Leu Tyr
                85                  90                  95

Ala Gly Phe Ala Tyr Glu Gly Leu Gly Thr Leu Thr Phe Gly Asn Gln
            100                 105                 110

Leu Thr Ile Gly Asp Asp Val Gly Val Ser Asp Tyr Thr Tyr Phe Leu
        115                 120                 125

Gly Gly Ile Asn Asn Leu Leu Ser Ser Gly Glu Lys Ala Ile Asn Phe
    130                 135                 140

Lys Ser Ala Glu Phe Asn Gly Phe Thr Phe Gly Gly Ala Tyr Val Phe
145                 150                 155                 160

Ser Ala Asp Ala Asp Lys Gln Ala Pro Arg Asp Gly Arg Gly Phe Val
                165                 170                 175

Val Ala Gly Leu Tyr Asn Arg Lys Met Gly Asp Val Gly Phe Ala Leu
            180                 185                 190

Glu Ala Gly Tyr Ser Gln Lys Tyr Val Thr Ala Ala Ala Lys Gln Glu
        195                 200                 205

Lys Glu Lys Ala Phe Met Val Gly Thr Glu Leu Ser Tyr Ala Gly Leu
    210                 215                 220

Ala Leu Gly Val Asp Tyr Ala Gln Ser Lys Val Thr Asn Val Asp Gly
225                 230                 235                 240

Lys Lys Arg Ala Leu Glu Val Gly Leu Asn Tyr Asp Ile Asn Asp Lys
                245                 250                 255

Ala Lys Val Tyr Thr Asp Leu Ile Trp Ala Lys Lys Gly Pro Lys Gly
            260                 265                 270

Ala Thr Thr Arg Asp Arg Ser Ile Ile Leu Gly Ala Gly Tyr Lys Leu
        275                 280                 285

His Lys Gln Val Glu Thr Phe Val Glu Gly Gly Trp Gly Arg Glu Lys
    290                 295                 300

Asp Ala Asn Gly Val Thr Thr Lys Asp Asn Val Val Gly Val Gly Leu
305                 310                 315                 320

Arg Val His

<210> SEQ ID NO 37
<211> LENGTH: 328
<212> TYPE: PRT
<213> ORGANISM: Pasteurella multocida

<400> SEQUENCE: 37

Ala Thr Val Tyr Asn Gln Asp Gly Thr Lys Val Asp Val Asn Gly Ser
 1               5                  10                  15

Val Arg Leu Leu Leu Lys Lys Glu Lys Asp Lys Arg Gly Asp Leu Met
            20                  25                  30

Asp Asn Gly Ser Arg Val Ser Phe Lys Ala Ser His Asp Leu Gly Glu
        35                  40                  45

Gly Leu Ser Ala Leu Ala Tyr Ala Glu Leu Arg Phe Ser Lys Asp Val
    50                  55                  60

Lys Asn Lys Asp Gly Glu Val Ile Lys Gln Pro Ile Gly Asn Asn Val
65                  70                  75                  80

His Ala Lys Arg Leu Tyr Ala Gly Phe Ala Tyr Glu Gly Val Gly Thr
                85                  90                  95

Leu Thr Phe Gly Asn Gln Leu Thr Ile Gly Asp Asp Val Gly Val Ser
            100                 105                 110

Asp Tyr Thr Tyr Phe Leu Gly Gly Ile Asn Asn Leu Leu Ser Ser Gly
        115                 120                 125
```

-continued

```
Glu Lys Ala Ile Asn Phe Lys Ser Ala Glu Phe Asn Gly Leu Thr Phe
    130                 135                 140

Gly Gly Thr Tyr Val Phe Ser Asp Asp Phe Asp Lys Asn Gly Leu Arg
145                 150                 155                 160

Asp Gly Arg Gly Phe Val Val Ala Gly Leu Tyr Asn Arg Lys Ile Gly
                165                 170                 175

Asp Val Gly Phe Ala Phe Glu Ala Gly Tyr Ser Gln Lys Tyr Val Lys
            180                 185                 190

Gln Glu Val Ala Ser Val Leu Pro Ala Pro Ser Gly Ser Val Thr Val
        195                 200                 205

Tyr Lys Asp Glu Lys Glu Lys Ala Phe Met Val Gly Ala Glu Leu Ser
    210                 215                 220

Tyr Ala Gly Leu Ala Leu Gly Val Asp Tyr Ala Gln Ser Lys Val Thr
225                 230                 235                 240

Asn Val Asp Gly Lys Lys Arg Ala Leu Glu Val Gly Leu Asn Tyr Asp
                245                 250                 255

Ile Asn Asp Lys Ala Lys Val Tyr Thr Asp Phe Ile Trp Ala Lys Glu
            260                 265                 270

Gly Pro Lys Gly Ala Thr Thr Arg Asp Arg Ser Ile Ile Leu Gly Ala
        275                 280                 285

Gly Tyr Lys Leu His Lys Gln Val Glu Thr Phe Val Glu Gly Gly Trp
    290                 295                 300

Gly Arg Glu Lys Asp Ala Asn Gly Val Thr Thr Lys Asp Asn Val Val
305                 310                 315                 320

Gly Val Gly Leu Arg Val His Phe
                325

<210> SEQ ID NO 38
<211> LENGTH: 319
<212> TYPE: PRT
<213> ORGANISM: Pasteurella multocida

<400> SEQUENCE: 38

Ala Thr Val Tyr Asn Gln Asp Gly Thr Lys Val Asp Val Asn Gly Ser
 1               5                  10                  15

Val Arg Leu Ile Leu Lys Lys Glu Lys Asn Glu Arg Gly Asp Leu Val
            20                  25                  30

Asp Asn Gly Ser Arg Val Ser Phe Lys Ala Ser His Asp Leu Gly Glu
        35                  40                  45

Gly Leu Ser Ala Leu Ala Tyr Thr Glu Leu Arg Phe Ser Lys Asn Val
    50                  55                  60

Thr Val Gln Val Lys Asp Pro Gln Gly Lys Val Val Arg Glu Tyr Asp
65                  70                  75                  80

Val Glu Lys Leu Gly Asn Asn Val His Val Lys Arg Leu Tyr Ala Gly
                85                  90                  95

Phe Ala Tyr Glu Gly Leu Gly Thr Leu Thr Phe Gly Asn Gln Leu Thr
            100                 105                 110

Ile Gly Asp Asp Val Gly Val Ser Asp Tyr Thr Tyr Phe Leu Gly Gly
        115                 120                 125

Ile Asn Asn Leu Leu Ser Ser Gly Glu Lys Ala Ile Asn Phe Lys Ser
    130                 135                 140

Ala Glu Phe Asn Gly Phe Thr Phe Gly Gly Ala Tyr Val Phe Ser Ala
145                 150                 155                 160

Asp Ala Asp Lys Gln Ala Pro Arg Asp Gly Arg Gly Phe Val Val Ala
```

```
                       165                 170                 175
Gly Leu Tyr Asn Arg Lys Met Gly Asp Val Gly Phe Ala Leu Glu Ala
                180                 185                 190

Gly Tyr Ser Gln Lys Tyr Val Thr Val Ala Lys Gln Glu Lys Ala Phe
            195                 200                 205

Met Val Gly Thr Glu Leu Ser Tyr Ala Gly Leu Ala Leu Gly Val Asp
        210                 215                 220

Tyr Ala Gln Ser Lys Val Thr Asn Val Glu Gly Lys Lys Arg Ala Leu
225                 230                 235                 240

Glu Val Gly Leu Asn Tyr Asp Ile Asn Asp Lys Ala Lys Val Tyr Thr
                245                 250                 255

Asp Leu Ile Trp Ala Lys Glu Gly Pro Lys Gly Ala Thr Thr Arg Asp
            260                 265                 270

Arg Ala Ile Ile Leu Gly Ala Gly Tyr Lys Leu His Lys Gln Val Glu
        275                 280                 285

Thr Phe Val Glu Gly Gly Trp Gly Arg Glu Lys Asp Ala Asn Gly Val
    290                 295                 300

Thr Thr Lys Asp Asn Lys Val Gly Val Gly Leu Arg Val His Phe
305                 310                 315

<210> SEQ ID NO 39
<211> LENGTH: 328
<212> TYPE: PRT
<213> ORGANISM: Pasteurella multocida

<400> SEQUENCE: 39

Ala Thr Val Tyr Asn Gln Asp Gly Thr Lys Val Asp Val Asn Gly Ser
1               5                   10                  15

Val Arg Leu Leu Leu Lys Lys Glu Lys Asp Lys Arg Gly Asp Leu Met
                20                  25                  30

Asp Asn Gly Ser Arg Val Ser Phe Lys Ala Ser His Asp Leu Gly Glu
            35                  40                  45

Gly Leu Ser Ala Leu Ala Tyr Ala Glu Leu Arg Phe Ser Lys Asp Val
        50                  55                  60

Lys Asn Lys Asp Gly Glu Val Ile Lys Gln Pro Ile Gly Asn Asn Val
65                  70                  75                  80

His Ala Lys Arg Leu Tyr Ala Gly Phe Ala Tyr Glu Gly Val Gly Thr
                85                  90                  95

Leu Thr Phe Gly Asn Gln Leu Thr Ile Gly Asp Asp Val Gly Val Ser
            100                 105                 110

Asp Tyr Thr Tyr Phe Leu Gly Gly Ile Asn Asn Leu Leu Ser Ser Gly
        115                 120                 125

Glu Lys Ala Ile Asn Phe Lys Ser Ala Glu Phe Asn Gly Leu Thr Phe
    130                 135                 140

Gly Gly Ala Tyr Val Phe Ser Asp Asp Phe Asp Lys Asn Gly Leu Arg
145                 150                 155                 160

Asp Gly Arg Gly Phe Val Val Ala Gly Leu Tyr Asn Arg Lys Ile Gly
                165                 170                 175

Asp Val Gly Phe Ala Phe Glu Ala Gly Tyr Ser Gln Lys Tyr Val Lys
            180                 185                 190

Gln Glu Val Ala Ser Val Leu Pro Ala Pro Ser Gly Ser Val Thr Val
        195                 200                 205

Tyr Lys Asp Glu Lys Glu Lys Ala Phe Met Val Gly Ala Glu Leu Ser
    210                 215                 220
```

```
Tyr Ala Gly Leu Ala Leu Gly Val Asp Tyr Ala Gln Ser Lys Val Thr
225                 230                 235                 240

Asn Val Asp Gly Lys Lys Arg Ala Leu Glu Val Gly Leu Asn Tyr Asp
                245                 250                 255

Ile Asn Asp Lys Ala Lys Val Tyr Thr Asp Phe Ile Trp Ala Lys Glu
                260                 265                 270

Gly Pro Lys Gly Ala Thr Thr Arg Asp Arg Ser Ile Ile Leu Gly Ala
                275                 280                 285

Gly Tyr Lys Leu His Lys Gln Val Glu Thr Phe Val Glu Gly Gly Trp
290                 295                 300

Gly Arg Glu Lys Asp Ala Asn Gly Val Thr Thr Lys Asp Asn Val Val
305                 310                 315                 320

Gly Val Gly Leu Arg Val His Phe
                325
```

<210> SEQ ID NO 40
<211> LENGTH: 329
<212> TYPE: PRT
<213> ORGANISM: Pasteurella multocida

<400> SEQUENCE: 40

```
Ala Thr Val Tyr Asn Gln Asp Gly Thr Lys Val Asp Val Asn Gly Ser
1               5                   10                  15

Val Arg Leu Leu Leu Lys Lys Glu Lys Asp Met Arg Gly Asp Leu Ile
                20                  25                  30

Asp Asn Gly Ser Arg Val Ser Phe Lys Ala Ser His Asp Leu Gly Glu
                35                  40                  45

Gly Leu Ser Ala Leu Gly Tyr Ala Glu Leu Arg Phe Ser Asp Asp Val
50              55                  60

Lys Asp Lys Asp Gly Asn Val Val Asn Gln Pro Ile Gly Asn Lys Val
65                  70                  75                  80

His Ala Lys Arg Leu Tyr Ala Gly Phe Ala Tyr Glu Gly Leu Gly Thr
                85                  90                  95

Leu Thr Phe Gly Asn Gln Leu Thr Ile Gly Asp Asp Val Gly Val Ser
                100                 105                 110

Asp Tyr Thr Tyr Phe Asn Ser Gly Ile Asn Gly Val Leu Ile Thr Ser
                115                 120                 125

Gly Gln Lys Ala Ile Asn Phe Lys Ser Ala Glu Phe Asn Gly Phe Thr
130                 135                 140

Phe Gly Gly Ala Tyr Val Phe Ser Gly Asp Ala Asn Lys Asp Ala Leu
145                 150                 155                 160

Arg Asp Gly Arg Gly Phe Val Val Ala Gly Leu Tyr Asn Arg Gln Ile
                165                 170                 175

Gly Asp Val Gly Phe Ala Phe Glu Ala Gly Tyr Ser Gln Lys Tyr Val
                180                 185                 190

Lys Gln Lys Val Glu Gln Pro Gln Pro Leu Pro Ser Gly Gln Val Glu
                195                 200                 205

Arg Phe Lys Asp Glu Lys Lys Ala Phe Leu Val Gly Ala Glu Leu
                210                 215                 220

Ser Tyr Ala Gly Leu Ala Leu Gly Val Asp Tyr Ala Gln Ser Lys Val
225                 230                 235                 240

Thr Asn Val Asp Gly Lys Lys Arg Leu Glu Val Gly Leu Lys Tyr
                245                 250                 255

Asp Leu Asn Asp Lys Ala Lys Val Tyr Thr Asp Phe Ile Trp Glu Lys
                260                 265                 270
```

```
Glu Gly Pro Lys Gly Asp Val Glu Arg Thr Arg Thr Val Ala Val Gly
            275                 280                 285
Phe Gly Tyr Lys Leu His Lys Gln Val Glu Thr Phe Val Glu Gly Ala
        290                 295                 300
Trp Gly Arg Thr Lys Asp Ala Asp Gly Thr Thr Lys Asp Asn Val
305                 310                 315                 320
Val Gly Thr Gly Leu Arg Val His Phe
                325

<210> SEQ ID NO 41
<211> LENGTH: 333
<212> TYPE: PRT
<213> ORGANISM: Pasteurella multocida

<400> SEQUENCE: 41

Ala Thr Val Tyr Asn Gln Asp Gly Thr Lys Val Asp Val Asn Gly Ser
1               5                   10                  15
Leu Arg Leu Ile Leu Lys Lys Glu Lys Asn Glu Arg Gly Asp Leu Val
            20                  25                  30
Asp Asn Gly Ser Arg Val Ser Phe Lys Ala Ser His Asp Leu Gly Glu
        35                  40                  45
Gly Leu Ser Ala Leu Ala Tyr Thr Glu Leu Arg Phe Ser Lys Asn Val
    50                  55                  60
Pro Val Gln Val Lys Asp Gln Gln Gly Glu Val Val Arg Glu Tyr Glu
65                  70                  75                  80
Val Glu Lys Leu Gly Asn Asn Val His Val Lys Arg Leu Tyr Ala Gly
                85                  90                  95
Phe Ala Tyr Glu Gly Leu Gly Thr Leu Thr Phe Gly Asn Gln Leu Thr
            100                 105                 110
Ile Gly Asp Asp Val Gly Leu Ser Asp Tyr Thr Tyr Phe Asn Ser Gly
        115                 120                 125
Ile Asn Asn Leu Leu Ser Ser Gly Glu Lys Ala Ile Asn Phe Lys Ser
    130                 135                 140
Ala Glu Phe Asn Gly Phe Thr Phe Gly Gly Ala Tyr Val Phe Ser Ala
145                 150                 155                 160
Asp Ala Asp Lys Gln Ala Leu Arg Asp Gly Arg Gly Phe Val Val Ala
                165                 170                 175
Gly Leu Tyr Asn Arg Lys Met Gly Asp Val Gly Phe Ala Phe Glu Ala
            180                 185                 190
Gly Tyr Ser Gln Lys Tyr Val Lys Gln Glu Val Glu Gln Asn Pro Pro
        195                 200                 205
Ala Ala Gln Lys Val Phe Lys Asp Glu Lys Glu Lys Ala Phe Met Val
    210                 215                 220
Gly Ala Glu Leu Ser Tyr Ala Gly Leu Ala Leu Gly Val Asp Tyr Ala
225                 230                 235                 240
Gln Ser Lys Val Thr Asn Val Asp Gly Lys Lys Arg Ala Leu Glu Val
                245                 250                 255
Gly Leu Asn Tyr Asp Leu Asn Asp Arg Ala Lys Val Tyr Thr Asp Phe
            260                 265                 270
Ile Trp Glu Lys Glu Gly Pro Lys Gly Asp Val Thr Arg Asn Arg Thr
        275                 280                 285
Val Ala Val Gly Phe Gly Tyr Lys Leu His Lys Gln Val Glu Thr Phe
    290                 295                 300
Val Glu Ala Ala Trp Gly Arg Glu Lys Asp Ser Asp Gly Val Thr Thr
```

```
305                 310                 315                 320
Lys Asn Asn Val Val Gly Thr Gly Leu Arg Val His Phe
                325                 330

<210> SEQ ID NO 42
<211> LENGTH: 318
<212> TYPE: PRT
<213> ORGANISM: Pasteurella multocida

<400> SEQUENCE: 42

Ala Thr Val Tyr Asn Gln Asp Gly Thr Glu Val Asp Val Asn Gly Ser
  1               5                  10                  15

Val Ser Leu Ile Leu Lys Lys Glu Lys Asp Lys Arg Gly Asp Leu Val
            20                  25                  30

Asp Asn Gly Ser Arg Val Ser Phe Lys Ala Ser His Asp Leu Gly Glu
        35                  40                  45

Gly Leu Ser Ala Leu Ala Tyr Ala Glu Leu Arg Phe Ser Thr Lys Glu
    50                  55                  60

Glu Val Glu Val Thr Gln Asn Gln Lys Val Val Arg Lys Tyr Glu Val
65                  70                  75                  80

Glu Arg Ile Gly Asn Asp Val His Val Lys Arg Leu Tyr Ala Gly Phe
                85                  90                  95

Ala Tyr Glu Gly Leu Gly Thr Leu Thr Phe Gly Asn Gln Leu Thr Ile
            100                 105                 110

Gly Asp Asp Val Gly Val Ser Asp Tyr Thr Tyr Phe Leu Gly Gly Ile
        115                 120                 125

Asn Asn Leu Leu Ser Ser Gly Glu Lys Ala Ile Asn Phe Lys Ser Ala
    130                 135                 140

Glu Phe Asn Gly Phe Thr Phe Gly Gly Ala Tyr Val Phe Ser Ala Gly
145                 150                 155                 160

Ala Asp Lys Gln Ala Ala Arg Asp Gly Arg Gly Phe Val Val Ala Gly
                165                 170                 175

Leu Tyr Asn Arg Lys Met Gly Asp Val Gly Phe Ala Leu Glu Ala Gly
            180                 185                 190

Tyr Ser Gln Glu Tyr Val Thr Glu Thr Ala Lys Gln Glu Lys Ala Phe
        195                 200                 205

Met Val Gly Thr Glu Leu Ser Tyr Ala Gly Leu Ala Leu Gly Val Asp
    210                 215                 220

Tyr Ala Gln Ser Lys Val Thr Asn Val Asp Gly Lys Lys Arg Ala Leu
225                 230                 235                 240

Glu Val Gly Leu Asn Tyr Asp Leu Asn Asp Lys Ala Lys Val Tyr Thr
                245                 250                 255

Asp Leu Ile Trp Ala Lys Lys Gly Pro Lys Gly Ala Thr Thr Arg Asp
            260                 265                 270

Arg Ala Ile Ile Leu Gly Ala Gly Tyr Lys Leu His Lys Gln Val Glu
        275                 280                 285

Thr Phe Val Glu Gly Gly Tyr Arg Thr Lys Asn Ala Ala Gly Val Thr
    290                 295                 300

Thr Lys Asp Asn Lys Val Gly Val Gly Leu Arg Val His Phe
305                 310                 315

<210> SEQ ID NO 43
<211> LENGTH: 322
<212> TYPE: PRT
<213> ORGANISM: Pasteurella multocida
```

-continued

```
<400> SEQUENCE: 43

Ala Thr Val Tyr Asn Gln Asp Gly Thr Lys Val Asp Val Asn Gly Ser
 1               5                  10                  15

Val Arg Leu Ile Leu Lys Lys Glu Lys Asn Glu Arg Gly Asp Leu Val
             20                  25                  30

Asp Asn Gly Ser Arg Val Ser Phe Lys Ala Ser His Asp Leu Gly Glu
         35                  40                  45

Gly Leu Ser Ala Leu Ala Tyr Ala Glu Leu Arg Phe Ser Thr Lys Val
     50                  55                  60

Lys Lys Thr Val Lys Glu Gly Pro Asn Gln Val Glu Arg Thr Tyr Glu
 65                  70                  75                  80

Val Glu Arg Ile Gly Asn Asp Val His Val Lys Arg Leu Tyr Ala Gly
                 85                  90                  95

Phe Ala Tyr Glu Gly Leu Gly Thr Leu Thr Phe Gly Asn Gln Leu Thr
            100                 105                 110

Ile Gly Asp Asp Val Gly Val Ser Asp Tyr Thr Tyr Phe Leu Gly Gly
        115                 120                 125

Ile Asn Asn Leu Leu Ser Ser Gly Glu Lys Ala Ile Asn Phe Lys Ser
    130                 135                 140

Ala Glu Phe Asn Gly Phe Thr Phe Gly Gly Ala Tyr Val Phe Ser Ala
145                 150                 155                 160

Asp Ala Asp Lys Gln Ala Pro Arg Asp Gly Arg Gly Phe Val Val Ala
                165                 170                 175

Gly Leu Tyr Asn Arg Lys Met Gly Asp Val Gly Phe Ala Leu Glu Ala
            180                 185                 190

Gly Tyr Ser Gln Lys Tyr Val Thr Ala Ala Lys Gln Glu Lys Glu
        195                 200                 205

Lys Ala Phe Met Val Gly Thr Glu Leu Ser Tyr Ala Gly Leu Ala Leu
    210                 215                 220

Gly Val Asp Tyr Ala Gln Ser Lys Val Thr Asn Val Glu Gly Lys Lys
225                 230                 235                 240

Arg Ala Leu Glu Val Gly Leu Asn Tyr Asp Ile Asn Asp Lys Ala Lys
                245                 250                 255

Val Tyr Thr Asp Leu Ile Trp Ala Lys Glu Gly Pro Lys Gly Ala Thr
            260                 265                 270

Thr Arg Asp Arg Ser Ile Ile Leu Gly Ala Gly Tyr Lys Leu His Lys
        275                 280                 285

Gln Val Glu Thr Phe Val Glu Gly Gly Trp Gly Arg Glu Lys Asp Ala
    290                 295                 300

Asn Gly Val Thr Thr Lys Asp Asn Lys Val Gly Val Gly Leu Arg Val
305                 310                 315                 320

His Phe

<210> SEQ ID NO 44
<211> LENGTH: 22
<212> TYPE: PRT
<213> ORGANISM: Pasteurella multocida

<400> SEQUENCE: 44

Lys Tyr Val Lys Gln Glu Val Glu Gln Asn Pro Pro Ala Ala Gln Lys
 1               5                  10                  15

Val Phe L

```
<210> SEQ ID NO 45
<211> LENGTH: 30
<212> TYPE: PRT
<213> ORGANISM: Pasteurella multocida

<400> SEQUENCE: 45

Ser Lys Asn Val Pro Val Gln Val Lys Asp Gln Gln Gly Glu Val Val
 1               5                  10                  15

Arg Glu Tyr Glu Val Glu Lys Leu Gly Asn Asn Val His Val
             20                  25                  30

<210> SEQ ID NO 46
<211> LENGTH: 340
<212> TYPE: PRT
<213> ORGANISM: Escherichia coli

<400> SEQUENCE: 46

Ala Glu Ile Tyr Asn Lys Asp Gly Asn Lys Val Asp Leu Tyr Gly Lys
 1               5                  10                  15

Ala Val Gly Leu His Tyr Phe Ser Lys Gly Asn Gly Glu Asn Ser Tyr
             20                  25                  30

Gly Gly Asn Gly Asp Met Thr Tyr Ala Arg Leu Gly Phe Lys Gly Glu
         35                  40                  45

Thr Gln Ile Asn Ser Asp Leu Thr Gly Tyr Gly Gln Trp Glu Tyr Asn
     50                  55                  60

Phe Gln Gly Asn Asn Ser Glu Gly Ala Asp Ala Gln Thr Gly Asn Lys
65                  70                  75                  80

Thr Arg Leu Ala Phe Ala Gly Leu Lys Tyr Ala Asp Val Gly Ser Phe
                 85                  90                  95

Asp Tyr Gly Arg Asn Tyr Gly Val Val Tyr Asp Ala Leu Gly Tyr Thr
            100                 105                 110

Asp Met Leu Pro Glu Phe Gly Gly Asp Thr Ala Tyr Ser Asp Asp Phe
        115                 120                 125

Phe Val Gly Arg Val Gly Gly Val Ala Thr Tyr Arg Asn Ser Asn Phe
    130                 135                 140

Phe Gly Leu Val Asp Gly Leu Asn Phe Ala Val Gln Tyr Leu Gly Lys
145                 150                 155                 160

Asn Glu Arg Asp Thr Ala Arg Arg Ser Asn Gly Asp Gly Val Gly Gly
                165                 170                 175

Ser Ile Ser Tyr Glu Tyr Glu Gly Phe Gly Ile Val Gly Ala Tyr Gly
            180                 185                 190

Ala Ala Asp Arg Thr Asn Leu Gln Glu Ala Gln Pro Leu Gly Asn Gly
        195                 200                 205

Lys Lys Ala Glu Gln Trp Ala Thr Gly Leu Lys Tyr Asp Ala Asn Asn
    210                 215                 220

Ile Tyr Leu Ala Ala Asn Tyr Gly Glu Thr Arg Asn Ala Thr Pro Ile
225                 230                 235                 240

Thr Asn Lys Phe Thr Asn Thr Ser Gly Phe Ala Asn Lys Thr Gln Asp
                245                 250                 255

Val Leu Leu Val Ala Gln Tyr Gln Phe Asp Phe Gly Leu Arg Pro Ser
            260                 265                 270

Ile Ala Tyr Thr Lys Ser Lys Ala Lys Asp Val Glu Gly Ile Gly Asp
        275                 280                 285

Val Asp Leu Val Asn Tyr Phe Glu Val Gly Ala Thr Tyr Tyr Phe Asn
    290                 295                 300

Lys Asn Met Ser Thr Tyr Val Asp Tyr Ile Ile Asn Gln Ile Asp Ser
```

```
305                 310                 315                 320
Asp Asn Lys Leu Gly Val Gly Ser Asp Asp Thr Val Ala Val Gly Ile
                325                 330                 335

Val Tyr Gln Phe
            340

<210> SEQ ID NO 47
<211> LENGTH: 330
<212> TYPE: PRT
<213> ORGANISM: Escherichia coli

<400> SEQUENCE: 47

Ala Glu Ile Tyr Asn Lys Asp Gly Asn Lys Leu Asp Val Tyr Gly Lys
  1               5                  10                  15

Val Lys Ala Met His Tyr Met Ser Asp Asn Ala Ser Lys Asp Gly Asp
                 20                  25                  30

Gln Ser Tyr Ile Arg Phe Gly Phe Lys Gly Glu Thr Gln Ile Asn Asp
             35                  40                  45

Gln Leu Thr Gly Tyr Gly Arg Trp Glu Ala Glu Phe Ala Gly Asn Lys
         50                  55                  60

Ala Glu Ser Asp Thr Ala Gln Gln Lys Thr Arg Leu Ala Phe Ala Gly
 65                  70                  75                  80

Leu Lys Tyr Lys Asp Leu Gly Ser Phe Asp Tyr Gly Arg Asn Leu Gly
                 85                  90                  95

Ala Leu Tyr Asp Val Glu Ala Trp Thr Asp Met Phe Pro Glu Phe Gly
            100                 105                 110

Gly Asp Ser Ser Ala Gln Thr Asp Asn Phe Met Thr Lys Arg Ala Ser
            115                 120                 125

Gly Leu Ala Thr Tyr Arg Asn Thr Asp Phe Phe Gly Val Ile Asp Gly
        130                 135                 140

Leu Asn Leu Thr Leu Gln Tyr Gln Gly Lys Asn Glu Asn Arg Asp Val
145                 150                 155                 160

Lys Lys Gln Asn Gly Asp Gly Phe Gly Thr Ser Leu Thr Tyr Asp Phe
                165                 170                 175

Gly Gly Ser Asp Phe Ala Ile Ser Gly Ala Tyr Thr Asn Ser Asp Arg
            180                 185                 190

Thr Asn Glu Gln Asn Leu Gln Ser Arg Gly Thr Gly Lys Arg Ala Glu
        195                 200                 205

Ala Trp Ala Thr Gly Leu Lys Tyr Asp Ala Asn Asn Ile Tyr Leu Ala
    210                 215                 220

Thr Phe Tyr Ser Glu Thr Arg Lys Met Thr Pro Ile Thr Gly Gly Phe
225                 230                 235                 240

Ala Asn Lys Thr Gln Asn Phe Glu Ala Val Ala Gln Tyr Gln Phe Asp
                245                 250                 255

Phe Gly Leu Arg Pro Ser Leu Gly Tyr Val Leu Ser Lys Gly Lys Asp
            260                 265                 270

Ile Glu Gly Ile Gly Asp Glu Asp Leu Val Asn Tyr Ile Asp Val Gly
        275                 280                 285

Ala Thr Tyr Tyr Phe Asn Lys Asn Met Ser Ala Phe Val Asp Tyr Lys
    290                 295                 300

Ile Asn Gln Leu Asp Ser Asp Asn Lys Leu Asn Ile Asn Asn Asp Asp
305                 310                 315                 320

Ile Val Ala Val Gly Met Thr Tyr Gln Phe
                325                 330
```

<210> SEQ ID NO 48
<211> LENGTH: 289
<212> TYPE: PRT
<213> ORGANISM: Rhodobacter blasticus

<400> SEQUENCE: 48

| Glu | Ile | Ser | Leu | Asn | Gly | Tyr | Gly | Arg | Phe | Gly | Leu | Gln | Tyr | Val | Glu |
| 1 | | | | 5 | | | | | 10 | | | | | 15 | |

| Asp | Arg | Gly | Val | Gly | Leu | Glu | Asp | Thr | Ile | Ile | Ser | Ser | Arg | Leu | Arg |
| | | | 20 | | | | | 25 | | | | | 30 | | |

| Ile | Asn | Ile | Val | Gly | Thr | Thr | Glu | Thr | Asp | Gln | Gly | Val | Thr | Phe | Gly |
| | | 35 | | | | | 40 | | | | | 45 | | | |

| Ala | Lys | Leu | Arg | Met | Gln | Trp | Asp | Asp | Gly | Asp | Ala | Phe | Ala | Gly | Thr |
| | 50 | | | | | 55 | | | | | 60 | | | | |

| Ala | Gly | Asn | Ala | Ala | Gln | Phe | Trp | Thr | Ser | Tyr | Asn | Gly | Val | Thr | Val |
| 65 | | | | | 70 | | | | | 75 | | | | | 80 |

| Ser | Val | Gly | Asn | Val | Asp | Thr | Ala | Phe | Asp | Ser | Val | Ala | Leu | Thr | Tyr |
| | | | | 85 | | | | | 90 | | | | | 95 | |

| Asp | Ser | Glu | Met | Gly | Tyr | Glu | Ala | Ser | Ser | Phe | Gly | Asp | Ala | Gln | Ser |
| | | | | 100 | | | | | 105 | | | | | 110 | |

| Ser | Phe | Phe | Ala | Tyr | Asn | Ser | Lys | Tyr | Asp | Ala | Ser | Gly | Ala | Leu | Asp |
| | | | 115 | | | | | 120 | | | | | 125 | | |

| Asn | Tyr | Asn | Gly | Ile | Ala | Val | Thr | Tyr | Ser | Ile | Ser | Gly | Val | Asn | Leu |
| | 130 | | | | | 135 | | | | | 140 | | | | |

| Tyr | Leu | Ser | Tyr | Val | Asp | Pro | Asp | Gln | Thr | Val | Asp | Ser | Ser | Leu | Val |
| 145 | | | | | 150 | | | | | 155 | | | | | 160 |

| Thr | Glu | Glu | Phe | Gly | Ile | Ala | Ala | Asp | Trp | Ser | Asn | Asp | Met | Ile | Ser |
| | | | | 165 | | | | | 170 | | | | | 175 | |

| Leu | Ala | Ala | Ala | Tyr | Thr | Thr | Asp | Ala | Gly | Gly | Ile | Val | Asp | Asn | Asp |
| | | | | 180 | | | | | 185 | | | | | 190 | |

| Ile | Ala | Phe | Val | Gly | Ala | Ala | Tyr | Lys | Phe | Asn | Asp | Ala | Gly | Thr | Val |
| | | | 195 | | | | | 200 | | | | | 205 | | |

| Gly | Leu | Asn | Trp | Tyr | Asp | Asn | Gly | Leu | Ser | Thr | Ala | Gly | Asp | Gln | Val |
| | 210 | | | | | 215 | | | | | 220 | | | | |

| Thr | Leu | Tyr | Gly | Asn | Tyr | Ala | Phe | Gly | Ala | Thr | Thr | Val | Arg | Ala | Tyr |
| 225 | | | | | 230 | | | | | 235 | | | | | 240 |

| Val | Ser | Asp | Ile | Asp | Arg | Ala | Gly | Ala | Asp | Thr | Ala | Tyr | Gly | Ile | Gly |
| | | | | 245 | | | | | 250 | | | | | 255 | |

| Ala | Asp | Tyr | Gln | Phe | Ala | Glu | Gly | Val | Lys | Val | Ser | Gly | Ser | Val | Gln |
| | | | 260 | | | | | 265 | | | | | 270 | | |

| Ser | Gly | Phe | Ala | Asn | Glu | Thr | Val | Ala | Asp | Val | Gly | Val | Arg | Phe | Asp |
| | | | 275 | | | | | 280 | | | | | 285 | | |

| Phe | | | | | | | | | | | | | | | |

<210> SEQ ID NO 49
<211> LENGTH: 289
<212> TYPE: PRT
<213> ORGANISM: Rhodobacter blasticus

<400> SEQUENCE: 49

| Glu | Ile | Ser | Leu | Asn | Gly | Tyr | Gly | Arg | Phe | Gly | Leu | Gln | Tyr | Val | Glu |
| 1 | | | | 5 | | | | | 10 | | | | | 15 | |

| Asp | Arg | Gly | Val | Gly | Leu | Glu | Asp | Thr | Ile | Ile | Ser | Ser | Arg | Leu | Arg |
| | | | 20 | | | | | 25 | | | | | 30 | | |

| Ile | Asn | Ile | Val | Gly | Thr | Thr | Glu | Thr | Asp | Gln | Gly | Val | Thr | Phe | Gly |

-continued

```
            35                  40                  45
Ala Lys Leu Arg Met Gln Trp Asp Asp Gly Asp Ala Phe Ala Gly Thr
        50                  55                  60
Ala Gly Asn Ala Ala Gln Phe Trp Thr Ser Tyr Asn Gly Val Thr Val
 65                  70                  75                  80
Ser Val Gly Asn Val Asp Thr Ala Phe Asp Ser Val Ala Leu Thr Tyr
                 85                  90                  95
Asp Ser Glu Met Gly Tyr Glu Ala Ser Ser Phe Gly Asp Ala Gln Ser
            100                 105                 110
Ser Phe Phe Ala Tyr Asn Ser Lys Tyr Asp Ala Ser Gly Ala Leu Asp
            115                 120                 125
Asn Tyr Asn Gly Ile Ala Val Thr Tyr Ser Ile Ser Gly Val Asn Leu
        130                 135                 140
Tyr Leu Ser Tyr Val Asp Pro Asp Gln Thr Val Asp Ser Ser Leu Val
145                 150                 155                 160
Thr Glu Glu Phe Gly Ile Ala Ala Asp Trp Ser Asn Asp Met Ile Ser
                165                 170                 175
Leu Ala Ala Ala Tyr Thr Thr Asp Ala Gly Gly Ile Val Asp Asn Asp
            180                 185                 190
Ile Ala Phe Val Gly Ala Ala Tyr Lys Phe Asn Asp Ala Gly Thr Val
            195                 200                 205
Gly Leu Asn Trp Tyr Asp Asn Gly Leu Ser Thr Ala Gly Asp Gln Val
        210                 215                 220
Thr Leu Tyr Gly Asn Tyr Ala Phe Gly Ala Thr Thr Val Arg Ala Tyr
225                 230                 235                 240
Val Ser Asp Ile Asp Arg Ala Gly Ala Asp Thr Ala Tyr Gly Ile Gly
                245                 250                 255
Ala Asp Tyr Gln Phe Ala Glu Gly Val Lys Val Ser Gly Ser Val Gln
            260                 265                 270
Ser Gly Phe Ala Asn Glu Thr Val Ala Asp Val Gly Val Arg Phe Asp
            275                 280                 285
Phe
```

<210> SEQ ID NO 50
<211> LENGTH: 25
<212> TYPE: DNA
<213> ORGANISM: Pasteurella multocida

<400> SEQUENCE: 50
tcaactatga aaagacaat cgtag                                    25

<210> SEQ ID NO 51
<211> LENGTH: 25
<212> TYPE: DNA
<213> ORGANISM: Pasteurella multocida

<400> SEQUENCE: 51
tcacagcaac agtttacaat caaga 25

<210> SEQ ID NO 52
<211> LENGTH: 25
<212> TYPE: DNA
<213> ORGANISM: Pasteurella multocida

<400> SEQUENCE: 52
ctagatccat tccttgcaac atatt 25

<210> SEQ ID NO 53
<211> LENGTH: 22
<212> TYPE: DNA
<213> ORGANISM: Pasteurella multocida

<400> SEQUENCE: 53
actatgaaaa agacaatcgt ag                                    22

<210> SEQ ID NO 54
<211> LENGTH: 22
<212> TYPE: DNA
<213> ORGANISM: Pasteurella multocida

<400> SEQUENCE: 54
gatccattcc ttgcaacata tt                                    22

<210> SEQ ID NO 55
<211> LENGTH: 32
<212> TYPE: PRT
<213> ORGANISM: Pasteurella multocida

<400> SEQUENCE: 55

Cys Ser Lys Asn Val Pro Val Gln Val Lys Asp Gln Gln Gly Glu Val
1               5                   10                  15

Val Arg Glu Tyr Glu Val Glu Lys Leu Gly Asn Asn Val His Val Cys
            20                  25                  30

<210> SEQ ID NO 56
<211> LENGTH: 24
<212> TYPE: PRT
<213> ORGANISM: Pasteurella multocida

<400> SEQUENCE: 56

Cys Lys Tyr Val Lys Gln Glu Val Glu Gln Asn Pro Pro Ala Ala Gln
1               5                   10                  15

Lys Val Phe Lys Asp Glu Lys Cys
            20

<210> SEQ ID NO 57
<211> LENGTH: 31
<212> TYPE: PRT
<213> ORGANISM: Pasteurella multocida

<400> SEQUENCE: 57

Ser Lys Asn Glu Lys Val Glu Val Lys Asp Ala Gln Asn Gln Gln Val
1               5                   10                  15

Val Arg Lys Tyr Glu Val Glu Arg Ile Gly Asn Asp Val His Val
            20                  25                  30

<210> SEQ ID NO 58
<211> LENGTH: 11
<212> TYPE: PRT
<213> ORGANISM: Pasteurella multocida

<400> SEQUENCE: 58

Lys Tyr Val Thr Ala Ala Ala Lys Gln Glu Lys
1               5                   10

<210> SEQ ID NO 59
<211> LENGTH: 333
<212> TYPE: PRT
<213> ORGANISM: Pasteurella multocida

```
<400> SEQUENCE: 59

Ala Thr Val Tyr Asn Gln Asp Gly Thr Lys Val Asp Val Asn Gly Ser
 1               5                  10                  15

Leu Arg Leu Ile Leu Lys Lys Glu Lys Asn Glu Arg Gly Asp Leu Val
             20                  25                  30

Asp Asn Gly Ser Arg Val Ser Phe Lys Ala Ser His Asp Leu Gly Glu
         35                  40                  45

Gly Leu Ser Ala Leu Ala Tyr Thr Glu Leu Arg Phe Ser Lys Asn Val
     50                  55                  60

Pro Val Gln Val Lys Asp Gln Gln Gly Glu Val Val Arg Glu Tyr Glu
 65                  70                  75                  80

Val Glu Lys Leu Gly Asn Asn Val His Val Lys Arg Leu Tyr Ala Gly
                 85                  90                  95

Phe Ala Tyr Glu Gly Leu Gly Thr Leu Thr Phe Gly Asn Gln Leu Thr
             100                 105                 110

Ile Gly Asp Asp Val Gly Leu Ser Asp Tyr Thr Tyr Phe Asn Ser Gly
         115                 120                 125

Ile Asn Asn Leu Leu Ser Ser Gly Glu Lys Ala Ile Asn Phe Lys Ser
    130                 135                 140

Ala Glu Phe Asn Gly Phe Thr Phe Gly Gly Ala Tyr Val Phe Ser Ala
145                 150                 155                 160

Asp Ala Asp Lys Gln Ala Leu Arg Asp Gly Arg Gly Phe Val Val Ala
                165                 170                 175

Gly Leu Tyr Asn Arg Lys Met Gly Asp Val Gly Phe Ala Phe Glu Ala
            180                 185                 190

Gly Tyr Ser Gln Lys Tyr Val Lys Gln Glu Val Glu Gln Asn Pro Pro
        195                 200                 205

Ala Ala Gln Lys Val Phe Lys Asp Glu Lys Glu Lys Ala Phe Met Val
    210                 215                 220

Gly Ala Glu Leu Ser Tyr Ala Gly Leu Ala Leu Gly Val Asp Tyr Ala
225                 230                 235                 240

Gln Ser Lys Val Thr Asn Val Asp Gly Lys Lys Arg Ala Leu Glu Val
                245                 250                 255

Gly Leu Asn Tyr Asp Leu Asn Asp Arg Ala Lys Val Tyr Thr Asp Phe
            260                 265                 270

Ile Trp Glu Lys Glu Gly Pro Lys Gly Asp Val Thr Arg Asn Arg Thr
        275                 280                 285

Val Ala Val Gly Phe Gly Tyr Lys Leu His Lys Gln Val Glu Thr Phe
    290                 295                 300

Val Glu Ala Ala Trp Gly Arg Glu Lys Asp Ser Asp Gly Val Thr Thr
305                 310                 315                 320

Lys Asn Asn Val Val Gly Thr Gly Leu Arg Val His Phe
                325                 330

<210> SEQ ID NO 60
<211> LENGTH: 323
<212> TYPE: PRT
<213> ORGANISM: Pasteurella multocida

<400> SEQUENCE: 60

Ala Thr Val Tyr Asn Gln Asp Gly Thr Lys Val Asp Val Asn Gly Ser
 1               5                  10                  15

Val Arg Leu Ile Leu Lys Lys Glu Lys Asn Glu Arg Gly Asp Leu Val
             20                  25                  30
```

-continued

```
Asp Asn Gly Ser Arg Val Ser Phe Lys Ala Ser His Asp Leu Gly Glu
        35                  40                  45

Gly Leu Ser Ala Leu Ala Tyr Ala Glu Leu Arg Phe Ser Lys Asn Glu
    50                  55                  60

Lys Val Glu Val Lys Asp Ala Gln Asn Gln Gln Val Val Arg Lys Tyr
65                  70                  75                  80

Glu Val Glu Arg Ile Gly Asn Asp Val His Val Lys Arg Leu Tyr Ala
                85                  90                  95

Gly Phe Ala Tyr Glu Gly Leu Gly Thr Leu Thr Phe Gly Asn Gln Leu
            100                 105                 110

Thr Ile Gly Asp Asp Val Gly Val Ser Asp Tyr Thr Tyr Phe Leu Gly
        115                 120                 125

Gly Ile Asn Asn Leu Leu Ser Ser Gly Glu Lys Ala Ile Asn Phe Lys
    130                 135                 140

Ser Ala Glu Phe Asn Gly Phe Thr Phe Gly Gly Ala Tyr Val Phe Ser
145                 150                 155                 160

Ala Asp Ala Asp Lys Gln Ala Pro Arg Asp Gly Arg Gly Phe Val Val
                165                 170                 175

Ala Gly Leu Tyr Asn Arg Lys Met Gly Asp Val Gly Phe Ala Leu Glu
            180                 185                 190

Ala Gly Tyr Ser Gln Lys Tyr Val Thr Ala Ala Ala Lys Gln Glu Lys
        195                 200                 205

Glu Lys Ala Phe Met Val Gly Thr Glu Leu Ser Tyr Ala Gly Leu Ala
    210                 215                 220

Leu Gly Val Asp Tyr Ala Gln Ser Lys Val Thr Asn Val Glu Gly Lys
225                 230                 235                 240

Lys Arg Ala Leu Glu Val Gly Leu Asn Tyr Asp Ile Asn Asp Lys Ala
                245                 250                 255

Lys Val Tyr Thr Asp Leu Ile Trp Ala Lys Glu Gly Pro Lys Gly Ala
            260                 265                 270

Thr Thr Arg Asp Arg Ser Ile Ile Leu Gly Ala Gly Tyr Lys Leu His
        275                 280                 285

Lys Gln Val Glu Thr Phe Val Glu Gly Gly Trp Gly Arg Glu Lys Asp
    290                 295                 300

Ala Asn Gly Val Thr Thr Lys Asp Asn Lys Val Gly Val Gly Leu Arg
305                 310                 315                 320

Val His Phe

<210> SEQ ID NO 61
<211> LENGTH: 322
<212> TYPE: PRT
<213> ORGANISM: Pasteurella multocida

<400> SEQUENCE: 61

Ala Thr Val Tyr Asn Gln Asp Gly Thr Lys Val Asp Val Asn Gly Ser
 1               5                  10                  15

Val Arg Leu Ile Leu Lys Lys Glu Lys Asn Glu Arg Gly Asp Leu Val
            20                  25                  30

Asp Asn Gly Ser Arg Val Ser Phe Lys Ala Ser His Asp Leu Gly Glu
        35                  40                  45

Gly Leu Ser Ala Leu Ala Tyr Ala Glu Leu Arg Phe Ser Thr Lys Val
    50                  55                  60

Lys Lys Thr Val Lys Glu Gly Pro Asn Gln Val Glu Arg Thr Tyr Glu
65                  70                  75                  80
```

-continued

```
Val Glu Arg Ile Gly Asn Asp Val His Val Lys Arg Leu Tyr Ala Gly
                85                  90                  95

Phe Ala Tyr Glu Gly Leu Gly Thr Leu Thr Phe Gly Asn Gln Leu Thr
            100                 105                 110

Ile Gly Asp Asp Val Gly Val Ser Asp Tyr Thr Tyr Phe Leu Gly Gly
        115                 120                 125

Ile Asn Asn Leu Leu Ser Ser Gly Glu Lys Ala Ile Asn Phe Lys Ser
    130                 135                 140

Ala Glu Phe Asn Gly Phe Thr Phe Gly Gly Ala Tyr Val Phe Ser Ala
145                 150                 155                 160

Asp Ala Asp Lys Gln Ala Pro Arg Asp Gly Arg Gly Phe Val Val Ala
                165                 170                 175

Gly Leu Tyr Asn Arg Lys Met Gly Asp Val Gly Phe Ala Leu Glu Ala
            180                 185                 190

Gly Tyr Ser Gln Lys Tyr Val Thr Ala Ala Ala Lys Gln Glu Lys Glu
        195                 200                 205

Lys Ala Phe Met Val Gly Thr Glu Leu Ser Tyr Ala Gly Leu Ala Leu
    210                 215                 220

Gly Val Asp Tyr Ala Gln Ser Lys Val Thr Asn Val Glu Gly Lys Lys
225                 230                 235                 240

Arg Ala Leu Glu Val Gly Leu Asn Tyr Asp Ile Asn Asp Lys Ala Lys
                245                 250                 255

Val Tyr Thr Asp Leu Ile Trp Ala Lys Glu Gly Pro Lys Gly Ala Thr
            260                 265                 270

Thr Arg Asp Arg Ser Ile Ile Leu Gly Ala Gly Tyr Lys Leu His Lys
        275                 280                 285

Gln Val Glu Thr Phe Val Glu Gly Gly Trp Gly Arg Glu Lys Asp Ala
    290                 295                 300

Asn Gly Val Thr Thr Lys Asp Asn Lys Val Gly Val Gly Leu Arg Val
305                 310                 315                 320

His Phe
```

What is claimed is:

1. An isolated and purified *Pasteurella multocida* strain X-73 outer membrane polypeptide (OmpH) comprising SEQ ID NO:2, a peptide thereof, wherein the peptide comprises SEQ ID NO:44 or SEQ ID NO:45, or wherein the peptide comprises SEQ ID NO:44 or SEQ ID NO:45 and is cyclized.

2. The polypeptide of claim 1 wherein the peptide is SEQ ID NO:45 and is cyclized.

* * * * *

UNITED STATES PATENT AND TRADEMARK OFFICE
CERTIFICATE OF CORRECTION

PATENT NO. : 6,495,661 B1
DATED : December 17, 2002
INVENTOR(S) : John R. Glisson and Yugang Luo It is certified that error appears in the above-identified patent and that said Letters Patent is hereby corrected as shown below:

Column 7,
Line 22, delete "aligniept" and insert -- alignment -- therefor.
Line 26, delete "inmicate" and insert -- indicate -- therefor.
Line 28, delete "Serotvpe" and insert -- Serotype -- therefor.
Line 28, delete "Serotvoe" and insert -- Serotype -- therefor.
Line 28, delete "BD" and insert -- ID -- therefor.
Line 29, delete "." after "60" and insert -- , -- therefor.
Line 29, delete "TD" and insert -- ID -- therefor.
Line 29, delete "." after "61" and insert -- , -- therefor.
Line 30, delete "." after "31" and insert -- , -- therefor.
Line 31, delete "." after "33" and insert -- , -- therefor.
Line 31, delete "." after "34" and insert -- , -- therefor.
Line 32, delete "Serotyne" and insert -- Serotype -- therefor.
Line 33, delete "." after "37" and insert -- , -- therefor.
Line 33, delete "." after "38" and insert -- , -- therefor.
Line 34, delete "." after "39" and insert -- , -- therefor.
Line 34, insert -- , -- after "40".
Line 35, delete "Serotye 5" and insert -- Serotype 15 -- therefor.
Line 36, delete "ED" and insert -- ID -- therefor.

Column 27,
Line 9, delete "A-T-V-Y-N-Q-D-G-T-K-VD-V-N-G-S-L-R-X-I" and insert -- The amino terminal 20 residues of the purified OmpH had the sequence A-T-V-Y-N-Q-D-G-T-K-V-D-V-N-G-S-L-R-X-I -- therefor.

Signed and Sealed this

Twenty-sixth Day of August, 2003

JAMES E. ROGAN
*Director of the United States Patent and Trademark Office*